(12) United States Patent
Austad et al.

(10) Patent No.: US 9,879,293 B2
(45) Date of Patent: *Jan. 30, 2018

(54) ENZYMATIC TRANSAMINATION OF CYCLOPAMINE ANALOGS

(71) Applicant: Infinity Pharmaceuticals, Inc., Cambridge, MA (US)

(72) Inventors: Brian C. Austad, Tewksbury, MA (US); Adilah Bahadoor, Cambridge, MA (US); Jitendra D. Belani, Newtonville, MA (US); Somarajannair Janardanannair, Woburn, MA (US); Sheldon L. Wallerstein, Chesterfield, MO (US); Gregg F. Keaney, Belmont, MA (US); Priscilla L. White, Malden, MA (US); Charles W. Johannes, Singapore (SG)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/054,011

(22) Filed: Feb. 25, 2016

(65) Prior Publication Data
US 2016/0177354 A1   Jun. 23, 2016

Related U.S. Application Data

(63) Continuation of application No. 14/257,658, filed on Apr. 21, 2014, now abandoned, which is a continuation of application No. 13/175,053, filed on Jul. 1, 2011, now Pat. No. 8,703,448, which is a continuation of application No. PCT/US2010/044597, filed on Aug. 5, 2010.

(60) Provisional application No. 61/231,439, filed on Aug. 5, 2009.

(51) Int. Cl.
*C12P 17/18* (2006.01)
*C07D 491/10* (2006.01)
*C07D 491/107* (2006.01)

(52) U.S. Cl.
CPC ............ *C12P 17/18* (2013.01); *C07D 491/10* (2013.01); *C07D 491/107* (2013.01)

(58) Field of Classification Search
CPC .... C07D 491/107; C07D 491/10; C12P 17/18
See application file for complete search history.

(56) References Cited

U.S. PATENT DOCUMENTS

| | | | |
|---|---|---|---|
| 4,843,071 A * | 6/1989 | Hohenwarter | A61K 31/55 424/422 |
| 4,968,787 A | 11/1990 | Inada et al. | |
| 5,086,047 A | 2/1992 | Gourvest et al. | |
| 5,169,780 A | 12/1992 | Stirling et al. | |
| 5,378,475 A | 1/1995 | Smith et al. | |
| 5,767,161 A | 6/1998 | Stroppolo et al. | |
| 6,177,407 B1 | 1/2001 | Rodgers et al. | |
| 6,184,381 B1 | 2/2001 | Ikariya et al. | |
| 6,238,876 B1 | 5/2001 | Altaba | |
| 6,291,516 B1 | 9/2001 | Dudek et al. | |
| 6,372,931 B1 | 4/2002 | Blacker et al. | |
| 6,432,970 B2 | 8/2002 | Beachy et al. | |
| 6,509,467 B1 | 1/2003 | Blacker et al. | |
| 6,545,188 B2 | 4/2003 | Blacker et al. | |
| 6,552,016 B1 | 4/2003 | Baxter et al. | |
| 6,613,798 B1 | 9/2003 | Porter et al. | |
| 6,686,388 B2 | 2/2004 | Dudek et al. | |
| 6,867,216 B1 | 3/2005 | Beachy et al. | |
| 6,887,820 B1 | 5/2005 | Ikariya et al. | |
| 6,909,003 B2 | 6/2005 | Storz | |
| 7,098,196 B1 | 8/2006 | Beachy et al. | |
| 7,112,690 B2 | 9/2006 | Chi et al. | |
| 7,230,004 B2 | 6/2007 | Adams et al. | |
| 7,250,526 B2 | 7/2007 | Blacker et al. | |
| 7,291,626 B1 | 11/2007 | Beachy et al. | |
| 7,407,967 B2 | 8/2008 | Adams et al. | |
| 7,476,661 B2 | 1/2009 | Beachy et al. | |
| 7,541,183 B2 | 6/2009 | Rudnicki et al. | |
| 7,605,167 B2 | 10/2009 | Tas et al. | |
| 7,629,352 B2 | 12/2009 | Tas et al. | |
| 7,648,994 B2 | 1/2010 | Castro et al. | |
| 7,655,674 B2 | 2/2010 | Beachy et al. | |
| 7,812,164 B2 | 10/2010 | Austad et al. | |
| 7,867,492 B2 | 1/2011 | Beachy et al. | |
| 7,875,628 B2 | 1/2011 | Adams et al. | |
| 7,893,078 B2 | 2/2011 | Tas et al. | |
| 7,964,590 B2 | 6/2011 | Castro et al. | |
| 7,994,191 B2 | 8/2011 | Castro et al. | |
| 8,017,648 B2 | 9/2011 | Castro et al. | |

(Continued)

FOREIGN PATENT DOCUMENTS

| | | |
|---|---|---|
| EP | 0255331 A2 | 2/1988 |
| EP | 0388188 A1 | 9/1990 |

(Continued)

OTHER PUBLICATIONS

Taylor et al. Tibtech (1998) 16: 412-418.*
Cancer Cluster Salzburg, "CCS researchers identify imiquimod as novel Hedgehog pathway inhibitor in skin cancer", Apr. 29, 2014, retrieved form the internet: URL: http://www.cancercluster-salzberg.at/#!CCS-researchers-identify-imiquimod-as-novel-Hedgehog-pathway-inhibitor-in-skin-cancer/axycm/5687b39c0cf23a10fe3c91fc, accessed on Sep. 28, 2016.

(Continued)

*Primary Examiner* — Susan Hanley

(74) *Attorney, Agent, or Firm* — McDermott Will & Emery LLP

(57) ABSTRACT

The invention relates to the preparation of amino-cyclopamines by the enzymatic transamination of a corresponding keto-cyclopamines in the presence of a cofactor and an amino donor.

30 Claims, 2 Drawing Sheets

(56) References Cited

U.S. PATENT DOCUMENTS

| | | |
|---|---|---|
| 8,227,509 B2 | 7/2012 | Castro et al. |
| 8,236,956 B2 | 8/2012 | Adams et al. |
| 8,293,760 B2 | 10/2012 | Castro et al. |
| 8,426,436 B2 | 4/2013 | Castro et al. |
| 8,431,566 B2 | 4/2013 | Castro et al. |
| 8,669,365 B2 | 3/2014 | Austad et al. |
| 8,703,448 B2 | 4/2014 | Austad et al. |
| 8,716,479 B2 | 5/2014 | Austad et al. |
| 8,785,635 B2 | 7/2014 | Austad et al. |
| 8,895,576 B2 | 11/2014 | Castro et al. |
| 9,145,422 B2 | 9/2015 | Castro et al. |
| 9,238,672 B2 | 1/2016 | Austad et al. |
| 9,376,447 B2 | 6/2016 | Genov et al. |
| 9,394,313 B2 | 7/2016 | Genov et al. |
| 9,492,435 B2 | 11/2016 | Austad et al. |
| 2002/0006931 A1 | 1/2002 | Beachy et al. |
| 2002/0087258 A1 | 7/2002 | Johnson |
| 2002/0193347 A1 | 12/2002 | Bulliard et al. |
| 2003/0114393 A1 | 6/2003 | Liscovitch et al. |
| 2003/0162870 A1 | 8/2003 | Kimura et al. |
| 2003/0175355 A1 | 9/2003 | Tobyn et al. |
| 2003/0220314 A1 | 11/2003 | Shackleton et al. |
| 2004/0023949 A1 | 2/2004 | Baxter et al. |
| 2004/0072913 A1 | 4/2004 | Tas et al. |
| 2004/0072914 A1 | 4/2004 | Tas et al. |
| 2004/0073404 A1 | 4/2004 | Brooks et al. |
| 2004/0110663 A1 | 6/2004 | Dudek et al. |
| 2004/0126359 A1 | 7/2004 | Lamb et al. |
| 2004/0127474 A1 | 7/2004 | Dudek et al. |
| 2004/0247643 A1 | 12/2004 | Martinod et al. |
| 2005/0049218 A1 | 3/2005 | Gilbertson |
| 2005/0112707 A1 | 5/2005 | Altaba et al. |
| 2005/0203061 A1 | 9/2005 | Yamashita et al. |
| 2006/0020020 A1 | 1/2006 | Dudek et al. |
| 2006/0074030 A1 | 4/2006 | Adams et al. |
| 2006/0094660 A1 | 5/2006 | Thomson |
| 2006/0128639 A1 | 6/2006 | Beachy |
| 2006/0142245 A1 | 6/2006 | Beachy et al. |
| 2006/0252073 A1 | 11/2006 | Yilmaz et al. |
| 2007/0003550 A1 | 1/2007 | Antonia et al. |
| 2007/0009530 A1 | 1/2007 | Altaba et al. |
| 2007/0021493 A1 | 1/2007 | Guicherit et al. |
| 2007/0036800 A1 | 2/2007 | Bergstein |
| 2007/0060546 A1 | 3/2007 | Ruat et al. |
| 2007/0179091 A1 | 8/2007 | De Sauvage et al. |
| 2007/0191410 A1 | 8/2007 | Adams et al. |
| 2007/0219250 A1 | 9/2007 | Singh et al. |
| 2007/0231828 A1 | 10/2007 | Beachy et al. |
| 2007/0281040 A1 | 12/2007 | Weichselbaum et al. |
| 2008/0019961 A1 | 1/2008 | Wicha et al. |
| 2008/0057071 A1 | 3/2008 | Watkins et al. |
| 2008/0058298 A1 | 3/2008 | Beachy et al. |
| 2008/0089915 A1 | 4/2008 | Tas et al. |
| 2008/0095761 A1 | 4/2008 | Beachy et al. |
| 2008/0107749 A1 | 5/2008 | Maitra et al. |
| 2008/0118493 A1 | 5/2008 | Beachy et al. |
| 2008/0138379 A1 | 6/2008 | Jennings-Spring |
| 2008/0182859 A1 | 7/2008 | Brunton et al. |
| 2008/0255059 A1 | 10/2008 | Beachy et al. |
| 2008/0262051 A1 | 10/2008 | Balkovec et al. |
| 2008/0269182 A1 | 10/2008 | Pluda et al. |
| 2008/0269272 A1 | 10/2008 | Adams et al. |
| 2008/0287420 A1 | 11/2008 | Castro et al. |
| 2008/0293754 A1 | 11/2008 | Austad et al. |
| 2008/0293755 A1 | 11/2008 | Castro et al. |
| 2009/0012109 A1 | 1/2009 | Austad et al. |
| 2009/0041680 A1 | 2/2009 | Tamarkin et al. |
| 2009/0181997 A1 | 7/2009 | Grayzel et al. |
| 2009/0208579 A1 | 8/2009 | Ueki et al. |
| 2009/0216022 A1 | 8/2009 | Austad et al. |
| 2009/0246841 A1* | 10/2009 | Jamieson ................. C12N 1/12 435/147 |
| 2009/0263317 A1 | 10/2009 | Chen et al. |
| 2009/0286822 A1 | 11/2009 | Tas et al. |
| 2009/0305338 A1 | 12/2009 | Ritala-Nurmi et al. |
| 2010/0003728 A1 | 1/2010 | Jayatilake et al. |
| 2010/0093625 A1 | 4/2010 | Tarasova et al. |
| 2010/0099116 A1 | 4/2010 | Faia et al. |
| 2010/0144775 A1 | 6/2010 | Castro et al. |
| 2010/0210515 A1 | 8/2010 | Nash et al. |
| 2010/0222287 A1 | 9/2010 | McGovern et al. |
| 2010/0273818 A1 | 10/2010 | Beachy et al. |
| 2010/0286114 A1 | 11/2010 | Thomas et al. |
| 2010/0286180 A1 | 11/2010 | Castro et al. |
| 2010/0297118 A1 | 11/2010 | MacDougall et al. |
| 2011/0009442 A1 | 1/2011 | Austad et al. |
| 2011/0034498 A1 | 2/2011 | McGovern et al. |
| 2011/0104254 A1 | 5/2011 | Tas et al. |
| 2011/0135739 A1 | 6/2011 | Carter et al. |
| 2011/0166353 A1 | 7/2011 | Adams et al. |
| 2011/0183948 A1 | 7/2011 | Levine et al. |
| 2011/0230509 A1 | 9/2011 | Castro et al. |
| 2012/0010229 A1 | 1/2012 | MacDougall et al. |
| 2012/0010230 A1 | 1/2012 | MacDougall et al. |
| 2012/0015934 A1 | 1/2012 | Castro et al. |
| 2012/0065218 A1 | 3/2012 | Castro et al. |
| 2012/0065399 A1 | 3/2012 | Genov et al. |
| 2012/0065400 A1 | 3/2012 | Genov et al. |
| 2012/0077834 A1 | 3/2012 | Castro et al. |
| 2012/0083484 A1 | 4/2012 | Castro et al. |
| 2012/0083607 A1 | 4/2012 | Austad et al. |
| 2013/0108582 A1 | 5/2013 | Castro et al. |
| 2013/0108583 A1 | 5/2013 | Castro et al. |
| 2013/0143831 A1 | 6/2013 | Embil et al. |
| 2014/0107142 A1 | 4/2014 | Castro et al. |
| 2014/0371253 A1 | 12/2014 | Austad et al. |
| 2014/0371456 A1 | 12/2014 | Austad et al. |
| 2016/0168193 A1 | 6/2016 | Jayatilake et al. |
| 2016/0177354 A1 | 6/2016 | Austad et al. |
| 2016/0354368 A1 | 12/2016 | Brown et al. |
| 2017/0022212 A1 | 1/2017 | Austad et al. |
| 2017/0029433 A1 | 2/2017 | Genov et al. |

FOREIGN PATENT DOCUMENTS

| | | |
|---|---|---|
| EP | 0434570 A2 | 6/1991 |
| EP | 2225254 A2 | 9/2010 |
| EP | 2443926 A2 | 4/2012 |
| JP | 2010-0514796 A | 5/2010 |
| WO | WO 1994/020520 A1 | 9/1994 |
| WO | WO 1995/018856 A1 | 7/1995 |
| WO | WO 1996/017924 A2 | 6/1996 |
| WO | WO 1997/013518 A1 | 4/1997 |
| WO | WO 1999/049835 A1 | 10/1999 |
| WO | WO 2000/018708 A1 | 4/2000 |
| WO | WO 2000/041545 A2 | 7/2000 |
| WO | WO 2001/009077 A1 | 2/2001 |
| WO | WO 2001/019800 A2 | 3/2001 |
| WO | WO 2001/026644 A2 | 4/2001 |
| WO | WO 2001/027135 A3 | 4/2001 |
| WO | WO 2001/049279 A2 | 7/2001 |
| WO | WO 2001/074344 A2 | 10/2001 |
| WO | WO 2001/090077 A1 | 11/2001 |
| WO | WO 2002/030462 A2 | 4/2002 |
| WO | WO 2002/078703 A1 | 10/2002 |
| WO | WO 2002/078704 A1 | 10/2002 |
| WO | WO 2003/011219 A2 | 2/2003 |
| WO | WO 2003/088964 A1 | 10/2003 |
| WO | WO 2003/088970 A2 | 10/2003 |
| WO | WO 2004/020599 A2 | 3/2004 |
| WO | WO 2004/058976 A2 | 7/2004 |
| WO | WO 2005/013800 A2 | 2/2005 |
| WO | WO 2005/032343 A2 | 4/2005 |
| WO | WO 2005/033288 A2 | 4/2005 |
| WO | WO 2005/042700 A2 | 5/2005 |
| WO | WO 2006/026430 A1 | 3/2006 |
| WO | WO 2006/028958 A2 | 3/2006 |
| WO | WO 2006/050351 A2 | 5/2006 |
| WO | WO 2006/078283 A2 | 7/2006 |
| WO | WO 2007/053596 A1 | 5/2007 |
| WO | WO 2007/054623 A2 | 5/2007 |
| WO | WO 2007/059157 A1 | 5/2007 |
| WO | WO 2007/093372 A1 | 8/2007 |
| WO | WO 2007/120827 A2 | 10/2007 |

(56) References Cited

FOREIGN PATENT DOCUMENTS

| WO | WO 2007/123511 A2 | 11/2007 |
|---|---|---|
| WO | WO 2007/131201 A2 | 11/2007 |
| WO | WO 2008/011071 A1 | 1/2008 |
| WO | WO 2008/037732 A1 | 4/2008 |
| WO | WO 2008/063165 A1 | 5/2008 |
| WO | WO 2008/070357 A2 | 6/2008 |
| WO | WO 2008/083248 A2 | 7/2008 |
| WO | WO 2008/083252 A2 | 7/2008 |
| WO | WO 2008/089123 A2 | 7/2008 |
| WO | WO 2008/109184 A1 | 9/2008 |
| WO | WO 2008/109829 A1 | 9/2008 |
| WO | WO 2008/110611 A1 | 9/2008 |
| WO | WO 2008/112913 A1 | 9/2008 |
| WO | WO 2008/131354 A2 | 10/2008 |
| WO | WO 2009/086416 A1 | 7/2009 |
| WO | WO 2009/086451 A1 | 7/2009 |
| WO | WO 2009/099625 A2 | 8/2009 |
| WO | WO 2009/126840 A1 | 10/2009 |
| WO | WO 2010/000070 A1 | 1/2010 |
| WO | WO 2010/002970 A2 | 1/2010 |
| WO | WO 2010/085654 A1 | 7/2010 |
| WO | WO 2011/017551 A1 | 2/2011 |
| WO | WO 2011/041075 A1 | 4/2011 |
| WO | WO 2011/057222 A1 | 5/2011 |
| WO | WO 2011/063309 A1 | 5/2011 |
| WO | WO 2012/006584 A2 | 1/2012 |
| WO | WO 2012/006589 A2 | 1/2012 |
| WO | WO 2012/037217 A1 | 3/2012 |
| WO | WO 2013/049332 A1 | 4/2013 |

OTHER PUBLICATIONS

Deng et al., "External preparation useful for preparing drug for treating infectious disease caused by fungi, comprises nanosized itraconazole and matrix", Database WPI, Thomson Scientific, London, GB, AN: 2011-H84807, PN: CN102085176, 4 pgs. (2011) Abstract.

Jiang et al., "Solution type spray of animycotic medicine for external application and its preparation method", Database WPI, Thomson Scientific, London, GB, AN: 2003-258153, PN: CN1380060, 4 pgs (2002) Abstract.

Park et al., "Composition useful for treating skin fungal infections, comprises itraconazole, phenol and phenolic alcohol", Database WPI, Thomson Scientific, London, GB, AN: 2010-F87592, PN: KR20100051293, 4 pgs. (2010) Abstract.

Tang et al., "Antitumor activity of extracts and compounds from the rhizomes of Veratrum dahuricum", Phytother. Res., vol. 22, No. 8, pp. 1093-1096 (2008).

Hashimoto, "Simmons-Smith reaction without hydroxyl groups", Chemical, vol. 61, No. 1, pp. 63-64 (2006) Japanese language with English translation.

Simmons and Smith, "A new synthesis of cyclopropanes from olefins", J. Am. Chem. Soc., vol. 80, No. 19, pp. 5323-5324 (1958).

Tschesche et al., "Concerning the biosynthesis of steroid derivatives in the plant kingdom, $3^{rd}$ mess.[1]: Spirostanol-biogenesis from cholesterol-glucoside", Z. Naturforsch, vol. 21b pp. 494-495 (1966) German language with English translation.

Aboulkassim et al., "Alteration of the PATCHED locus in superficial bladder cancer", Oncogene, vol. 22, No. 19, pp. 2967-2971 (2003).

Ahlford, "Asymmetric transfer hydrogenation of ketones, catalyst development and mechanistic investigation", Department of Organic Chemistry, Stockholm University, US-AB Stockholm, pp. 1-49 (2011).

Ailles and Siu, "Targeting the hedgehog pathway in cancer: can the spines be smoothened?", Clin. Cancer Res.; vol. 17, No. 8, pp. 2071-2073 (2011).

Alexandre et al., "Transcriptional activation of hedgehog target genes in Drosophila is mediated directly by the Cubitus interruptus protein, a member of the GLI family of zinc finger DNA-binding proteins", Genes Dev., vol. 10, pp. 2003-2013 (1996).

Alonso et al., "Ru(arene)(amino alcohol)-catalyzed transfer hydrogenation of ketones: mechanism and origin of enantioselectivity", J. Am. Chem. Soc., vol. 121, pp. 9580-9588 (1999).

Athar et al., "Hedgehog signaling in skin development and cancer", Exp. Dermatol., vol. 15, No. 9, pp. 667-677 (2006).

Bailey et al., "Sonic hedgehog promotes desmoplasia in pancreatic cancer", Clin. Cancer Res., vol. 14, No. 19, pp. 5995-6004 (2008).

Bailey et al., "Sonic hedgehog paracrine signaling regulates metastasis and lymphangiogenesis in pancreatic cancer", Oncogene, vol. 28, No. 40, pp. 3513-3525 (2009).

Bale and Yu, "The hedgehog pathway and basal cell carcinomas", Human Molecular Genetics, vol. 10, No. 7, pp. 757-762 (2001).

Banerjee et al., "Recruitment of the sonic hedgehog signalling cascade in electroconvulsive seizure-mediated regulation of adult rat hippocampal neurogenesis", Eur. J. Neurosci., vol. 22, No. 7, pp. 1570-1580 (2005).

Bar et al., "Cyclopamine-mediated hedgehog pathway inhibition depletes stem-like cancer cells in glioblastoma", Stem Cells, vol. 25, No. 10, pp. 2524-2533 (2007).

Barken et al., "Noscapine inhibits human prostate cancer progression and metastasis in a mouse model", Anticancer Res., vol. 28, No. 6A, pp. 3701-3704 (2008).

Belloni et al., "Identification of Sonic hedgehog as a candidate gene responsible for holoprosencephaly", Nature Genetics, vol. 14, pp. 353-356 (1996).

Berge et al., "Pharmaceutical salts", J. Pharm. Sci., 66, No. 1, pp. 1-19 (1977).

Berger et al., "Regulator of G-protein signaling-5 induction in pericytes coincides with active vessel remodeling during neovacularization", Blood, vol. 105, No. 3, pp. 1094-1101 (2005).

Berman et al., "Medulloblastoma growth inhibition by hedgehog pathway blockade", Science, vol. 297, pp. 1559-1561 (2002).

Berman et al., "Widespread requirement for Hedgehog ligand stimulation in growth of digestive tract tumours", Nature, vol. 425, pp. 846-851 (2003).

Bhat et al., "Synthesis and biological evaluation of novel steroidal pyrazoles as substrates for bile acid transporters", Bioorg. Med. Chem. Lett., vol. 15, pp. 85-87 (2005).

Bhattacharya et al., "Role of Hedgehog signaling in ovarian cancer", Clin. Cancer Res., vol. 14, No. 23, pp. 7659-7666 (2008).

Biospace, Print News Article, "Infinity Pharmaceuticals, Inc. Announces Hedgehog Pathway Inhibitor Agreement with AstraZeneca PLC (AZ)", Cambridge, Mass., Nov. 12, 2007, (Prime Newswire), 2 pages, Retrieved from the internet: http://www.biospace.com/news_story.aspx?NewsEntityID=77067.

Brown and Keeler, "Structure-activity relation of steroid teratogens, 1. Jervine ring system", J. Agric. Food Chem., vol. 26, No. 3, pp. 561-563 (1978).

Brown and Keeler, "Structure-activity relation of steroid teratogens, 2. N-substituted jervines", J. Agric. Food Chem., vol. 26, No. 3, pp. 564-566 (1978).

Browne et al., "Isolation of teratogenic alkaloids by reversed-phase high-performance liquid chromatography" Journal of Chromatography Biomedical Applications, vol. 336, pp. 211-220 (1984).

Business Wire, "Infinity Reports Update from Phase 2 Study of Saridegib Plus Gemcitabine in Patients with Metastatic Pancreatic Cancer", Infinity Pharmaceuticals, 3 pages, Jan. 27, 2012, Retrieved from the internet: http://www.businesswire.com/news/home/20120127005146/en/Infinity-Reports-Update-Phase-2-Study-Saridegib#.U3Us_IdV8E.

Campbell et al., "Direct Targeting of the Hedgehog pathway in primary chondrosarcoma xenografts with smoothened Inhibitor IPI-926", Infinity Pharmaceuticals, Inc., Presentation Poster, Abstract #LB380, 1 page (2011).

Carter et al., "Formulation for IPI-926 drug product, a novel oral Hedgehog pathway inhibitor in clinical development", Infinity Pharmaceuticals, Inc., Presentation Poster, Abstract #M1169, with Presentation Abstract, 2 pages (2009).

Caserta et al., "p63 overexpression induces the expression of sonic hedgehog", Mol. Cancer Res., vol. 4, No. 10, pp. 759-768 (2006).

(56) References Cited

OTHER PUBLICATIONS

Chaumeil, "Micronization: A method of improving the bioavailability of poorly soluble drugs", Methods Find. Exp. Clin. Pharmacol., vol. 20, No. 3, pp. 211-215 (1998).
Chen et al., "Inhibition of Hedgehog signaling by direct binding of cyclopamine to smoothened", Genes Dev., vol. 16, No. 21, pp. 2743-2748 (2002).
Chen et al., "Small molecule modulation of Smoothened activity", PNAS, vol. 99, No. 22, pp. 14071-14076 (2002).
Chen et al., "Targeting the hedgehog pathway to mitigate treatment resistance", Cell Cycle, vol. 6, Issue. 15, pp. 1826-1830 (2007).
Chen et al., "Sonic hedgehog dependent phosphorylation by CK1α and GRK2 is required for ciliary accumulation and activation of smoothened", PloS Biology, vol. 9, Issue. 6, No. e1001083, 16 pages (2011).
Christiansen et al., "Antiandrogenic steroidal sulfonylpyrazoles", J. Med. Chem., vol. 33, pp. 2094-2100 (1990).
Chung et al., "New targets for therapy in prostate cancer; modulation of stromal-epithelial interactions", Urology, vol. 62, Suppl. 5A, pp. 44-54 (2003).
Clement et al., "Hedgehog-GLI1 signaling regulates human glioma growth, cancer stem cell self-renewal and tumorigenicity", Curr. Biol., vol. 17, No. 2, pp. 165-172 (2007).
Clinton et al., "Steroidal heterocycles, VI. Formulation of A/B-cis 3-Ketosteroids. Preparation of 5β-Steroidal[3,2-c]pyrazoles", J. Org. Chem., vol. 27, pp. 2800-2807 (1962).
COMTEX, "Infinity announces hedgehog pathway inhibitor agreement with Astra-Zeneca", Infinity Pharmaceuticals, PrimeWireNewswire via COMTEX News Network, 2 pages, Nov. 12, 2007, Retrieved from the internet: http://files.shareholder.com/downloads/INFI/0x0x144355/71ecb752-43b2-4a26-9867-8feea13ee93d/INFI_News_2007_11_12_General.pdf.
Cong et al., "Steroidal alkaloids from the roots and rhizomes of Veratrum nigrum L", Helvetica Chimica Acta, vol. 90, Issue 5, pp. 1038-1042 (2007).
Cooper et al., "Teratogen-mediated inhibition of target tissue response to Shh signaling", Science, vol. 280, pp. 1603-1607 (1998).
Corbit et al., "Vertebrate smoothened functions at the primary cilium", Nature, vol. 437 No. 7061, pp. 1018-1021 (2005).
Cutcliffe et al., "Clear cell sarcoma of the kidney: Up-regulation of neural markers with activation of the sonic hedgehog and Akt pathways", Clin. Cancer Res., vol. 11, No. 22, pp. 7986-7994 (2005).
Dakhova et al., "Global gene expression analysis of reactive stroma in prostate cancer", Clin. Cancer Res., vol. 15, No. 12, pp. 3979-3989 (2009).
Dersnah and Baird, "Chiral $\eta^6$-$C_6H_6$ ruthenium complexes", J. Org. Chem., vol. 127, C55-C58 (1977).
Dierks et al., "Essential role of stromally induced hedgehog signaling in B-cell malignancies", Nat. Med., vol. 13, No. 8, pp. 944-951 (2007) Pre Publication Article, DOI:10.1038/nm1614 pp. 1-8 (2007).
Dierks et al., "Expansion of Bcr-Abl-positive leukemic stem cells is dependent on Hedgehog pathway activation", Cancer Cell, vol. 14, No. 3, pp. 238-249 (2008).
Di Magliano and Hebrok, "Hedgehog signalling in cancer formation and maintenance", Nat. Rev., vol. 3, No. 12, pp. 903-911 (2003).
Djerassi and Gutzwiller, "Selective reduction of steroids by homogeneous catalytic hydrogenation", J. Am. Chem. Soc., vol. 88, No. 19, pp. 4537-4538 (1966).
Dormeyer et al., "Plasma membrane proteomics of human embryonic stem cells and human embryonal carcinoma cells", J. Proteome Res., vol. 7, No. 7, pp. 2936-2951 (2008).
Dörwald, "Side reactions in organic synthesis, A guide to successful synthesis design", Wiley-VCH, Verlag GmbH & Co. KGaA, Weinheim, ISBN:3-527-31021-5, p. IX of Preface and pp. 8-13 (2005).

Ehtesham et al., "Ligand-dependent activation of the hedgehog pathway in glioma progenitor cells", Oncogene, vol. 26, No. 39, pp. 5752-5761 (2007).
Engelman and Settleman, "Acquired resistance to tyrosine kinase inhibitors during cancer therapy", Curr, Opin. Genet. Dev., vol. 18, No. 1, pp. 73-79 (2008).
Everaere et al., "Ruthenium (II)-catalyzed asymmetric transfer hydrogenation of carbonyl compounds with 2-propanol and ephedrine-type ligands", Adv. Synth. Catal., vol. 345, No. 1&2, pp. 67-77 (2003).
Fahrenholtz et al., "Cycloprop[16α, 17α] androstanes", J. Med. Chem., vol. 15, No. 10, pp. 1056-1060 (1972).
Faia et al., "Depilation induced anagen as a model to study hedgehog pathway antagonist IPI-926: Implications for biomarker development", AACR Meeting Abstracts Online, Abstract #2827, with Infinity Pharmaceuticals Poster, 3 pages (2008).
Fan et al., "Hedgehog singaling promotes prostate xenograft tumor growth", Endocrinology, vol. 145, No. 8, pp. 3961-3970 (2004).
Feldmann et al., "Blockade of hedgehog signaling inhibits pancreatic cancer invasion and metastases: A new paradigm for combination therapy in solid cancers", Cancer Res., vol. 67, No. 5, pp. 2187-2196 (2007).
Feldmann et al., "An orally bioavailable small-molecule inhibitor of Hedgehog signaling inhibits tumor initiation and metastasis in pancreatic cancer", Mol. Cancer Ther., vol. 7, No. 9, pp. 2725-2735 (2008).
Geng et al., "Hedgehog signaling in the murine melanoma microenvironment", Angiogenesis, vol. 10, No. 4, pp. 259-267, DOI: 10.1007/s10456-007-9078-9 (2007).
Genov and Ager, "Asymmetric hydrogenation of ketones catalyzed by $Ru^{II}$-bicp complexes", Angew. Chem. Int. Ed. Engl., vol. 43, No. 21, pp. 2816-2819 (2004).
Giannis et al., "Synthesis of cyclopamine using a biomimetic and diastereoselective approach", Angew. Chem. Int. Ed., vol. 48, pp. 1-5 (2009).
Goldberg et al., "Resolution of odontogenic keratocysts of the jaw in basal cell nevus syndrome with GDC-0449", Arch Dematol., vol. 147, No. 7, pp. 839-841 (2011).
Green, "A new approach to the formal classification of covalent compounds of the elements", Journal of Organometallic Chemistry, vol. 500, Issue 1-2, pp. 127-148 (1995).
Grogan et al., "Synthesis and structure activity relationship of D-homo cyclopamine analogs: A-ring fused heterocyclic analogs", MEDI 97, 237th ACS National Meeting, Infinity Pharmaceuticals, Inc., Presentation Poster, with Presentation Abstract, 2 pgs. (2009).
Growdon et al., "Hedgehog pathway inhibitor cyclopamine suppresses Gli1 expression and inhibits serous ovarian cancer xenograft growth", 40th Annual Meeting on Women's Cancer, Feb. 5-8, 2009, Presentation Slides, 16 pages (2009).
"Guidance for industry: Clinical trial endpoints for the approval of cancer drugs and biologics", US Dept. of Health Services, FDA, CDER and CBER, Section III, p. 4-9 (2007).
Guijarro et al., "Achiral β-amino alcohols as efficient ligands for the ruthenium-catalysed asymmetric transfer hydrogenation of sulfinylimines", Tetrahedron Letters, vol. 52, Issue 7, pp. 789-791 (2011), pre-publication accepted manuscript, DOI:10.1016/j.tetlet.2010.12.031, 6 pgs. (2010).
Hanahan et al., "Less is more, regularly: metronomic dosing of cytotoxic drugs can target tumor angiogenesis in mice", J. Clin. Inv., vol. 105, No. 8, pp. 1045-1047 (2000).
Harrington et al., "Targeted radiosensitisation by pegylated liposome-encapsulated 3', 5'-O-dipalmitoyl 5-iodo-2'-deoxyuridine in a head and neck cancer xenograft model," Br. J. Cancer, vol. 91, No. 2, pp. 366-373 (2004).
Harris et al., "Hedgehog signaling: Networking to nurture a premalignant tumor microenvironment", Mol. Cancer Res., vol. 9, No. 9, pp. 1165-1174 (2011).
Hashiguchi et al., "Asymmetric transfer hydrogenation of aromatic ketones catalyzed by chiral ruthenium (II) complexes", J. Am. Chem. Soc., vol. 117, No. 28, pp. 7562-7563 (1995).
Hawley's Condensed Chemical Dictionary, 15th edition, Lewis, ed., John Wiley & Sons, New York, pp. 38 and 100 (2007).

(56) References Cited

OTHER PUBLICATIONS

Heftmann, "Recent progress in the biochemistry of plant steroids other than steroids (saponins, glycoalkaloids, pregnana derivatives, cardiac glycosides, and sex hormones)", Lipids, vol. 9, No. 8, pp. 626-639 (1974).
Hegde et al., "Hedgehog-induced survival of B-cell chronic lymphocytic leukemia cells in a stromal cell microenvironment: a potential new therapeutic target", Mol. Cancer Res., vol. 6, No. 12, pp. 1928-1936 (2008).
Heretsch et al., "Cyclopamine and hedgehog signaling: chemistry, biology, medical perspectives", Angew. Chem. Int. Ed., vol. 49, pp. 2-12, DOI: 10.1002/anie.200906967 (2010).
Holton and Necoechea, "Steroids. CLXXV. Further steroidal anabolic agents", J. Med. Chem., pp. 1352-1357 (1962).
Huangfu et al., "Hedgehog signalling in the mouse requires intraflagellar transport proteins", Nature, vol. 426, No. 6962, pp. 83-87 (2003).
Ikariya et al., "Bifunctional transition metal-based molecular catalysts for asymmetric synthesis", Org. Biomol. Chem., vol. 4, No. 3, pp. 393-406 (2006).
Incardona et al., "Cyclopamine inhibition of sonic hedgehog signal transduction is not mediated through effects on cholesterol transport", Dev. Biol., vol. 224, No. 2, pp. 440-452 (2000).
International Search Report from International Patent Application No. PCT/US2005/030406, 2 pages, dated Apr. 4, 2006, application now published as International Patent Publication No. WO2006/026430 on Mar. 9, 2006.
International Search Report from International Patent Application No. PCT/US2006/010796, 9 pages, dated May 15, 2008.
International Search Report from International Patent Application No. PCT/US2007/088990, 2 pages, dated Aug. 1, 2008.
International Search Report from International Patent Application No. PCT/US2007/088995, 6 pages, dated Aug. 1, 2008.
International Search Report from International Patent Application No. PCT/US2008/003200, 3 pages, dated Aug. 11, 2008.
International Search Report from International Patent Application No. PCT/US2008/050970, 3 pages, dated Aug. 22, 2008.
International Search Report from International Patent Application No. PCT/US2008/056229, 4 pages, dated Aug. 11, 2008.
International Search Report from International Patent Application No. PCT/US2008/088222, 6 pages, dated Feb. 23, 2009.
International Search Report from International Patent Application No. PCT/US2008/088302, 1 pages, dated Mar. 25, 2009.
International Search Report from International Patent Application No. PCT/US2009/049372, 3 pages, dated Mar. 16, 2010.
International Search Report from International Patent Application No. PCT/US2010/021816, 3 pages, dated Jun. 2, 2010.
International Search Report from International Patent Application No. PCT/US2010/044597, 2 pages, dated Oct. 1, 2010.
International Search Report from International Patent Application No. PCT/US2010/055879, 12 pages, dated Jan. 24, 2011.
International Search Report from International Patent Application No. PCT/US2010/057534, 2 pages, dated Jan. 18, 2011.
International Search Report from International Patent Application No. PCT/US2011/043446, 5 pages, dated Oct. 16, 2012.
International Search Report from International Patent Application No. PCT/US2011/043453, 4 pages, dated Mar. 14, 2012.
International Search Report from International Patent Application No. PCT/US2011/051553, 2 pages, dated Feb. 2, 2012.
Iselin et al., "Structure of jervine, VI. The sulfuric acid-catalyzed acetolysis of N-acetyl-3-deoxy-3 alpha.-chlorotetrahydro jervine", J. Am. Chem. Soc., vol. 76, pp. 5616-5620 (1954) Database Accession No. 1955:73589, XP-002672119, 4 pgs. (1954).
Iselin et al., "Jervine, IX. Miscellaneous new derivatives", J. Am. Chem. Soc., vol. 78, No. 2, pp. 403-407 (1956) Database Accession No. 1956:69487, XP-002672116. 3 pgs. (1956).
Jacobs and Craig, "The veratrine alkaloids, XXII. On pseudojervine and veratrosine, a companion glycoside in veratrum viride", J. Biol. Chem., vol. 155, 565-572 (1944).
Jacobs and Craig, "The veratrine alkaloids, XXV. The alkaloids of veratrum viride", J. Biol. Chem., vol. 160, pp. 555-565 (1945).
Jacobs and Huebner, "Veratrine alkaloids, XXVII. Further studies with jervine", J. Biol. Chem., vol. 170, pp. 635-652 (1947).
James et al., "Biomedical applications of poisonous plant research", J. Agric. Food Chem., vol. 52, pp. 3211-3230 (2004).
Ji et al., "Protein kinase A, not EPAC, suppresses hedgehog activity and regulates glucocorticoid sensitivity in acute lymphoblastic leukemia cells", J. Biol. Chem., vol. 282, No. 52, pp. 37370-37377 (2007).
Kaneko et al., "Biosynthesis of C-nor-D-homo-steroidal alkaloids from acetate-I-$^{14}$C, cholesterol-4-$^{14}$C and cholesterol-26-$^{14}$C in veratrum grandiflorum", Phytochemistry, vol. 9, pp. 2489-2495 (1970).
Kaneko et al., "11-deoxojervine as a precursor for jervine biosynthesis in veratrum grandiflorum", Phytochemistry, vol. 9, pp. 2497-2501 (1970).
Kaneko et al., "Conversion of solanidine to jervatrum alkaloids in veratrum grandiflorum", Phytochemistry, vol. 11, pp. 3199-3202 (1972).
Kaneko et al., "Biosynthesis of rubijervine in veratrum grandiflorum" Phytochemistry, vol. 14, pp. 1295-1301 (1975).
Kaneko et al., "Origin of nitrogen in the biosynthesis of solanidine by veratrum grandiflorum", Phytochemistry, vol. 15, pp. 1391-1393 (1976).
Kaneko et al., "Dormantinol, a possible precursor in solanidine biosynthesis from budding veratrum grandiflorum", Phytochemistry, vol. 16, pp. 1247-1251 (1977).
Karhadker et al., "Hedgehog signalling in prostate regeneration, neoplasia and metastasis", Nature, 431, pp. 707-712 (2004).
Kayed et al., "Distribution of indian hedgehog and its receptors patched and smoothened in human chronic pancreatitis", J. Endocrinol., vol. 178, No. 3, pp. 467-478 (2003).
Kayed et al., "Indian hedgehog signaling pathway: expression and regulation in pancreatic cancer", Int. J. Cancer; vol. 110, No. 5, pp. 668-676 (2004).
Keeler and Binns, "Chemical compounds of veratrum californicum related to congenital ovine cyclopian malformations: extraction of active material", Proc. Soc. Exptl. Biol. Med., vol. 116, pp. 123-127 (1964).
Keeler and Binns, "Teratogenic compounds of veratrum californicum (Durand), I. Preparation and characterization of fractions and alkaloids for biologic testing", Canadian Journal of Biochemistry, vol. 44, No. 6, pp. 819-828 (1966).
Keeler and Binns, "Teratogenic compounds of veratrum californicum (Durand), II. Production of ovine fetal cyclopia by fractions and alkaloid preparations", Can. J. Biochem., vol. 44, pp. 829-838 (1966).
Keeler, "Teratogenic compounds of veratrum californicum (Durand), IV. First isolation of veratramine and alkaloid Q and a reliable method for isolation of cyclopamine", Phytochemistry, vol. 7, pp. 303-306 (1968).
Keeler, "Toxic and teratogenic alkaloids of western range plants", J. Agr. Food Chem., vol. 17, No. 3, pp. 473-482 (1969).
Keeler, "Teratogenic Compounds of Veratrum Californicum (Durand) VII. The Structure of the glycosidic alkaloid cycloposine", Steroids, vol. 13, No. 5, pp. 579-588 (1969).
Keeler and Binns, "Teratogenic compounds of veratrum californicum as a function of plant part, stage, and site of growth", Phytochemistry, vol. 10, pp. 1765-1769 (1971).
Keeler, "Isolation of rubijervine from veratrum-californicum", Phytochemistry, vol. 13, pp. 2336-2337 (1974).
Keeler and Baker, "Oral, osmotic minipump, and intramuscular administration to sheep of the veratrum alkaloid cyclopamine (42970)", Cyclopamine Administration to Sheep, P.S.E.B.M., vol. 192, pp. 153-156 (1989).
Kenney et al., "Hedgehog and PI-3 kinase signaling converge on Nmyc1 to promote cell cycle progression in cerebellar neuronal precursors", Development, vol. 131, No. 1, pp. 217-228 (2004).
Kerbal and Kamen, "The anti-angiogenic basis of metronomic chemotherapy", Nature Rev., Cancer, vol. 4, pp. 423-436 (2004).
King, "Roughening up smoothened: chemical modulators of hedgehog signaling", J. Biol., vol. 1, No. 8, pp. 8.1-8.4 (2002).

(56) References Cited

OTHER PUBLICATIONS

Kitajima et al., "Steroid alkaloids of fresh bulbs of fritillaria thunbergii miq. and of crude drug "BAI-MO" prepared therefrom", Heterocycles, vol. 15, No. 2, pp. 791-796 (1981).
Koszelewski et al., "Formal asymmetric biocatalytic reductive amination", Angew. Chem. Int. Ed., vol. 47, No. 48, pp. 9337-9340 (2008).
Koszelewski et al., "ω-transaminases for the synthesis of non-racemic α-chiral primary amines", Trends Biotechnol., vol. 28, No. 6, pp. 324-332 (2010).
Kubo et al., "Hedgehog signaling pathway is a new therapeutic target for patients with breast cancer", Cancer Research, vol. 64, pp. 6071-6074 (2004).
Lacasse et al., "Iodomethylzinc phosphates: powerful reagents for the cyclopropanation of alkenes", J. Am. Chem. Soc., vol. 127, No. 36, pp. 12440-12441 (2005).
Lee et al., "Development of an enzyme-linked immunosorbent assay for the veratrum plant teratogens: cyclopamine and jervine", J. Agric. Food Chem., vol. 51, No. 3, pp. 582-586 (2003).
Leontjev et al., "Reduction of steroidal ketones with amine-boranes", Russian Chemical Bulletin, vol. 53, No. 3, pp. 703-708 (2004).
Lescarbeau et al., "Synthesis and structure activity relationship of D-homo cyclopamine hedgehog antagonists: 7-membered A-ring lactam analogs", MEDI 98, 237th ACS National Meeting, Infinity Pharmaceuticals, Inc., Poster, with Presentation Abstract, 2 pgs. (2009).
Lewis and Veltmaat, "Next stop, the twilight zone: hedgehog network regulation of mammary gland development", J. Mamm. Gland Biol. Neopl., vol. 9, No. 2, pp. 165-181 (2004).
Li et al., "Chemistry, bioactivity and geographical diversity of steroidal alkaloids from the Liliaceae family", Natural Product Reports, vol. 23, pp. 735-752 (2006).
Li et al., "Mesodermal deletion of transforming growth factor-β receptor II disrupts lung epithelial morphogenesis: cross-talk between TGF-β and sonic hedgehog pathways", J. Biol. Chem., vol. 283, No. 52, pp. 36257-36264 (2008).
Lin et al., "Self-renewal of acute lymphocytic leukemia cells is limited by the hedgehog pathway inhibitors cyclopamine and IPI-926", PLoS One, vol. 5, Issue 12, No. e15262, pp. 1-8 (2010).
Lindemann, "Stroma-initiated hedgehog signaling takes center stage in B-cell lymphoma", Cancer Res., vol. 68, No. 4, pp. 961-964 (2008).
Lipinski et al., "Dose- and route-dependent teratogenicity, toxicity, and pharmacokinetic profiles of the hedgehog signaling antagonist cyclopamine in the mouse", Toxicol. Sci. Advanced Access Publication, 28 pages, (2008).
Ma et al., "Frequent activation of the hedgehog pathway in advanced gastric adenocarcinomas", Carcinogenesis, vol. 26, No. 10, pp. 1698-1705 (2005).
Ma et al., "Study of sonic hedgehog signaling pathway related molecules in gastric carcinoma", World J. Gastroenterol., vol. 12, No. 25, pp. 3965-3969 (2006).
Ma et al., "Development of in vitro techniques for the important medicinal plant veratrum californicum", Planta Medica, vol. 72, pp. 1142-1148 (2006).
Mandley et al., "The Hh inhibitor IPI-926 delays tumor re-growth of a non-small cell lung cancer xenograft model following treatment with an EGFR targeted tyrosine kinase inhibitor", Infinity Pharmaceuticals, Inc., Presentation Poster, Abstract #5045, 1 page (2010).
Manna et al., "Metabolite identification of IPI-609, a novel and potent inhibitor of the hedgehog pathway, in different species", Infinity Pharmaceuticals, Inc., Presentation Poster, 1 page (2008).
Mao et al., "First example of asymmetric transfer hydrogenation in water induced by a chiral amino alcohol hydrochloride", Tetrahedron Letters, vol. 46, pp. 7341-7344 (2005),
Masamune et al., "11-Deoxojervine, a new alkaloid form *Veratrum* species", Bull. Chem. Soc. Japan, vol. 38, No. 8, pp. 1374-1378 (1965).
Masamune et al., "Syntheses and NMR spectra of 22,27-imino-17,23-oxidojervane derivatives", Tetrahedron, vol. 23, No. 4, pp. 1591-1612 (1967).
Masamune et al., "Synthesis of jervine and related alkaloids", J, Am. Chem. Soc., vol. 89, No. 17, pp. 4521-4523 (1967).
Masamune et al., "The stereochemistry of dihydrojervine and related compounds: The ORD curves of 11-oxoetiojervanes and 11-oxoiminojervanes", Tetrahedron, vol. 25, Issue 19, pp. 4853-4871 (1969).
Mazur, "Azasteroids III. 3-aza-a-homo androgens", J. Org. Chem., vol. 28, pp. 248-250 (1963).
Meloni et al., "Smoothened signal transduction is promoted by G protein-coupled receptor kinase 2", Mol. Cell. Biol., vol. 26, No. 20, pp. 7550-7560 (2006).
Metcalfe and De Sauvage, "Hedgehog fight back: mechanisms of acquired resistance against smoothened antagonists", Cancer Res; vol. 71, No. 15, pp. 5057-5061 and 6087 (2011).
Mrozik et al., "Heterocyclic steroids in the antiinflammatory series", J. Med. Chem., vol. 7, pp. 584-589 (1964).
Müller-Röver et al., A comprehensive guide for the accurate classification of murine hair follicles in distinct hair cycle stages, J. Invest. Dermatol., vol. 117, No. 1, pp. 3-15 (2001).
Nakamura et al., "Induction of osteogenic differentiation by hedgehog proteins", Biochem. Biophys. Res. Comm., vol. 237, pp. 465-469 Article No. RC977156 (1997).
Niemann et al., "Indian hedgehog and β-catenin signaling: Role in the sebaceous lineage of normal and neoplastic mammalian epidermis", PNAS, vol. 100, Suppl. 1, pp. 11873-11880 (2003).
Nolan-Stevaux et al., "GLI1 is regulated through smoothened-independent mechanisms in neoplastic pancreatic ducts and mediates PDAC cell survival and transformation", Genes Dev., vol. 23, No. 1, pp. 24-36 (2009).
Noyori and Hashiguchi, "Asymmetric transfer hydrogenation catalyzed by chiral ruthenium complexes", Acc. Chem Res., vol. 30, No. 2, pp. 97-102 (1997).
Oatis et al., "Isolation purification and full NMR assignments to cyclopamine from veratrum californicum", Chemistry Central Journal, vol. 2, No. 12, 17 pgs. (2008).
Ohta et al., "Investigations on steroids, XI. Synthesis of steroidal oxazole, imidazole, and triazole", Chem. Pharm. Bull. vol. 16, No. 8, pp. 1487-1497 (1968).
Ohta et al., "p53-independent negative regulation of p21/cyclin-dependent kinase-interacting protein 1 by the sonic hedgehog-glioma-associated oncogene 1 pathway in gastric carcinoma Cells", Cancer Res., vol. 65, No. 23, pp. 10822-10829 (2005).
Oka and Hara, "Regiospecific Beckmann rearrangement of 3-oxo-4-ene steroid oximes", J. Org. Chem., vol. 43, No. 19, pp. 3790-3791 (1978).
Oka and Hara, "Synthesis of A-azasteroids by the use of specific Beckmann rearrangement", Chemistry and Industry, pp. 168-170 (1969).
Olive et al., "Inhibition of hedgehog signaling enhances delivery of chemotherapy in a mouse model of pancreatic cancer", Science, vol. 324, No. 5933, pp. 1457-1461 (2009).
Oro and Higgins, "Hair cycle regulation of hedgehog signal reception", Dev. Biol., vol. 255, No. 2, pp. 238-248 (2003).
Paladini et al., "Modulation of hair growth with small molecule agonists of the hedgehog signaling pathway", J. Invest. Dermatol., vol. 125, No. 4, pp. 638-646 (2005).
Pan et al., "Discovery of NVP-LDE225, a potent and selective smoothened antagonist", ACS Med. Chem. Lett., vol. 1, No. 3, pp. 130-134 (2010).
Park and Park, "Differential expression of Runx2 and indian hedgehog in cartilaginous tumors", Pathol. Oncol. Res., vol. 13, No. 1, pp. 32-37 (2007).
Park et al., "A crucial requirement for hedgehog signaling in small cell lung cancer", Nature Med., Author manuscript, vol. 17, No. 11, pp. 1504-1508, DOI: 10.1038/nm.2473 (2012).
Paryzek et al., "Ammonium formate/palladium on carbon: A versatile system for catalytic hydrogen transfer reductions of carbon-carbon double bonds", Synthesis, No. 13, pp. 2023-2026 (2003).
Patil et al., "Hedgehog signaling in human hepatocellular carcinoma", Cancer Biol. Ther., vol. 5, No. 1, pp. 111-117 (2006).

(56) References Cited

OTHER PUBLICATIONS

Peacock et al., "Hedgehog signaling maintains a tumor stem cell compartment in multiple myeloma", PNAS USA, vol. 104, No. 10, pp. 4048-4053 (2007).
Peacock et al., "Visualization of Smoothened activation supports an essential role for hedgehog signaling in the regulation of self-renewal in small cell lung cancer", Infinity Pharmaceuticals, Inc., 1 page (2009).
Penova and Trandafiloff, "Intensification of extraction processes with tensides", Pharmazie, vol. 26, No. 8, pp. 489-490 (1971) With English Translation.
Philips et al., "Hedgehog signaling antagonist promotes regression of both liver fibrosis and hepatocellular carcinoma in a murine model of primary liver cancer", PLoS One, vol. 6, Issue 9, No. e23943, pp. 1-12 (2011).
Pietsch et al., "Medulloblastomas of the desmoplastic variant carry mutations of the human homologue of *Drosophila* patched", Cancer Research, vol. 57, pp. 2085-2088 (1997).
Pink et al., "Activity of IPI-926, a potent HH pathway inhibitor, in a novel model of medulloblastoma derived from Ptch/HIC +/− mice", Infinity Pharmaceuticals, Inc., AACR Meeting Abstracts Online, 99th AACR Annual Meeting, Apr. 13, 2008; San Diego, CA, Abstract #1588, Presentation Slides, 15 pages (2008).
Protor et al., "Hedgehog signaling in castration resistant prostate cancer", AACR Annual Meeting, Apr. 17-21, 2010, Infinity Pharmaceuticals, Inc., Abstract #3857, Presentation Slides, 14 pages (2010).
Qualthrough et al., "Hedgehog signalling in colorectal tumour cells: induction of apoptosis with cyclopamine treatment" Int. J. Cancer, vol. 110, No. 6, pp. 831-837 (2004).
Quirk et al., "The smoothened gene and hedgehog signal transduction in *Drosophila* and vertebrate development", Cold Spring Harbor Symposium Quant. Biol., vol. 62, pp. 217-226 (1997).
Rahman et al., "Alkaloids from veratrum album", Phytochemistry, vol. 30, No. 1, pp. 368-370 (1991).
Rahman and Choudhary, "Chemistry and biology of steroidal alkaloids", The Alkaloids, Cordell, et., Academic Press, San Diego, vol. 50, Ch. 2, pp. 61-108 (1998).
Rasmusson et al., "Azasteroids: structure-activity relationships for inhibition of $5\alpha$-reductase and of androgen receptor binding", J. Med. Chem., vol. 29, pp. 2298-2315 (1986).
Ravasio and Rossi, "Selective hydrogenations promoted by copper catalysts. 1. Chemoselectivity, regioselectivity, and stereoselectivity in the hydrogenation of 3-substituted steroids", J. Org. Chem., vol 56, No. 13, pp. 4329-4333 (1991).
Read, "Direct targeting of tumor cells with smoothed inhibitor IPI-926", 2011 AACR Read IPI-926 Direct Targeting, Infinity Pharmaceuticals, Inc., Presentation Slides, 27 pages (2011).
Reddy et al., "A new novel and practical one pot methodology for conversion of alchohols to amines", Synthetic Communications, vol. 30, No. 12, pp. 2233-2237 (2000).
Reetz and Li, "An efficient catalyst system for the asymmetric transfer hydrogenation of ketones: remarkably broad substrate scope", J. Am. Chem. Soc., vol. 128, No. 4, pp. 1044-1045 (2006).
Reifenberger et al., "Missense mutations in SMOH in sporadic basal cell carcinomas of the skin and primitive neuroectodermal tumors of the central nervous system", Cancer Research, vol. 58, pp. 1798-1803 (1998).
Remingtons Pharmaceutical Sciences, $17^{th}$ Edition, Gennaro, ed., Mack Publishing Company, Easton, Pennsylvania 18042, p. 1625 (1985).
Rohatgi et al., "Patched1 regulates hedgehog signaling at the primary cilium", Science, vol. 317, No. 5836, pp. 372-376 (2007).
Rominger et al., "Evidence for aliosteric interactions of antagonist binding to the smoothened receptor", J. Pharmacol. Exp. Ther., vol. 329, No. 3, pp. 995-1005 (2009).
Ross, "A Study Evaluating IPI-926 in combination with gemcitabine in patients with metastatic pancreatic cancer", National Cancer Institute, Clinical Trials (PDQ®), Data processed on Oct. 17, 2013, 3 pgs., Retrieved from the internet http://www.cancer.gov/clinicaltrials/search/view?cdrid=674592 &version=HealthProfessional.
Rubin and De Sauvage, "Targeting the hedgehog pathway in cancer", Nature Rev., vol. 5, No. 12, pp. 1026-1033 (2006).
Rudin et al., "Treatment of medulloblastoma with hedgehog pathway inhibitor GDC-0449", N. Eng. J. Med., vol. 361, No. 12, pp. 1173-1178 (2009).
Rudin et al., "A phase 1 study of IPI-926, an inhibitor of the hedgehog pathway, in patients with advanced or metastatic solid tumors", Infinity Pharmaceuticals, Inc., Poster, 1 page. (2010).
Saldanha, "The hedgehog signalling pathway and cancer", J. Pathol., vol. 193, No. 4, pp. 427-432 (2001).
Sanganwar and Gupta, "Dissolution-rate enhancement of fenofibrate by adsorption onto silica using supercritical carbon dioxide", Int. J. Pharm., vol. 360, No. 1-2, pp. 213-218 (2008).
Sasson et al., "Homogeneous catalytic transfer-hydrogenation of a, β-unsaturated carbonyl compounds by dichlorotris (triphenylphosphine) ruthenium (II)", Tetrahedron Letters, vol. 12, Issue. 24, pp. 2167-2170 (1971).
Sato et al., "Induction of the hair growth phase in postnatal mice by localized transient expression of Sonic hedgehog", J. Clin. Invest., vol. 104, No. 7, pp. 855-864 (1999).
Sato et al., "Effect of adenovirus-mediated expression of sonic hedgehog gene on hair regrowth in mice with chemotherapy-induced alopecia", J. Natl. Cancer Inst., vol. 93, No. 24, pp. 1858-1864 (2001).
Sawada et al., "Asymmetric catalysis of intramolecular cyclopropanation of 5-aryl-1-diazo-1-mesitylsulfonyl-5-hexen-2-ones", Adv. Synth. Catal., vol 347, Issue 11-13, pp. 1527-1532 (2005).
Shafaee et al., "Cyclopamine increases the cytotoxic effects of paclitaxel and radiation but not cisplatin and gemcitabine in hedgehog expressing pancreatic cancer cells", Cancer Chemother. Pharmacol., vol. 58, No. 6, pp. 765-770 (2006), Original Article, 6 pgs., DOI:10.1007/s00280-006-0227-4 (2006).
Shafiee et al., "Enzymatic deglycosylation of enfumafungin, a triterpene glycoside natural product, and its chemically synthesized analogues", J. Mol. Catalysis B: Enzymatic, vol. 16, pp. 27-32 (2001).
Shaw et al., "The sonic hedgehog pathway stimulates prostate tumor growth by paracrine signaling and recapitulates embryonic gene expression in tumor myofibroblasts", Oncogene, vol. 28, No. 50, pp. 4480-4490 (2009).
Sheng et al., "Activation of the hedgehog pathway in advanced prostate cancer", Molecular Cancer, vol 3, No. 29, 13 pages (2004).
Sheng et al., "Regulation of Gli1 localization by the cAMP/protein kinase A signaling axis through a site near the nuclear localization signal", J. Biol. Chem. vol 281, No. 1, pp. 9-12 (2006).
Shibasaki et al., "Hydrolysis of conjugated steroids by the combined use of β-glucuronidase preparations from Helix pomatia and Ampullaria: Determination of urinary cortisol and its metabolites", Steroids, vol. 66, pp. 795-801 (2001).
Shin et al., "Hedgehog / WNT feedback supports regenerative proliferation of epithelial stem cells in bladder", Nature, vol. 472, No. 7341, pp. 110-114, Author Manuscript, 15 pgs. (2011).
Shiotani et al., "Sonic hedgehog and CDX2 expression in the stomach", J. Gastroenterol. Hepatol., vol. 23, Suppl. 2, pp. S161-S166 (2008).
Shner et al., "The sterospecificity of the hydrogenation of $16\alpha$-methyl-3-oxo-$\Delta^4$-unsaturated compounds", Chemistry of Natural Compounds, vol. 6, No. 1 , pp. 48-51 (1970).
Shroff and Harper, "3-Aza-A-homoandrostenes" J. Med. Chem., vol. 12, No. 1, pp. 190-191 (1969).
Sicklick et al., "Hedgehog signaling correlates with hepatocellular carcinoma progression" J. Clinical Oncology, 2005 ASCO Annual Meeting Proceedings, vol. 23, No. 16s (June 1 Supplement), Abstract #9610, 1 page (2005).
Sicklick et al., "Hedgehog signaling maintains resident hepatic progenitors throughout life", Am. J. Physiol. Gastrointenst. Liver Physiol., vol. 290, No. 5, pp. G859-G870 (2006).

(56) References Cited

OTHER PUBLICATIONS

Sicklick et al., "Dysregulation of the hedgehog pathway in human hepatocarcinogenesis", Carcinogenesis, vol. 27, No. 4, pp. 748-757 (2006).
Sims-Mourtada et al., "Hedgehog: an attribute to tumor regrowth after chemoradiotherapy and a target to improve radiation response", Clin. Cancer Res., vol. 12, No. 21, pp. 6565-6572 (2006).
Singh et al., "Hedgehog-producing cancer cells respond to and require autocrine hedgehog activity", Cancer Res.; vol. 71, No. 13, pp. 4454-4463 (2011).
Siu et al., "A first-in-human, phase I study of an oral hedgehog (HH) pathway antagonist, BMS-833923 (XL 139), in subjects with advanced or metastatic solid tumors", J. Clin. Oncol., vol. 28, pp. 15s, Suppl. Abstract #2501, 3 pgs.(2010) Abstract Only.
Skipper et al., "In vivo efficacy of marimastat and chemoradiation in head and neck cancer xenografts", ORL, vol. 71, No. 1, pp. 1-5, Original Paper, DOI:10.1159/000163217 (2009).
Skvara et al., "Topical treatment of basal cell carcinomas in nevoid basal cell carcinoma syndrome with a smoothened inhibitor", J. Invest. Dermatol., vol. 131, No. 8, pp. 1735-1744 Original Article, DOI:10.1038/jid.2011.48 (2011).
Smith and Thomas, "Animal models for the study of squamous cell carcinoma of the upper aerodigestive tract: a historical perspective with review of their utility and limitations, Part A. Chemically-induced de novo cancer, syngeneic animal models of HNSCC, animal models of transplanted xenogeneic human tumors," Int., J. Cancer, vol. 118, No. 9, pp. 2111-2122 (2006).
Stanton et al., "Small-molecule modulators of the sonic hedgehog signaling pathway", Mol. Biosyst., vol. 6, pp. 44-54 (2010).
Stecca et al., "Melanomas require Hedgehog-GLI signaling regulated by interactions between GLI1 and the RAS-MEK/AKT pathways", PNAS, vol. 104, No. 14, pp. 5895-5900 (2007).
Steg et al., "Multiple gene expression analysis in paraffin-embedded tissues by TaqMan low-density array, application to hedgehog and Wnt pathway analysis in ovarian endometroid adenocarcinoma", J. Mol. Diagn., vol. 8, No. 1, pp. 76-83 (2006).
Suggs et al., "Facile homogeneous hydrogenations of hindered olefins with [ir(cod)py(PCy$_3$)]PF$_6$", Tetrahedron Letters, vol. 22, Issue 4, pp. 303-306 (1981).
Suginome et al., "Synthesis of O,N-diacetyl-3β-hydroxy-5α, 12α-jervan-11-one with 17-epi-configuration by hypoiodite reaction (1,2)", Tetrahedron Letters, vol. 14, No. 42, pp. 4147-4150 (1973).
Suginome et al., "Photo-induced Radical Rearrangements of Hypoiodite of N-Acetyljervine and the Related C-nor-D-Homosteroid in the Presence of Mercury (II) Oxide and Iodine", Bull. Chem. Soc. Japan, vol. 54, No. 10, pp. 3042-3047 (1981).
Suginome et al., "The transformation of Jervine into 18-Functional D-Homo-C-Norsteroids. IV. The Transformation of Jervine into (20R)-18,20-β-epoxy-3β-hydroxy-17β-ethyletiojervan-18-one 3-acetate via (20R)-18,20β-epoxy-3β-hydroxy-12α,17β-ethyletiojervan-11-one 3-acetate", Bull. Chem. Soc. Jpn., vol. 54, No. 3, pp. 852-861 (1981).
Sydor et al., "Activity of IPI-926, a novel inhibitor of the HH pathway, in subcutaneous and orthotopically implanted xenograft tumors that express SHH ligand", Eur. J. Cancer, Supplement, vol. 6, No. 12, p. 179, Poster 570 (2008).
Taipale et al., "Effects of oncogenic mutations in smoothened and patched can be reversed by cyclopamine", Nature, vol. 406, No. 6799, pp. 1005-1009 (2000).
Tannock et al., "Docetaxel plus prednisone or mitoxantrone plus prednisone for advanced prostate cancer", N. Engl. J. Med., vol. 351, No. 15, pp. 1502-1512 (2004).
Tas and Avci, "Rapid clearance of psoriatic skin lesions induced by topical cyclopamine", Dermatology, vol. 209 pp. 126-131 (2004).
Thayer et al., "Hedgehog is an early and late mediator of pancreatic cancer tumorigenesis", Nature, vol. 425, pp. 851-856 (2003).
Thievessen et al., "J. Hedgehog signaling in normal urothelial cells and urothelial carcinoma cell lines", J. Cell Physiol., vol. 203, No. 2, pp. 372-377 (2005) Abstract Only.

Travaglione et al., "Activity of IPI-926, a novel inhibitor of the Hh pathway, in subcutaneous and orthotopically implanted xenograft tumors that express SHh ligand", Infinity Pharmaceuticals, Inc., Presentation Poster, 1 page (2008).
Travaglione et al., "A novel HH pathway inhibitor, IPI-926, delays recurrence post-chemotherapy in a primary human SCLC xenograft model", AACR Meeting Abstracts Online, 99$^{th}$ AACR Annual Meeting, Apr. 12-16, 2008, San Diego, CA, Abstract #4611, 2 pags (2008).
Travaglione et al., "Induction of tumor-derived hedgehog ligand by chemotherapy", Infinity Pharmaceuticals, Inc., Presentation Poster, Abstract #323, 1 page (2009).
Travaglione et al., "The Hh inhibitor IPI-926 enhances tumor perfusion and nab-paclitaxel activity in a pancreatic xenograft model", Infinity Pharmaceuticals, Inc., Presentation Poster, Abstract #LB-374, 1 page (2010).
Tremblay et al., "Synthesis of novel, chemically stable D-homo-cyclopamine analogs via a cyclopropanation/ring-expansion sequence", Infinity Pharmaceuticals, Inc., 1 page (2007).
Tremblay et al., "Semisynthetic cyclopamine analogues as potent and orally bioavailable hedgehog pathway antagonists", J. Med. Chem., vol. 51, No. 21, pp. 6646-6649 (2008).
Tremblay et al., "Synthesis and structure activity relationship of D-homo cyclopamine analogs: 3-substituted analogs", Infinity Pharmaceuticals, Inc., Presentation Poster, 1 page (2009).
Tremblay et al., "Discovery of IPI-926, a semi-synthetic clinical candidate that targets the hedgehog pathway", Infinity Pharmaceuticals, ACS Meeting Salt Lake City, UT on Mar. 25, 2009, Presentation Slides, 26 pages (2009).
Tremblay et al., "Discovery of a potent and orally active hedgehog pathway antagonist (IPI-926)", J. Med. Chem., vol. 52, No. 14, pp. 4400-4418 (2009).
Tremblay et al., "Recent patents for hedgehog pathway inhibitors for the treatment of malignancy", Expert Opin. Ther. Pat., vol. 19, No. 8, pp. 1039-1056 (2009).
Tremblay et al., "New Developments in the discovery of small molecule Hedgehog pathway antagonists", Curr. Opin. Chem. Biol., vol. 14, No. 3, pp. 428-435 (2010) Article in press, COCHBI-737, vol. 14, pp. 1-8 (2010).
Tremblay et al., "Development of multi-kilogram synthetic route to IPI-926, a novel hedgehog pathway antagonistic for the treament of malignant diseases", Infinity Pharmaceuticals, Inc., Apr. 2, 2011, Presentation Slides, 29 pages (2011).
Tsuji et al., "Highly stereoselective hydrogenation of 3-oxo4-ene and -1,4-diene steroids to 5β compounds with palladium catalyst", J. Org. Chem., vol. 45, pp. 2729-2731 (1980).
Turner et al., "Sonic hedgehog pathway inhibition alters epididymal function as assessed by the development of sperm motility", Journal of Andrology, vol. 27, No. 2, pp. 225-232 (2006).
Van Der Horst et al., "Hedgehog stimulates only osteoblastic differentiation of undifferentiated KS483 cells", Bone, vol. 33, No. 6, pp. 899-910 (2003).
Vanhook, "Focus issue: fine-tuning hedgehog signaling in development and disease", Sci. Signaling, vol. 4, Issue 200, No. eg10, pp. 1-2 (2011).
Van Weerden et al., "Human xenograft models as useful tools to assess the potential of novel therapeutics in prostate cancer", Br. J. Cancer, vol. 100, No. 1, pp. 13-18 (2009).
Veratrum nigrum, Wikipedia entry last updated Apr. 23, 2014, Retrieved from the internet http://en.wikipedia.org/wiki/Veratrum_nigram.
Villavicencio et al., "The sonic hedgehog-patched-gli pathway in human development and disease", Am. J. Hum. Genet., vol. 67, No. 5, pp. 1047-1054 (2000).
Villavicencio et al., "Activity of the Hh pathway inhibitor IPI-926 in a mouse model of medulloblastoma", Infinity Pharmaceuticals, Inc., Abstract #3199, Presentation Poster, 1 page (2009).
Voituriez and Charette, "Enantioselective cyclopropanation with TADDOL-derived phosphate ligands", Adv. Synth. Catal., vol. 348, Issue 16-17, pp. 2363-2370 (2006).
Von Hoff et al., "Inhibition of the hedgehog pathway in advanced basal-cell carcinoma", N. Eng. J. Med., vol. 361, No. 12, pp. 1164-1172 (2009).

(56) References Cited

OTHER PUBLICATIONS

Wang et al., "Revision of structure of peimisine", Yao Xue Xue Bao, vol. 17, No. 4, pp. 273-278 (1992) Database Accession No. 1992:490583, (1992).

Wanshura et al., "Sequential activation of snail1 and N-Myc modulates sonic hedgehog-induced transformation of neural cells", Cancer Res.; vol. 71, No. 15, pp. 5336-5345 (2011).

Warzecha et al., "Inhibition of osteosarcoma cell proliferation by the hedgehog-inhibitor cyclopamine", J. Chemother., vol. 19, No. 5, pp. 554-561 (2007).

Watkins et al., "Hedgehog signaling within airway epithelial progenitors and in small-cell lung cancer", Nature, vol. 422, pp. 313-317 (2003).

Wei et al., "Indian hedgehog and its targets in human endometrium: menstrual cycle expression and response to CDB-2914", J. Clin. Endocrinol. Metab., vol. 95, No. 12, pp. 5330-5337 (2010).

Williams et al., "Identification of a small molecule inhibitor of the hedgehog signaling pathway: effects on basal cell carcinoma-like lesions", PNAS USA, vol. 100, No. 8, pp. 4616-4621 (2003).

Wintersteiner et al., "Structure of jervine, V. The sulfuric acid-catalyzed acetolysis of diacetyltetrahydrojervine", J. Am. Chem. Soc., vol. 76, No. 22, pp. 5609-5616 (1954) Database Accession No. 1955:73588 (1954).

Wong et al., "Primary cilia can both mediate and suppress Hedgehog pathway-dependent tumorigenesis", Nat. Med., vol. 15, No. 9, pp. 1055-1061 (2009).

Wu et al., "Chemical constituent of hubeibeimu, V. Isolation and identification of hupehenisine", Yaoxue Xuebao, vol. 21, No. 7, pp. 546-550 (1986) Database Accession No. 1987:15699 (1987).

Wunder et al., "Opportunities for improving the therapeutic ratio for patients with sarcoma", Lancet Oncol., vol. 8, No. 6, pp. 513-524 (2007).

Xie et al., "Activating smoothened mutations in sporadic basal-cell carcinoma", Nature, vol. 391, pp. 90-92 (1998).

Yamakawa et al., "CH/$\pi$ attraction: the origin of enantioselectivity in transfer hydrogenation of aromatic carbonyl compounds catalyzed by chiral $\eta^6$-arene-ruthenium(II) complexes", Angew. Chem. Int. Ed., vol. 40, No. 15, pp. 2818-2821 (2001).

Yang and Hinds, "pRb-mediated control epithelial cell proliferation and Indian Hedgehog expression in mouse intestinal development", BMC Developmental Biology, vol. 7, No. 6, pp. 1-12 (2007).

Yauch et al., "Smoothened mutation confers resistance to a hedgehog pathway inhibitor in medulloblastoma", Science, vol. 326, No. 5952, pp. 572-574 (2009).

Yoo et al., "Sonic hedgehog signaling promotes motility and invasiveness of gastric cancer cells through TGF-$\beta$-mediated activation of the ALK5-smad 3 pathway", Carcinogenesis, vol. 29, No. 3 pp. 480-490 (2008).

Yoshizaki et al., "Expressions of sonic hedgehog, patched, smoothened and Gli-1 in human intestinal stromal tumors and their correlation with prognosis", World J. Gastroenterol., vol. 12, No. 35, pp. 5687-5691 (2006).

Yu et al., "Chemical constituents of the unibract fritillary (*Fritillaria unibracteata*)", Zhongcaoyao, vol. 21, No. 1, pp. 2-6 (1990), Database Accession No. 1990:512481 (1990).

Yun et al., "Simultaneous synthesis of enantiomerically pure (R)-1-phenylethanol and (R)-$\alpha$-methylbenzylamine from racemic $\alpha$-methylbenzylamine using $\omega$-transaminase/alcohol dehydrogenase/glucose dehydrogenase coupling reaction", Biotechnol. Lett., vol. 25, No. 10, pp. 809-814 (2003).

Yun et al., "$\omega$-Amino acid: Pyruvate transaminase from Alcaligenes denitrificans Y2k-2: A new catalyst for kinetic resolution of $\beta$-amino acids and amines", Appl. Environ. Microbiol., vol. 70, No. 4, pp. 2529-2534 (2004).

Zanotti-Gerosa et al., "Ruthenium-catalysed asymmetric reduction of ketones, diphosphine ligands in hydrogenations for pharmaceutical synthesis", Platinum Metals Rev., vol. 49, No. 4, pp. 158-165 (2005).

Zassoinovich et al., "Asymmetric hydrogen transfer reactions promoted by homogeneous transition metal catalysts", Chem. Rev., vol. 92, No. 5, pp. 1051-1069 (1992).

Zeisberg and Neilson, "Biomarkers for epithelial-mesenchymal transitions", J. Clin. Invest., vol. 119, No. 6, pp. 1429-1437 (2009).

Zeng et al., "Neurosteroid analogues. 10. The effect of methyl group substitution of the C-6 and C7 positions on the GABA modulatory and anesthetic actions of ($3\alpha,5\alpha$)- and ($3\alpha,5\beta$)-3-hydroxypregnan-20-one", J. Med. Chem., vol. 48, No. 8, pp. 3051-3059 (2005).

Zhang et al., "Hedgehog pathway responsivenss correlates with the presence of primary cilia on prostate stromal cells", BMC Developmental Biology, vol. 9, No. 50, pp. 1-7 (2009).

Zhao et al., "Studies on the constituents of veratrum plants II. Constituents of *Veratrum nigrum* L. var. *ussuriense* (1). Structure and $^1$H- and $^{13}$C-nuclear magnetic resonance spectra of a new alkaloid, verussurinine, and related alkaloid", Chem. Pharm. Bull., vol. 39, No. 3, 549-554 (1991).

Zhao et al., "Hedgehog signaling is essential for maintenance of cancer stem cells in myeloid leukaemia", Nature, vol. 460, No. 7255, pp. 652-656 (2009) Pre-Publication Article DOI: 10.1038/nature07737, pp. 1-5 (2009).

International Search Report from International Patent Application No. PCT/US2016/035713, 8 pages, dated Nov. 9, 2016.

International Search Report from International Patent Application No. PCT/US2017/017247, 7 pages, dated Apr. 25, 2017.

Peluso et al., "Impact of the Smoothened inhibitor, IPI-926, on smoothened ciliary localization and Hedgehog pathway activity", PLOS ONE, vol. 9, Issue 3, No. e90534, 11 pages (2014).

\* cited by examiner

ENZYMATIC TRANSAMINATION OF CYCLOPAMINE ANALOGS

This application is a continuation of U.S. application Ser. No. 14/257,658, filed Apr. 21, 2014, now abandoned which is a continuation of U.S. application Ser. No. 13/175,053, filed Jul. 1, 2011, now U.S. Pat. No. 8,703,448, which is a continuation of International Application No. PCT/US2010/044597, filed Aug. 5, 2010, which claims the benefit of U.S. Provisional Application No. 61/231,439, filed on Aug. 5, 2009, each of which is incorporated herein by reference in its entirety.

BACKGROUND

Cyclopamine, a natural product isolated from *Veratrum californicum*, has emerged as a significant pharmacological tool to validate the Hedgehog (Hh) pathway in cancer. Cyclopamine directly acts on SMO and inhibits tumor growth in several murine models of pancreatic, medulloblastoma, prostate, small cell lung, and digestive tract cancers. However, the clinical development of cyclopamine as a therapeutic in cancer is hampered by its poor solubility, acid sensitivity, and weak potency relative to other reported small-molecule Hh antagonists.

There has been considerable focus on the development of novel cyclopamine analogues with improved potency, and improved pharmacokinetic and pharmaceutical properties relative to cyclopamine (s ee, for example, U.S. Pat. Nos. 7,230,004 and 7,407,967, incorporated herein by reference). From that effort, a seven-membered D-ring sulfonamide analogue of cyclopamine, IPI-926, emerged as a clinical development candidate (see Tremblay et al., "Discovery of a Potent and Orally Active Hedgehog Pathway Antagonist (IPI-926)" *J. Med. Chem.* (2009) 52:4400-4418, incorporated herein by reference). Large quantities of IPI-926 are required for clinical development. Moreover, other promising amino analogues can be synthesized following routes similar to that used to generate IPI-926.

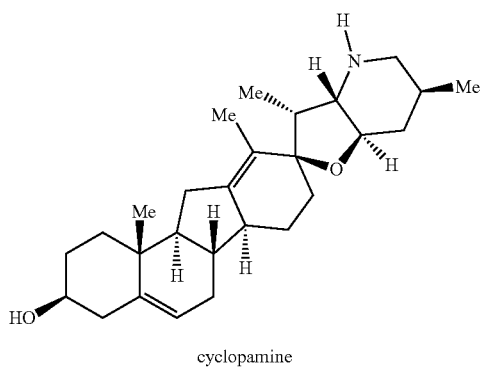

cyclopamine

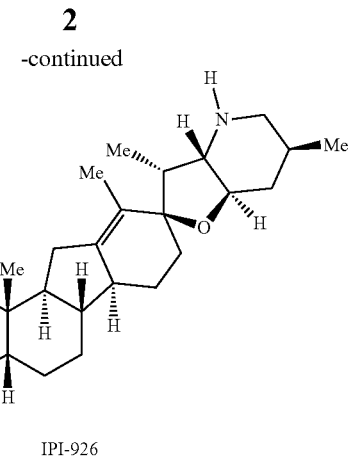

IPI-926

SUMMARY

Provided are novel processes for the synthesis of amino analogues, such as IPI-926, from ketone starting materials.

For example, in one aspect, provided is a process for preparing a compound of formula (II):

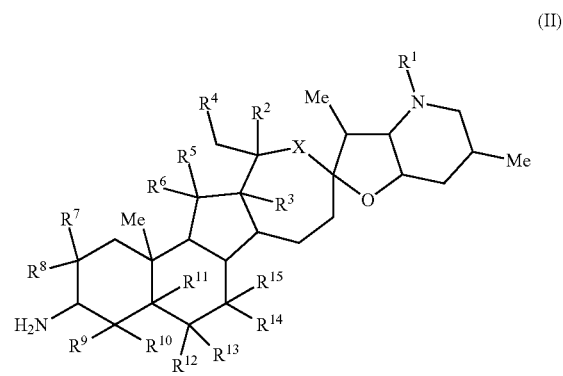

or a salt thereof;
from a compound of formula (I):

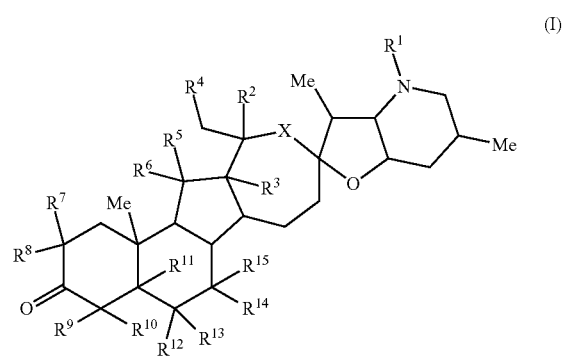

or a salt thereof;
wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and X are as defined herein,
the process comprising contacting a compound of formula (I) or a salt thereof, an amino donor molecule, and an amine transaminase enzyme in a solution to provide a compound of formula (II) or a salt thereof.

In certain embodiments, the process further comprises adding a co-factor to the solution.

In certain embodiments, the co-factor is pyridoxal phosphate (PLP).

In certain embodiments, the co-factor is a co-enzyme. In certain embodiments, the co-enzyme is selected from L-alanine dehydrogenase (LADH), lactate dehydrogenase (LDH), nicotinamide adenine dinucleotide phosphate (NADPH), nicotinamide adenine dinucleotide (NAD), formate dehydrogenase (FDH), and glucose dehydrogenase (GDH).

In certain embodiments, process further comprises adding a pyruvate reductase mix to the solution. As used herein, the term "pyruvate reductase mix" refers to a combination that includes an enzyme that is capable of mediating the reduction of pyruvate and one or more (e.g., 1, 2, 3, 4, 5, or 6, e.g., 2, 3 or 4, e.g., 2 or 3) additional agents (e.g., an enzyme, a co-enzyme or co-factor, a reducing agent as well as combinations thereof).

In embodiments, the enzyme that is capable of mediating the reduction of pyruvate is LDH.

In embodiments, the combination includes an agent (e.g., an enzyme) that is capable of regenerating a co-enzyme or co-factor that mediates pyruvate reduction. In certain embodiments, the combination can include an enzyme that is capable of regenerating NADPH. Such enzymes can include, without limitation, GDH and FDH.

In embodiments, the combination includes a reducing agent. Reducing agents can include, without limitation, glucose or formate.

In embodiments, the combination includes a co-enzyme or co-factor. Co-enzymes or co-factors can include, without limitation, NAD.

In embodiments, the combination includes an agent (e.g., an enzyme) that is capable of regenerating a co-enzyme or co-factor that mediates pyruvate reduction as defined anywhere herein; and one or more additional agents (e.g., 2 or 3 additional agents). For example, the combination can include an agent (e.g., an enzyme) that is capable of regenerating a co-enzyme or co-factor that mediates pyruvate reduction as defined anywhere herein; and one or both of the following: a reducing agent and a co-enzyme or co-factor.

In embodiments, a pyruvate reductase mix includes LDH, an agent (e.g., an enzyme) that is capable of regenerating a co-enzyme or co-factor that mediates pyruvate reduction as defined anywhere herein; and one or more additional agents (e.g., 2 or 3 additional agents); e.g., one or both of the following: a reducing agent and a co-enzyme or co-factor. For example, a pyruvate reductase mix can include LDH, GDH, and glucose and can further include NAD, e.g., PRM-102 (Codexis), which includes LDH, GDH, glucose, and $NAD^+$. As another example, a pyruvate reductase mix can include LDH, FDH, and formate and can further include NAD.

In certain embodiments, when pyruvate is generated during the course of the processes described herein, the pyruvate can be removed, chemically converted to another product and optionally further removed; or recycled (or combinations thereof). Methods describing such operations are described in, e.g., Koszelewski, D., et al., *Trends in Biotechnology* 2010, 28, 324-332, which is incorporated herein by reference in its entirety.

In certain embodiments, the enzyme preferentially generates a compound of formula (II), or a salt thereof, wherein the newly-formed amino group has (R) or (S) stereochemistry.

In certain embodiments, the enzyme is an omega amine transaminase, a broad-range transaminase, a glutamate-pyruvate transaminase or a glutamate-oxaloacetic transaminase.

In certain embodiments, the enzyme is an omega amine transaminase.

In certain embodiments, the omega amine transaminase is selected from the group consisting of ATA-101, ATA-102, ATA-103, ATA-104, ATA-105, ATA-106, ATA-107, ATA-108, ATA-109, ATA-110, ATA-113, ATA-114, ATA-115, ATA-116, ATA-117, ATA-124, an omega amine transaminase from *Chromobacterium violaceum*, an omega amine transaminase from *Alcaligenes denitrificans*, an omega amine transaminase from *Arthrobactercitreus*, an omega amine transaminase from *Klebsiella pneumoniae*, an omega amine transaminase from *Bacillus thuringiensis*, an omega amine transaminase from *Bacillus cereus*, and an omega amine transaminase from *Vibrio fluvialis*.

In certain embodiments, the amino donor molecule is an amine or a salt thereof. In certain embodiments, the amine is selected from pyridoxamine, methylbenzylamine, 2-aminobutane, propyl amine, isopropyl amine, 1,1,1-trifluoropropan-2-amine, 1,1,1,3,3,3-hexafluoropropan-2-amine, benzyl amine, 2-amino-1-butanol, 1-amino-1-phenylethane, 1-amino-1-(2-methoxy-5-fluorophenyl)ethane, 1-amino-1-phenylpropane, 1-amino-1-(4hydroxyphenyl)propane, 1-amino-1-(4-bromophenyl)propane, 1-amino-1-(4-nitrophenyl)propane, 1-phenyl-2-aminopropane, 1-(3-trifluoromethylphenyl)-2-aminopropane, 2-aminopropanol, 1-amino-1-phenylbutane, 1-phenyl-2-aminobutane, 1-(2,5-dimethoxy-4-methylphenyl)-2-aminobutane, 1-phenyl-3-aminobutane, 1-(4-hydroxyphenyl)-3-aminobutane, 1-amino-1-(2-naphthyl)ethane, cis-2-methylcyclopentanamine, trans-2-methylcyclopentanamine, cis-3-methylcyclopentanamine, trans-3-methylcyclopentanamine, cis-2-ethylcyclopentanamine, trans-2-ethylcyclopentanamine, cis-3-ethylcyclopentanamine, trans-3-ethylcyclopentanamine, cis-2-methylcyclohexanamine, trans-2-methylcyclohexanamine, cis-3-methylcyclohexanamine, trans-3-methylcyclohexanamine, cis-2-ethylcyclohexanamine, trans-2-ethylcyclohexanamine, cis-3-ethylcyclohexanamine, trans-3-ethylcyclohexanamine, 1-aminotetralin, 2-aminotetralin, 2-amino-5-methoxytetralin, 1-aminoindane, 2-aminoindane, 2-amino-1-propanol, cis-1-amino-2-indanol, trans-1-amino-2-indanol, 1-amino-6-hydroxyindanamine, taurine, or a salt thereof.

In certain embodiments, the amino donor molecule is a chiral amino donor molecule. In certain embodiments, the chiral amino donor molecule is a chiral amine or salt thereof, e.g., an amine containing at least one asymmetric center. Exemplary chiral amines include, but are not limited to, (R)-methylbenzylamine, (S)-methylbenzylamine, (S)-2-aminobutane, (R)-2-aminobutane, (S)-1-aminoindane, (R)-1-aminoindane, (R)-1,1,1-trifluoropropan-2-amine, (S)-1,1,1-trifluoropropan-2-amine, (R)-2-amino-1-propanol, (S)-2-amino-1-propanol, (1R,2S)-cis-1-amino-2-indanol, (1R,2R)-trans-1-amino-2-indanol, 1-(R)-amino-6-hydroxyindanamine, 1-(S)-amino-6-hydroxyindanamine, (R)-2-amino-1-butanol, (S)-2-amino-1-butanol, (R)-1-amino-1-phenylethane, (S)-1-amino-1-phenylethane, (R)-1-amino-1-(2-methoxy-5-fluorophenyl)ethane, (S)-1-amino-1-(2-methoxy-5-fluorophenyl)ethane, (R)-1-amino-1-phenylpropane, (S)-1-amino-1-phenylpropane, (R)-1-amino-1-(4-hydroxyphenyl)-propane, (S)-1-amino-1-(4-hydroxyphenyl)-propane, (R)-1-amino-1-(4-bromophenyl)propane, (S)-1-amino-1-(4-bromophenyl)propane, (R)-1-amino-1-(4-nitrophenyl)propane, (S)-1-amino-1-(4- nitrophenyl)propane, (R)-1-phenyl-2-aminopropane, (S)-1-phenyl-2-aminopropane, (R)-1-(3-trifluoromethylphenyl)-2-aminopropane, (S)-1-(3-trifluoromethylphenyl)-2-aminopropane (R)-1-amino-1-phenylbutane, (S)-1-amino-1-phenylbutane, (R)-1-phenyl-2-aminobutane, (S)-1-phenyl-2-aminobutane, (R)-1-(2,5-di-methoxy-4-methylphenyl)-2-aminobutane, (S)-1-(2,5-di-methoxy-4-methylphenyl)-2-aminobutane, (R)-1-phenyl-3-aminobutane, (S)-1-phenyl-3-aminobutane, (R)-1-(4-hydroxyphenyl)-3-aminobutane, (S)-1-(4-hydroxyphenyl)-3-aminobutane, (R)-1-amino-1-(2-naphthyl)ethane, (S)-1-amino-1-(2-naphthyl)ethane (R)-1-aminotetralin, (S)-1-aminotetralin, (R)-2-aminotetralin, (S)-2-aminotetralin, (R)-2-amino-5-methoxytetralin, (S)-2-amino-5-methoxytetralin, (1R,2S)-cis-2-methylcyclopentanamine, (1S,2R)-cis-2-methylcyclopentanamine, (1R,2R)-trans-2-methylcyclopentanamine, (1S,2S)-trans-2-methylcyclopentanamine, (1R,3S)-cis-3-methylcyclopentanamine, (1S,3R)-cis-3-methylcyclopentanamine, (1R,3R)-trans-3-methylcyclopentanamine, (1S,3S)-trans-3-methylcyclopentanamine, (1R,2S)-cis-2-ethylcyclopentanamine, (1S,2R)-cis-2-ethylcyclopentanamine, (1R,2R)-trans-2-ethylcyclopentanamine, (1S,2S)-trans-2-ethylcyclopentanamine, (1R,3S)-cis-3-ethylcyclopentanamine, (1S,3R)-cis-3-ethylcyclopentanamine, (1R,3R)-trans-3-ethylcyclopentanamine, (1S,3S)-trans-3-ethylcyclopentanamine, (1R,2S)-cis-2-methylcyclohexanamine, (1S,2R)-cis-2-methylcyclohexanamine, (1R,2R)-trans-2-methylcyclohexanamine, (1S,2S)-trans-2-methylcyclohexanamine, (1R,3S)-cis-3-methylcyclohexanamine, (1S,3R)-cis-3-methylcyclohexanamine, (1R,3R)-trans-3-methylcyclohexanamine, (1S,3S)-trans-3-methylcyclohexanamine, (1R,2S)-cis-2-ethylcyclohexanamine, (1S,2R)-cis-2-ethylcyclohexanamine, (1R,2R)-trans-2-ethylcyclohexanamine, (1S,2S)-trans-2-ethylcyclohexanamine, (1R,3S)-cis-3-ethylcyclohexanamine, (1S,3R)-cis-3-ethylcyclohexanamine, (1R,3R)-trans-3-ethylcyclohexanamine, (1S,3S)-trans-3-ethylcyclohexanamine, or a salt thereof.

In certain embodiments, the amino donor molecule is an amino acid or a polypeptide thereof and/or salt thereof. In certain embodiments, the amino acid is selected from glycine, alanine, aspartic acid, phenylalanine, 2-aminopentanedioic acid, 3-aminobutyrate, γ-aminobutyrate, β-alanine, asparagine, cysteine, glutamic acid, glutamine, proline, selenocysteine, serine, tyrosine, arginine, histidine, ornithine, isoleucine, leucine, lysine, methionine, threonine, tryptophan, valine, and polypeptides thereof and/or salts thereof.

In certain embodiments, the chiral amino donor molecule is a chiral amino acid or a polypeptide thereof and/or a salt thereof, e.g., containing at least one asymmetric center. Exemplary chiral amino acids include, but are not limited to, (L)-alanine, (D)-alanine, (L)-aspartic acid, (D)-aspartic acid, (L)-phenylalanine, (D)-phenylalanine, (2S)-2-aminopentanedioic acid, (L)-asparagine, (D)-asparagine, (L)-cysteine, (D)-cysteine, (L)-glutamine, (D)-glutamine, (L)-glutamic acid, (D)-glutamic acid, (L)-proline, (D)-proline, (L)-selenocysteine, (D)-selenocysteine, (L)-serine, (D)-serine, (L)-tyrosine, (D)-tyrosine, (L)-arginine, (D)-arginine, (L)-histidine, (D)-histidine, (L)-isoleucine, (D)-isoleucine, (L)-leucine, (D)-leucine, (L)-lysine, (D)-lysine, (L)-methionine, (D)-methionine, (L)-threonine, (D)-threonine, (L)-tryptophan, (D)-tryptophan, (L)-valine, (D)-valine, (L)-ornithine, (D)-ornithine, (3R)-aminobutyrate, (3S)-aminobutyrate and polypeptides thereof and/or salts thereof.

In certain embodiments, the solution is a buffered solution. In certain embodiments, the buffered solution is a sodium phosphate buffered solution.

In certain embodiments, the pH of the solution is between about 5 and about 9, between about 5 and about 8, between about 6 and about 8, between about 7 and about 8, between about 7 and about 7.5, or between about 7.5 and about 8.

In certain embodiments, the pH is of the solution is less than about 9, less than about 8.5, or less than about 8. In certain embodiments, the pH of the solution is about 7. In certain embodiments, the pH of the solution is about 7.5. In certain embodiments, the pH of the solution is about 8.

In certain embodiments, the compound of formula (I) or a salt thereof and a compound of formula (II) or a salt thereof are selected from any set of compounds provided in Tables 1, 2, 3, 4 or 5.

In certain embodiments, the process further comprises contacting a compound of formula (II) or a salt thereof with a sulfonylating agent to provide a compound of formula (III):

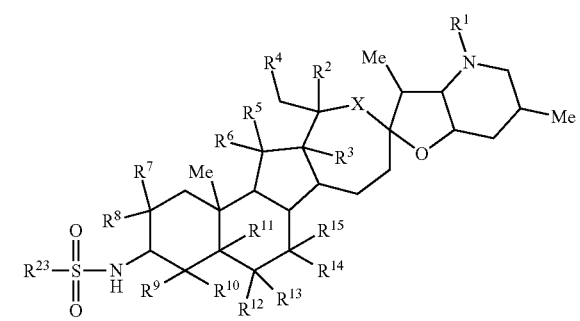

or a salt thereof,
wherein $R^{23}$ is alkyl or aryl.

In certain embodiments, the sulfonylating agent is selected from benzenesulfonyl chloride, benzenesulfonyl anhydride, p-toluenesulfonyl chloride, p-toluenesulfonyl anhydride, methanesulfonyl chloride, and methanesulfonyl anhydride. In certain embodiments, the sulfonylating agent is methanesulfonyl chloride or methanesulfonyl anhydride, and $R^{23}$ is —$CH_3$.

The details of additional or alternative embodiments are set forth in the accompanying Detailed Description and Examples as described below. Other features, objects, and advantages of the invention will be apparent from this description and from the claims.

Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987, each of which is incorporated herein by reference.

Certain compounds of the present invention comprise one or more asymmetric centers, and thus can exist in various isomeric forms, e.g., enantiomers and/or diastereomers. The compounds provided herein can be in the form of an individual enantiomer, diastereomer or geometric isomer, or can be in the form of a mixture of stereoisomers, including racemic mixtures and mixtures enriched in one or more stereoisomer. In certain embodiments, the compounds of the invention are enantiopure compounds. In certain other embodiments, mixtures of stereoisomers are provided.

Furthermore, certain compounds, as described herein may have one or more double bonds that can exist as either the cis or trans, or the E or Z isomer, unless otherwise indicated. The invention additionally encompasses the compounds as individual isomers substantially free of other isomers, and alternatively, as mixtures of various isomers, e.g., racemic mixtures of E/Z isomers or mixtures enriched in one E/Z isomer.

The terms "enantiomerically enriched," "enantiomerically pure" and "non-racemic," as used interchangeably herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, more preferably at least 75% by weight, and even more preferably at least 80% by weight. In some embodiments, the enrichment can be much greater than 80% by weight, providing a "substantially enantiomerically enriched," "substantially enantiomerically pure" or a "substantially non-racemic" preparation, which refers to preparations of compositions which have at least 85% by weight of one enantiomer relative to other enantiomer, more preferably at least 90% by weight, and even more preferably at least 95% by weight. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., Enantiomers, Racemates and Resolutions (Wiley Interscience, New York, 1981); Wilen, S. H., et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972), each of which is incorporated herein by reference.

Carbon atoms, unless otherwise specified, may optionally be substituted with one or more substituents. The number of substituents is typically limited by the number of available valences on the carbon atom, and may be substituted by replacement of one or more of the hydrogen atoms that would be available on the unsubstituted group. Suitable substituents are known in the art and include, but are not limited to, alkyl, alkenyl, alkynyl, alkoxy, alkoxy, alkylthio, aryl, aryloxy, arylthio, aralkyl, heteroaryl, heteroaralkyl, cycloalkyl, heterocyclyl, halo, azido, hydroxyl, thio, amino, nitro, nitrile, imido, amido, carboxylic acid, aldehyde, carbonyl, ester, silyl, haloalkyl, haloalkoxy (e.g., perfluoroalkoxy such as $-OCF_3$), $=O$, $=S$, and the like.

When a range of values is listed, it is intended to encompass each value and sub-range within the range. For example, an alkyl group containing 1-6 carbon atoms ($C_{1-6}$ alkyl) is intended to encompass, $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

The term "alkyl," as used herein, refers to saturated, straight- or branched-chain hydrocarbon radical containing between one and thirty carbon atoms. In certain embodiments, the alkyl group contains 1-20 carbon atoms. Alkyl groups, unless otherwise specified, may optionally be substituted with one or more substituents. In certain embodiments, the alkyl group contains 1-10 carbon atoms. In certain embodiments, the alkyl group contains 1-6 carbon atoms. In certain embodiments, the alkyl group contains 1-5 carbon atoms. In certain embodiments, the alkyl group contains 1-4 carbon atoms. In certain embodiments, the alkyl group contains 1-3 carbon atoms. In certain embodiments, the alkyl group contains 1-2 carbon atoms. In certain embodiments, the alkyl group contains 1 carbon atom. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a straight- or branched-chain hydrocarbon radical having at least one carbon-carbon double bond by the removal of a single hydrogen atom, and containing between two and thirty carbon atoms. Alkenyl groups, unless otherwise specified, may optionally be substituted with one or more substituents. In certain embodiments, the alkenyl group contains 2-20 carbon atoms. In certain embodiments, the alkenyl group contains 2-10 carbon atoms. In certain embodiments, the alkenyl group contains 2-6 carbon atoms. In certain embodiments, the alkenyl group contains 2-5 carbon atoms. In certain embodiments, the alkenyl group contains 2-4 carbon atoms. In certain embodiment, the alkenyl group contains 2-3 carbon atoms. In certain embodiments, the alkenyl group contains 2 carbon atoms. Alkenyl groups include, for example, ethenyl, propenyl, butenyl, 1-methyl-2-buten-1-yl, and the like.

The term "alkynyl," as used herein, denotes a straight- or branched-chain hydrocarbon radical having at least one carbon-carbon triple bond by the removal of a single hydrogen atom, and containing between two and thirty carbon atoms. Alkynyl groups, unless otherwise specified, may optionally be substituted with one or more substituents. In certain embodiments, the alkynyl group contains 2-20 carbon atoms. In certain embodiments, the alkynyl group contains 2-10 carbon atoms. In certain embodiments, the alkynyl group contains 2-6 carbon atoms. In certain embodiments, the alkynyl group contains 2-5 carbon atoms. In certain embodiments, the alkynyl group contains 2-4 carbon atoms. In certain embodiments, the alkynyl group contains 2-3 carbon atoms. In certain embodiments, the alkynyl group contains 2 carbon atoms. Representative alkynyl groups include, but are not limited to, ethynyl, 2-propynyl (propargyl), 1-propynyl, and the like.

The terms "cycloalkyl", used alone or as part of a larger moiety, refer to a saturated monocyclic or bicyclic hydrocarbon ring system having from 3-15 carbon ring members. Cycloalkyl groups, unless otherwise specified, may optionally be substituted with one or more substituents. In certain embodiments, cycloalkyl groups contain 3-10 carbon ring members. In certain embodiments, cycloalkyl groups contain 3-9 carbon ring members. In certain embodiments, cycloalkyl groups contain 3-8 carbon ring members. In certain embodiments, cycloalkyl groups contain 3-7 carbon ring members. In certain embodiments, cycloalkyl groups contain 3-6 carbon ring members. In certain embodiments, cycloalkyl groups contain 3-5 carbon ring members. Cycloalkyl groups include, without limitation, cyclopropyl, cyclobutyl, cyclopentyl, cyclohexyl, cycloheptyl, and cyclooctyl. The term "cycloalkyl" also includes saturated hydrocarbon ring systems that are fused to one or more aryl or heteroaryl rings, such as decahydronaphthyl or tetrahydronaphthyl, where the point of attachment is on the saturated hydrocarbon ring.

The term "aryl" used alone or as part of a larger moiety (as in "aralkyl"), refers to an aromatic monocyclic and bicyclic hydrocarbon ring system having a total of 6-10 carbon ring members. Aryl groups, unless otherwise specified, may optionally be substituted with one or more substituents. In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aryl ring is fused to one or more non-aromatic rings, such as indanyl, phthalimidyl or tetrahydronaphthalyl, and the like, where the point of attachment is on the aryl ring.

The term "aralkyl" refers to an alkyl group, as defined herein, substituted by aryl group, as defined herein, wherein the point of attachment is on the alkyl group.

The term "heteroatom" refers to boron, phosphorus, selenium, nitrogen, oxygen, or sulfur, and includes any oxidized form of nitrogen or sulfur, and any quaternized form of abasic nitrogen.

The terms "heteroaryl" used alone or as part of a larger moiety, e.g., "heteroaralkyl", refer to an aromatic monocyclic or bicyclic hydrocarbon ring system having 5-10 ring atoms wherein the ring atoms comprise, in addition to carbon atoms, from one to five heteroatoms. Heteroaryl groups, unless otherwise specified, may optionally be substituted with one or more substituents. When used in reference to a ring atom of a heteroaryl group, the term "nitrogen" includes a substituted nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaryl ring is fused to one or more aryl, cycloalkyl or heterocycloalkyl rings, wherein the point of attachment is on the heteroaryl ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl.

The term "heteroaralkyl" refers to an alkyl group, as defined herein, substituted by a heteroaryl group, as defined herein, wherein the point of attachment is on the alkyl group.

As used herein, the terms "heterocycloalkyl" or "heterocyclyl" refer to a stable non-aromatic 5-7 membered monocyclic hydrocarbon or stable non-aromatic 7-10 membered bicyclic hydrocarbon that is either saturated or partially unsaturated, and having, in addition to carbon atoms, one or more heteroatoms. Heterocycloalkyl or heterocyclyl groups, unless otherwise specified, may optionally be substituted with one or more substituents. When used in reference to a ring atom of a heterocycloalkyl group, the term "nitrogen" includes a substituted nitrogen. The point of attachment of a heterocycloalkyl group may be at any of its heteroatom or carbon ring atoms that results in a stable structure. Examples of heterocycloalkyl groups include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. "Heterocycloalkyl" also include groups in which the heterocycloalkyl ring is fused to one or more aryl, heteroaryl or cycloalkyl rings, such as indolinyl, chromanyl, phenanthridinyl, or tetrahydroquinolinyl, where the radical or point of attachment is on the heterocycloalkyl ring.

The term "unsaturated", as used herein, means that a moiety has one or more double or triple bonds.

As used herein, the term "partially unsaturated" refers to a ring moiety that includes at least one double or triple bond. The term "partially unsaturated" is intended to encompass rings having multiple sites of unsaturation, but is not intended to include aromatic groups, such as aryl or heteroaryl moieties, as defined herein.

The term "diradical" as used herein refers to an alkyl, alkenyl, alkynyl, aryl, cycloalkyl, heterocycloalkyl, aralkyl, heteroaryl, and heteroaralkyl groups, as described herein, wherein 2 hydrogen atoms are removed to form a divalent moiety. Diradicals are typically end with a suffix of "-ene". For example, alkyl diradicals are referred to as alkylenes (for example:

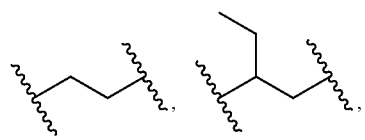

and —(CR'$_2$)$_x$— wherein R' is hydrogen or other substituent and x is 1, 2, 3, 4, 5 or 6); alkenyl diradicals are referred to as "alkenylenes"; alkynyl diradicals are referred to as "alkynylenes"; aryl and aralkyl diradicals are referred to as "arylenes" and "aralkylenes", respectively (for example:

(for example: 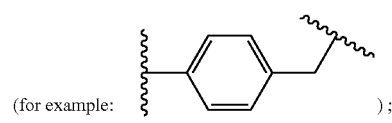 [SMILES: *Cc1ccc(*)cc1] );

heteroaryl and heteroaralkyl diradicals are referred to as "heteroarylenes" and "heteroaralkylenes", respectively (for example:

(for example: 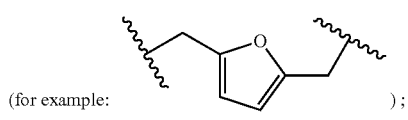 [SMILES: *Cc1ccc(C*)o1] );

cycloalkyl diradicals are referred to as "cycloalkylenes"; heterocycloalkyl diradicals are referred to as "heterocycloalkylenes"; and the like.

The terms "halo" and "halogen" as used herein refer to an atom selected from fluorine (fluoro, —F), chlorine (chloro, —Cl), bromine (bromo, —Br), and iodine (iodo, —I).

As used herein, the term "haloalkyl" refers to an alkyl group, as described herein, wherein one or more of the hydrogen atoms of the alkyl group is replaced with one or more halogen atoms.

In certain embodiments, the haloalkyl group is a perhaloalkyl group, that is, having all of the hydrogen atoms of the alkyl group replaced with halogens (e.g., such as the perfluoroalkyl group —$CF_3$).

As used herein, the term "azido" refers to the group —$N_3$.

As used herein, the term "nitrile" refers to the group —CN.

As used herein, the term "nitro" refers to the group —$NO_2$.

As used herein, the term "hydroxyl" or "hydroxy" refers to the group —OH.

As used herein, the term "thiol" or "thio" refers to the group —SH.

As used herein, the term "carboxylic acid" refers to the group —$CO_2H$.

As used herein, the term "aldehyde" refers to the group —CHO.

As used herein, the term "alkoxy" refers to the group —OR', wherein R' is an alkyl, alkenyl or alkynyl group, as defined herein.

As used herein, the term "aryloxy" refers to the group —OR', wherein each R' is an aryl or heteroaryl group, as defined herein.

As used herein, the term "alkylthio" or "alkylthiooxy" refers to the group —SR', wherein each R' is, independently, a carbon moiety, such as, for example, an alkyl, alkenyl, or alkynyl group, as defined herein.

As used herein, the term "arylthio" refers to the group —SR', wherein each R' is an aryl or heteroaryl group, as defined herein.

As used herein, the term "amino" refers to the group —$NR'_2$, wherein each R' is, independently, hydrogen, a carbon moiety, such as, for example, an alkyl, alkenyl, alkynyl, aryl or heteroaryl group, as defined herein, or two R' groups together with the nitrogen atom to which they are bound form a 5-8 membered ring.

As used herein, the term "carbonyl" refers to the group —C(=O)R', wherein R' is, independently, a carbon moiety, such as, for example, an alkyl, alkenyl, alkynyl, aryl or heteroaryl group, as defined herein.

As used herein, the term "ester" refers to the group —C(=O)OR' or —OC(=O)R' wherein each R' is, independently, a carbon moiety, such as, for example, an alkyl, alkenyl, alkynyl, aryl or heteroaryl group, as defined herein.

As used herein, the term "amide" or "amido" refers to the group —C(=O)N(R')₂ or —NR'C(=O)R' wherein each R' is, independently, hydrogen or a carbon moiety, such as, for example, an alkyl, alkenyl, alkynyl, aryl or heteroaryl group, as defined herein, or two R' groups together with the nitrogen atom to which they are bound form a 5-8 membered ring.

As used herein, the term "imide" or "imido" refers to the group —C(=NR')N(R')₂ or —NR'C(=NR')R' wherein each R' is, independently, hydrogen or a carbon moiety, such as, for example, an alkyl, alkenyl, alkynyl, aryl or heteroaryl group, as defined herein, or wherein two R' groups together with the nitrogen atom to which they are bound form a 5-8 membered ring.

As used herein "silyl" refers to the group —Si(R')₃ wherein R' is a carbon moiety, such as, for example, an alkyl, alkenyl, aryl or heteroaryl group.

The term "salt" refers to inorganic and organic acid addition salts of compounds of the present invention. Non-limiting examples of representative salts include salts derived from suitable inorganic and organic acids, e.g., hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other acid addition salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like (see, for example, Berge et al. (1977) "Pharmaceutical Salts", *J. Pharm. Sci.* 66:1-19, incorporated herein by reference).

BRIEF DESCRIPTION OF THE DRAWINGS

FIG. 2A depicts the L-alanine dehydrogenase (LADH)/formate dehydrogenase (FDH) promoted transamination. FIG. 2B depicts the lactate dehydrogenase (LDH)/Glucose dehydrogenase (GDH) promoted transamination.

DETAILED DESCRIPTION

Figure 1:
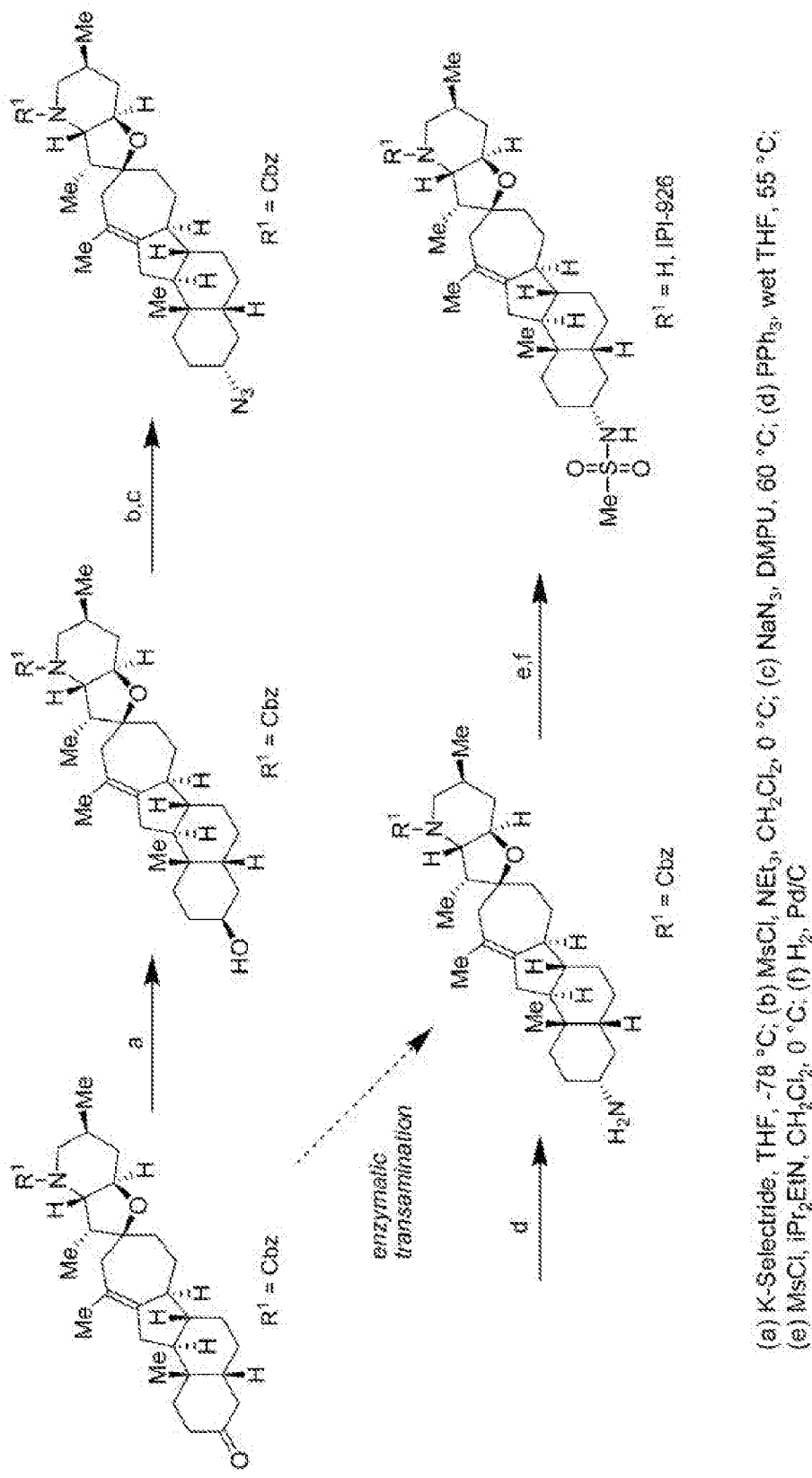
FIG. 1 depicts the chemical synthesis of IPI-926 in six steps from a ketone starting material as described in Tremblay et al., "Discovery of a Potent and Orally Active Hedgehog Pathway Antagonist (IPI-926)" *J. Med. Chem.* (2009) 52:4400-4418. The inventive transamination method shortens this route by at least three steps.
Figure 2A:
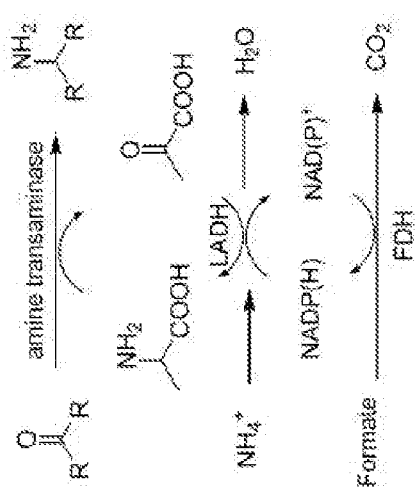
FIGS. 2A-B depict two types of enzymatic transaminations.
Figure 2B:
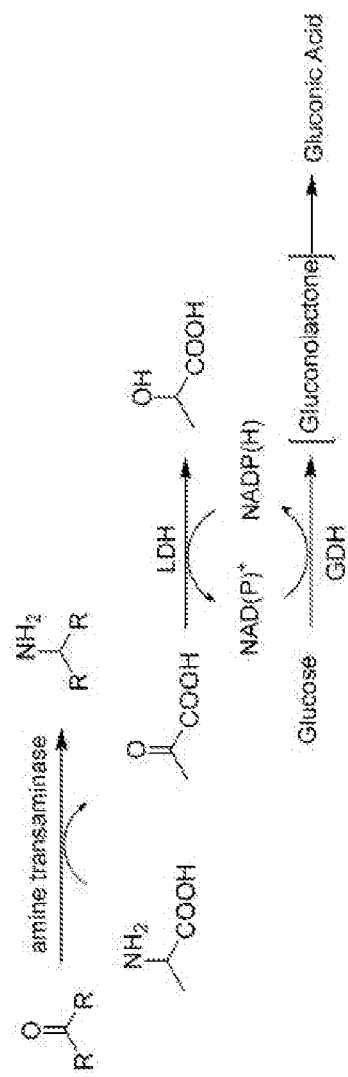

Provided is a process for preparing a compound of formula (II):

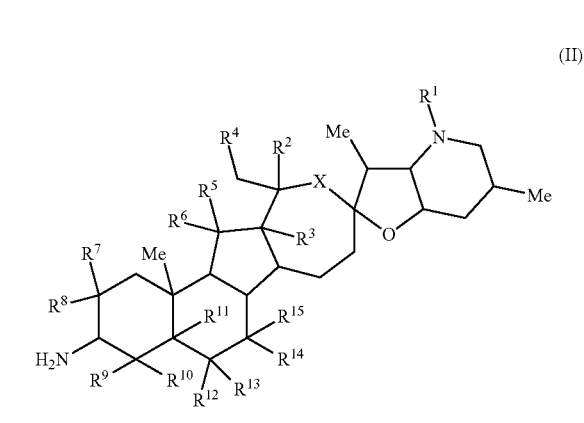

or a salt thereof;

from a compound of formula (I):

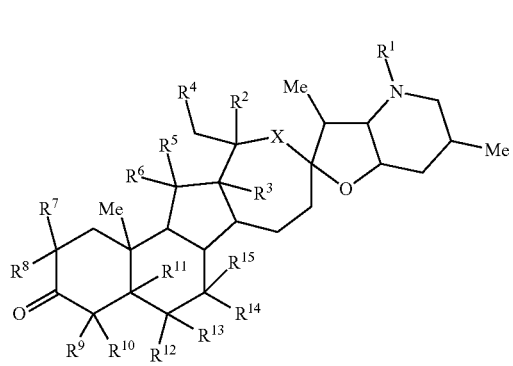

or a salt thereof;
wherein:
$R^1$ is H, alkyl, alkenyl, alkynyl, aryl, cycloalkyl, heterocycloalkyl, aralkyl, heteroaryl, heteroaralkyl, haloalkyl, —$OR^{16}$, —$C(O)R^{16}$, —$CO_2R^{16}$, —$SO_2R^{16}$, —$C(O)N(R^{17})(R^{17})$, —$[C(R^{16})_2]_q$—$R^{16}$, —$[(W)—N(R^{17})C(O)]_qR^{16}$, —$[(W)—C(O)]_qR^{16}$, —$[(W)—C(O)O]_qR^{16}$, —$[(W)—OC(O)]_qR^{16}$, —$[(W)—SO_2]_qR^{16}$, —$[(W)N(R^{17})SO_2]_qR^{16}$, —$[(W)—C(O)N(R^{17})]_qR^{17}$, —$[(W)—O]_qR^{16}$, —$[(W)—N(R^{17})]_qR^{16}$, or $[(W)—S]_qR^{16}$; wherein W is a diradical and q is 1, 2, 3, 4, 5, or 6;

each $R^2$ and $R^3$ is, independently, H, alkyl, alkenyl, alkynyl, aryl, cycloalkyl, heterocycloalkyl, aralkyl, heteroaryl, heteroaralkyl, haloalkyl, halo, —$OR^{16}$, —$OR^{16}$, —$N(R^{17})_2$, or —$SR^{16}$, or $R^2$ and $R^3$ taken together form a double bond or form a group

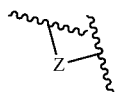

wherein Z is $NR^{17}$, O, or $C(R^{18})_2$;
$R^4$ is independently H, halo, —$OR^{16}$, —$N(R^{17})_2$, or —$SR^{16}$;

each $R^5$ and $R^6$, is, independently, H, alkyl, alkenyl, alkynyl, aryl, cycloalkyl, heterocycloalkyl, aralkyl, heteroaryl, heteroaralkyl, halo, —$OR^{16}$, —$N(R^{17})_2$, or —$SR^{16}$;

or $R^5$ and $R^6$ taken together with the carbon to which they are bonded, form C=O, C=S, C=N—$OR^{17}$, C=N—$R^{17}$, C=N—$N(R^{17})_2$, or form an optionally substituted 3-8 membered ring;

each $R^7$, $R^8$, $R^9$, $R^{10}$, $R^{11}$, $R^{12}$ and $R^{13}$ is, independently, H, alkyl, alkenyl, alkynyl, aryl, cycloalkyl, heterocycloalkyl, aralkyl, heteroaryl, heteroaralkyl, halo, —$OR^{16}$, —$N(R^{17})_2$, or —$SR^{16}$;

or $R^{10}$ and $R^{11}$ taken together, or $R^{11}$ and $R^{12}$ taken together, form a double bond or form a group

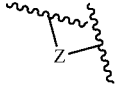

wherein Z is $NR^{17}$, O, or $C(R^{18})_2$;

each $R^{14}$ and $R^{15}$ is, independently, H, halo, —$OR^6$, —$N(R^{17})_2$, or —$SR^{16}$;

or $R^{14}$ and R' taken together with the carbon to which they are bonded, form C=O or C=S;

X is a bond or the group —$C(R^{19})_2$—; wherein each $R^{19}$ is, independently, H, alkyl, aralkyl, halo, —CN, —$OR^{16}$, or —$N(R^{17})_2$;

$R^{16}$ is H, alkyl, alkenyl, alkynyl, aryl, cycloalkyl, heterocycloalkyl, aralkyl, heteroaryl, heteroaralkyl or —$[C(R^{20})_2]_p$—$R^2$ wherein p is 0-6; or any two occurrences of $R^{16}$ on the same substituent are taken together to form a 4-8 membered optionally substituted ring;

$R^{17}$ is H, alkyl, alkenyl, alkynyl, aryl, cycloalkyl, heterocycloalkyl, aralkyl, heteroaryl, heteroaralkyl, —$C(=O)R^{20}$, —$C(=O)OR^{20}$, —$SO_2R^{20}$, —$C(=O)N(R^{20})_2$, or —$[C(R^{20})_2]_p$—$R^2$ wherein p is 0-6; or any two occurrences of $R^{17}$ on the same substituent are taken together to form a 4-8 membered optionally substituted ring;

$R^{18}$ is H, alkyl, alkenyl, alkynyl, aryl, cycloalkyl, heterocycloalkyl, aralkyl, heteroaryl, heteroaralkyl, halo, —CN, —$OR^{20}$, —$OSi(R^{20})_3$, —$C(=O)R^{20}$, —$C(=O)OR^{20}$, —$SO_2R^{20}$, or —$C(=O)N(R^{20})_2$;

$R^{20}$ is H, alkyl, alkenyl, alkynyl, aryl, cycloalkyl, heterocycloalkyl, aralkyl, heteroaryl, or heteroaralkyl; or any two occurrences of $R^{20}$ on the same substituent are taken together to form a 4-8 membered optionally substituted ring;

$R^{21}$ is —$OR^{22}$, —$N(R^{22})C(=O)R^{22}$, —$N(R^{22})C(=O)OR^{22}$, —$N(R^{22})SO_2(R^{22})$, —$C(=O)R^{22}N(R^{22})_2$, —$OC(=O)R^{22}N(R^{22})(R^{22})$, —$SO_2N(R^{22})(R^{22})$, —$N(R^{22})(R^{22})$, —$C(=O)OR^{22}$, —$C(=O)N(OH)(R^{22})$, —$OS(O)_2OR^{22}$, —$S(O)_{20}R^{22}$, —$OP(=O)(OR^{22})(OR^{22})$, —$N(R^{22})P(O)(OR^{22})(OR^{22})$, or —$P(=O)(OR^{22})(OR^{22})$; and $R^{22}$ is H, alkyl, alkenyl, alkynyl, aryl, cycloalkyl, heterocycloalkyl, aralkyl, heteroaryl, heteroaralkyl; or any two occurrences of $R^{22}$ on the same substituent are taken together to form a 4-8 membered optionally substituted ring;

the process comprising contacting a compound of formula (I) or a salt thereof, an amino donor molecule, and an amine transaminase enzyme in a solution to provide a compound of formula (II) or a salt thereof.

In certain embodiments, $R^1$ is H, alkyl, alkenyl, alkynyl, aryl, cycloalkyl, heterocycloalkyl, aralkyl, heteroaryl, heteroaralkyl, haloalkyl, —$OR^{16}$, —$C(O)R^{16}$, —$CO_2R^{16}$, —$SO_2R^{16}$, $C(O)N(R^{17})(R^{17})$, or —$[C(R^{16})_2]_q$—$R^6$. In certain embodiments, $R^1$ is H, aralkyl, —$C(O)R^{16}$, $CO_2R^{16}$, —$SO_2R^{16}$ or —$C(O)N(R^{17})(R^{17})$. In certain embodiments, $R^1$ is H, aralkyl or —$CO_2R^{16}$.

In certain embodiments, $R^1$ is H.

In certain embodiments, $R^1$ is aralkyl.

In certain embodiments, $R^1$ is —$CO_2R^{16}$. In certain embodiments, $R^1$ is —$CO_2R^{16}$ and $R^{16}$ is alkyl, alkenyl, alkynyl, aryl, cycloalkyl, heterocycloalkyl, aralkyl, heteroaryl or heteroaralkyl. In certain embodiments, $R^1$ is a -Boc group (e.g., wherein $R^1$ is —$CO_2R^{16}$ and $R^{16}$ is t-butyl). In certain embodiments, $R^1$ is a -CBz group (e.g., wherein $R^1$ is —$CO_2R^{16}$ and $R^{16}$ is benzyl).

In certain embodiments, $R^2$ and $R^3$ taken together form a double bond.

In certain embodiments, $R^2$ and $R^3$ form a group:

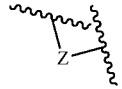

wherein Z is —NR$^{17}$—, —O—, or —C(R$^{18}$)$_2$—. In certain embodiments, Z is —C(R$^{18}$)$_2$—. In certain embodiments, Z is —CH$_2$—.

In certain embodiments, X is a bond. For example, in certain embodiments, wherein R$^2$ and R$^3$ are taken together form a double bond, or wherein R$^2$ and R$^3$ form a group:

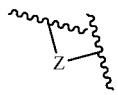

and Z is —NR$^{17}$—, —O—, or —C(R$^{18}$)$_2$—, then X is a bond.

In certain embodiments, X is the group —C(R$^{19}$)$_2$—. In certain embodiments, R$^{19}$ is H, e.g., wherein X is —CH$_2$—.

In certain embodiments, wherein R$^2$ and R$^3$ are taken together form a double bond, then X is the group —C(R$^{19}$)$_2$—. In certain embodiments, wherein R$^2$ and R$^3$ are taken together form a double bond, then X is the group —CH$_2$—.

In certain embodiments, R$^4$ is H.

In certain embodiments, each R$^5$ and R$^6$, is, independently, H, or R$^5$ and R$^6$ taken together, along with the carbon to which they are bonded, form C=O. In certain embodiments, each of R$^5$ and R$^6$ is independently H. In certain embodiments, R$^5$ and R$^6$ taken together with the carbon to which they are bonded form C=O.

In certain embodiments, R$^7$ and R$^8$ are each H.

In certain embodiments, R$^9$ and R$^{10}$ are each H.

In certain embodiments, R$^{11}$ is a H.

In certain embodiments, R$^{12}$ and R$^{13}$ are each H.

In certain embodiments, R$^{14}$ and R$^{10}$ are each H.

In certain embodiments, each of R$^7$, R$^8$, R$^9$, R$^{10}$, R$^{11}$, R$^{12}$, R$^{13}$, R$^{14}$ and R$^{15}$ is H.

In certain embodiments, R$^9$ is H and R$^{10}$ and R$^{11}$ taken together form a double bond.

In certain embodiments, R$^{13}$ is H, and R$^{11}$ and R$^{12}$ taken together form a double bond.

In certain embodiments, the compound of formula (I) is a compound of the formula (I-AA):

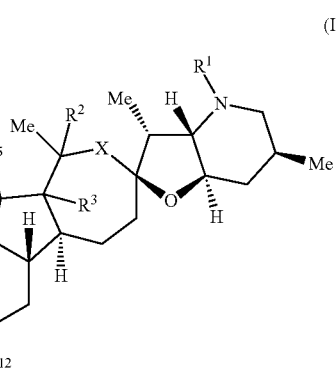

(I-AA)

or salt thereof, and the compound of formula (II) is a compound of the formula (II-AA):

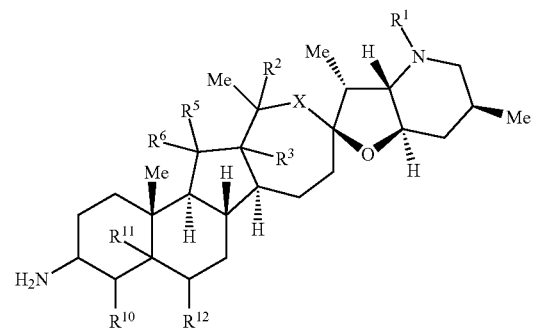

(II-AA)

or salt thereof, wherein R$^1$, R$^2$, R$^3$, R$^5$, R$^6$, R$^{10}$, R$^{11}$, R$^{12}$ and X are as defined herein.

In certain embodiments, the compound of formula (I) is a compound of the formula (I-BB):

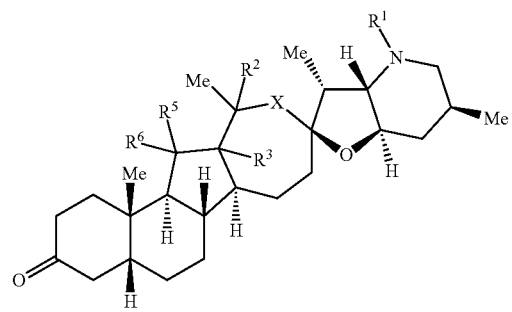

(I-BB)

or salt thereof, and the compound of formula (II) is a compound of the formula (II-BB):

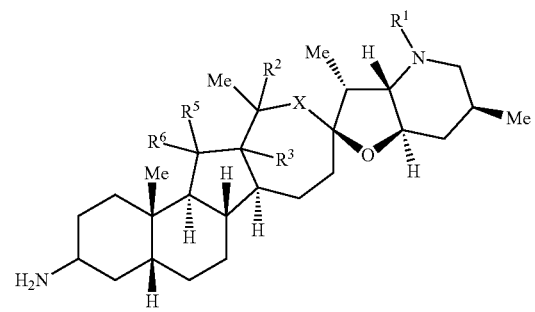

(II-BB)

or salt thereof, wherein R$^1$, R$_2$, R$^3$, R$^5$, R$^6$ and X are as defined herein.

In certain embodiments, the compound of formula (I) is a compound of the formula (I-CC):

(I-CC)

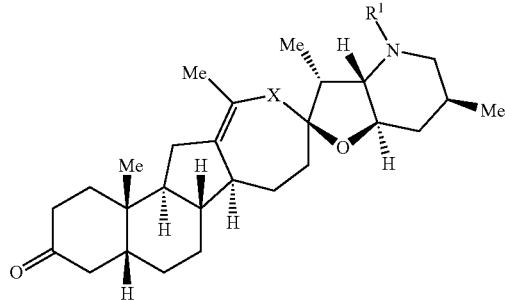

or salt thereof,
and the compound of formula (II) is a compound of the formula (II-CC):

(II-CC)

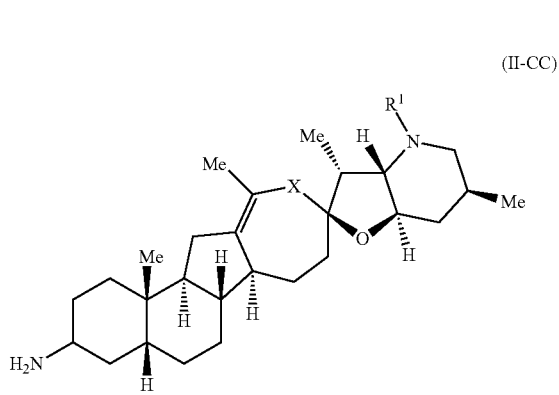

or salt thereof,
wherein $R^1$ and X are as defined herein.

Exemplary compounds of formula (I) are provided in U.S. Pat. No. 7,230,004, U.S. Pat. No. 7,407,967, U.S. Publication No. 20080293754, and U.S. Publication No. 20090012109, each of which is incorporated herein by reference in their entirety.

In certain embodiments, the compound of formula (I) or a salt thereof, and a compound of formula (II) or a salt thereof, are selected from the set of compounds, or salts thereof, provided in Tables 1, 2, 3 and 4, and wherein $R^1$ is as defined above and herein:

TABLE 1

| Compound of formula (I) |
|---|
| (I-a) 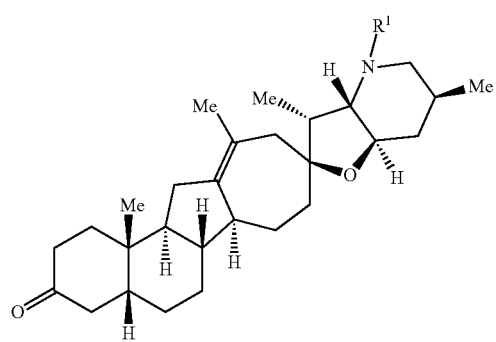 |

TABLE 1-continued

| (I-b) 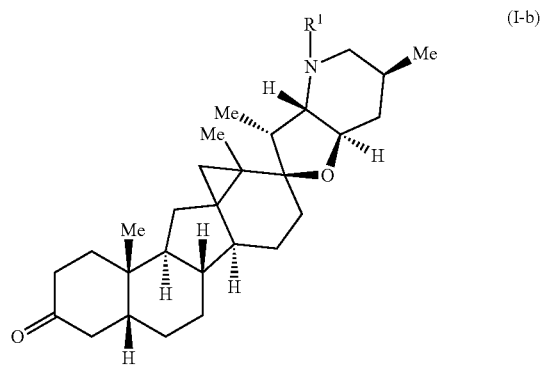 |
|---|
| (I-c) 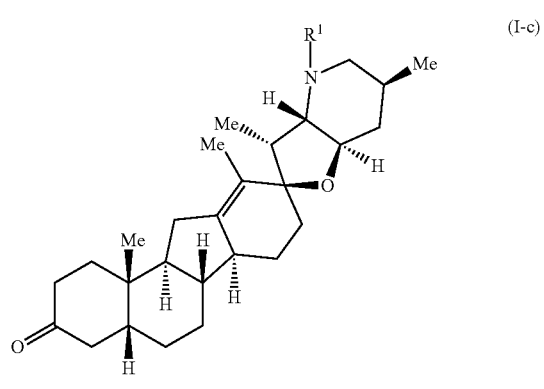 |
| (I-d) 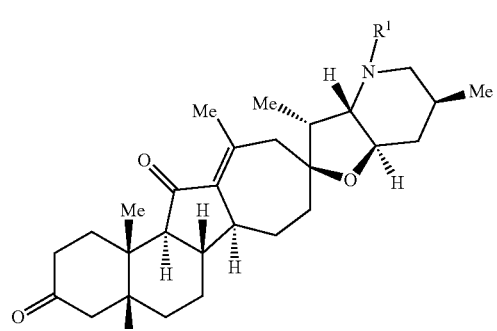 |
| (I-e) 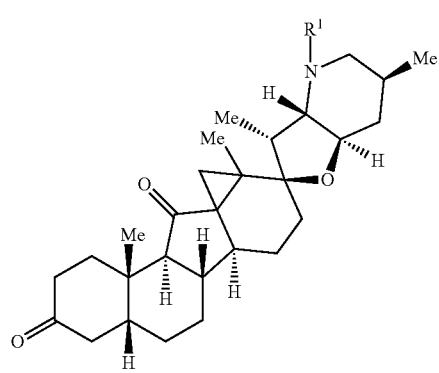 |

TABLE 1-continued
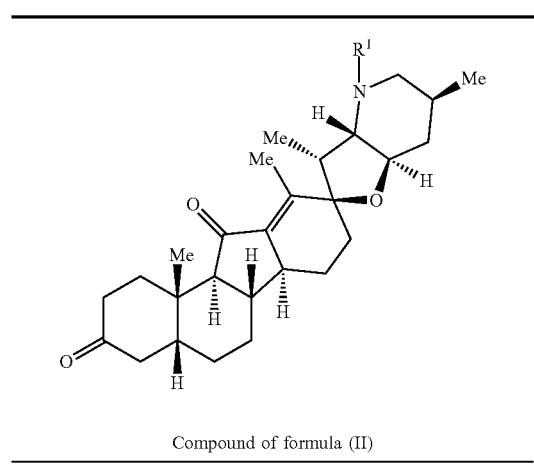
(I-f)
Compound of formula (II)
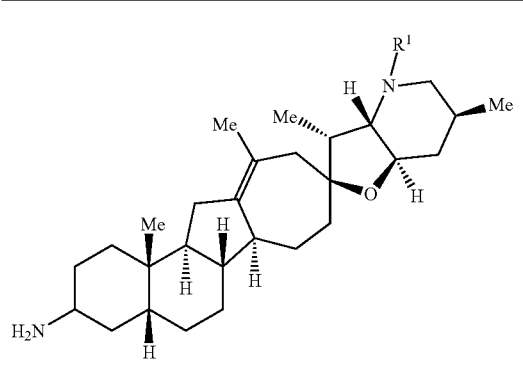
(II-a)
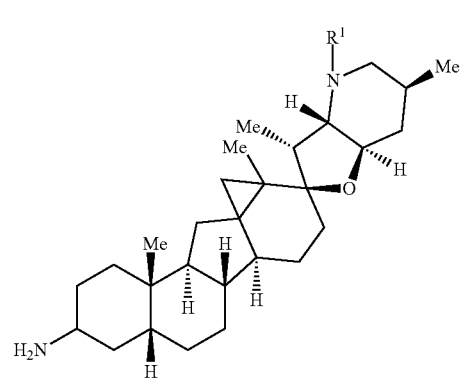
(II-b)
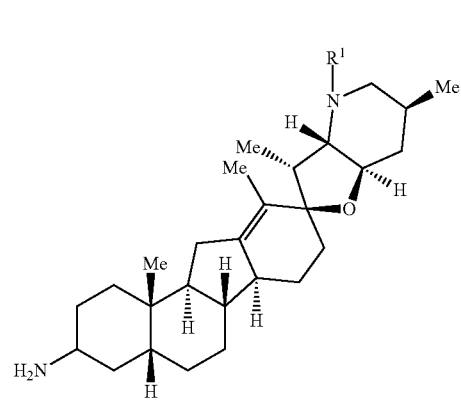
(II-c)
TABLE 1-continued
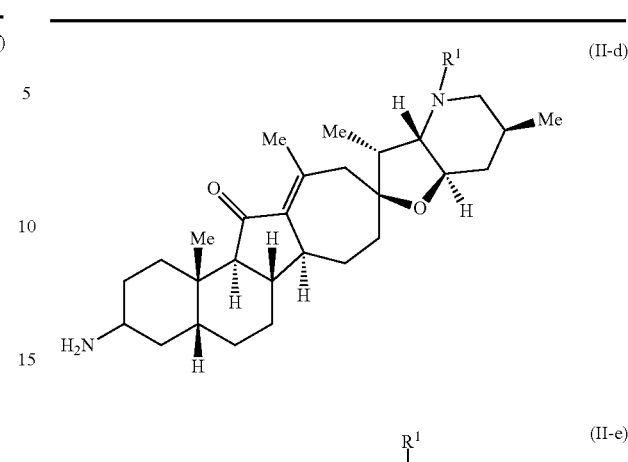
(II-d)
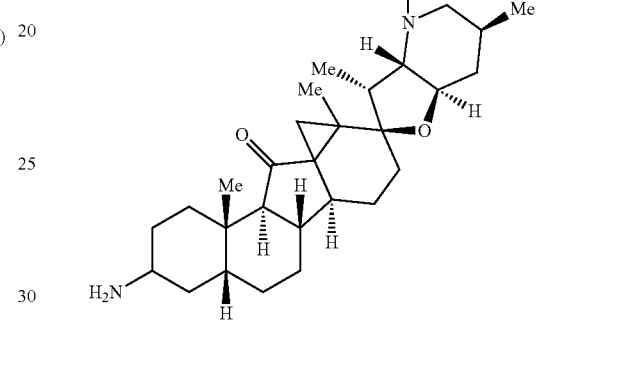
(II-e)
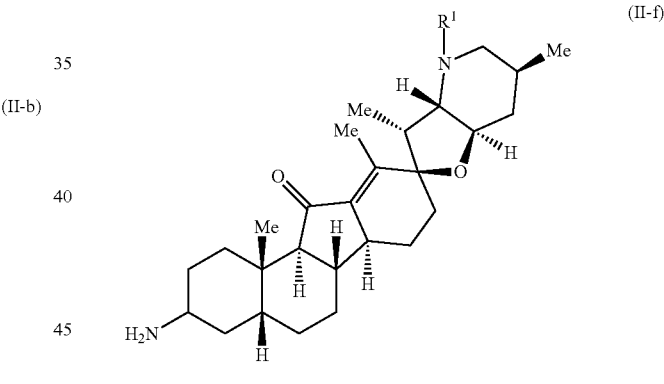
(II-f)
TABLE 2
Compound of formula (I)
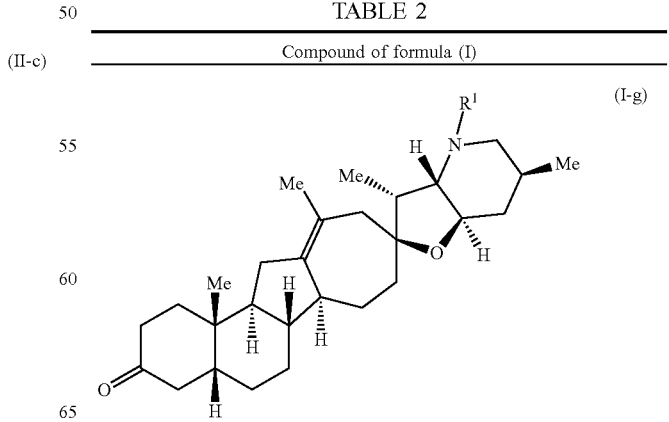
(I-g)

TABLE 2-continued
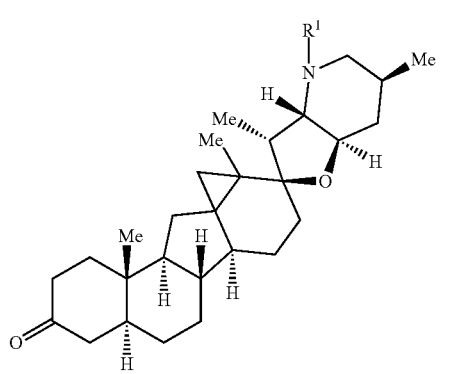
(I-h)
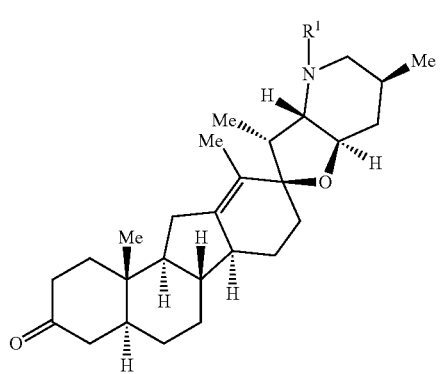
(I-i)
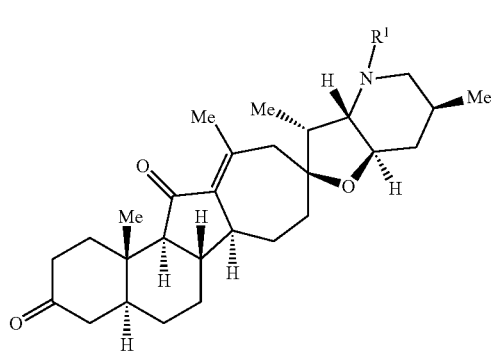
(I-j)
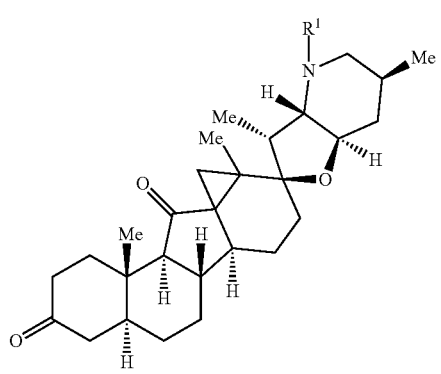
(I-k)
TABLE 2-continued
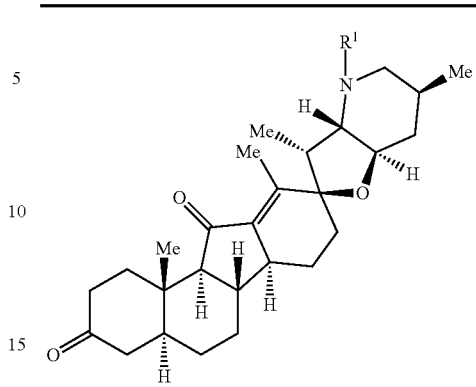
(I-l)
Compound of formula (II)
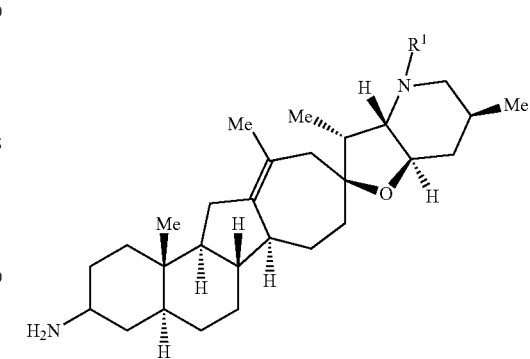
(II-g)
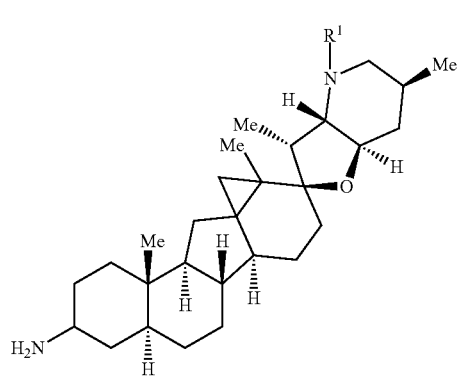
(II-h)
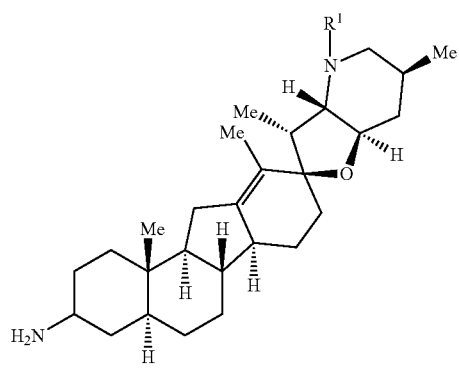
(II-i)

TABLE 2-continued
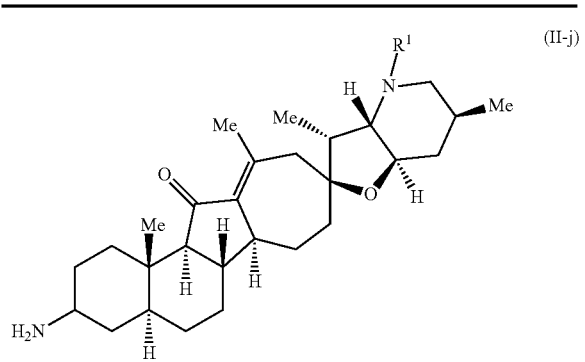
(II-j)
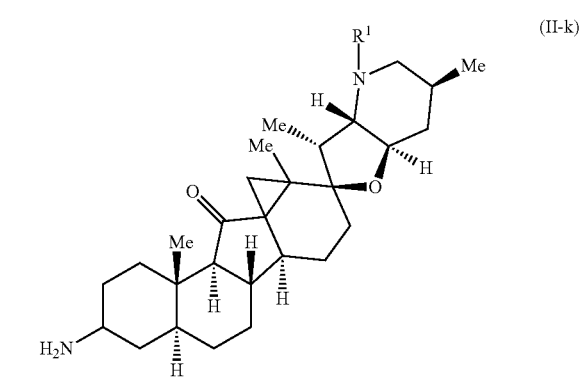
(II-k)
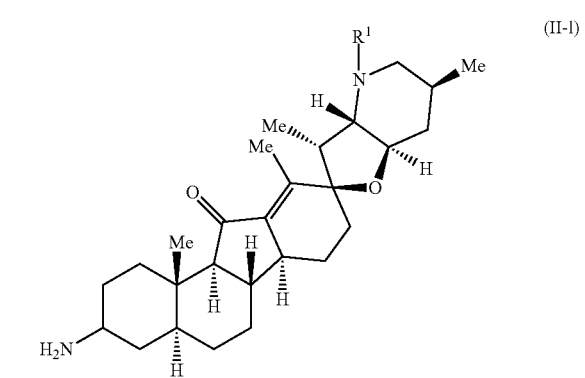
(II-l)
TABLE 3
Compound of formula (I)
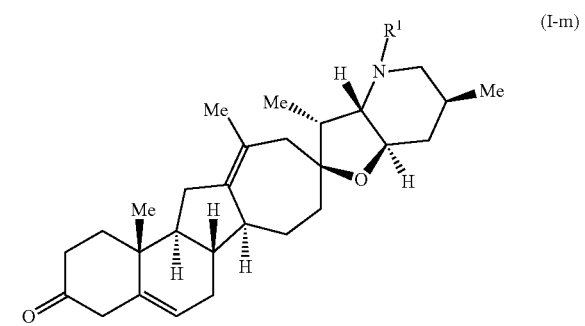
(I-m)
TABLE 3-continued
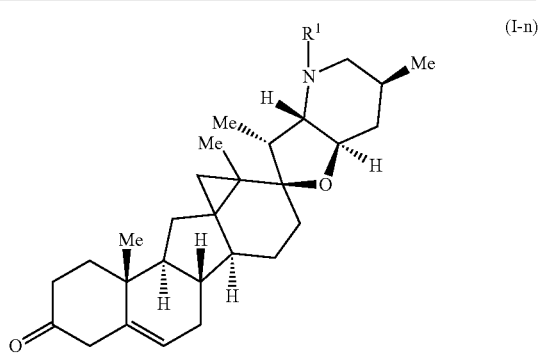
(I-n)
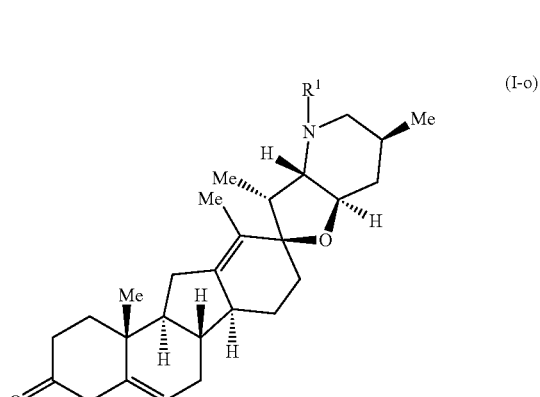
(I-o)
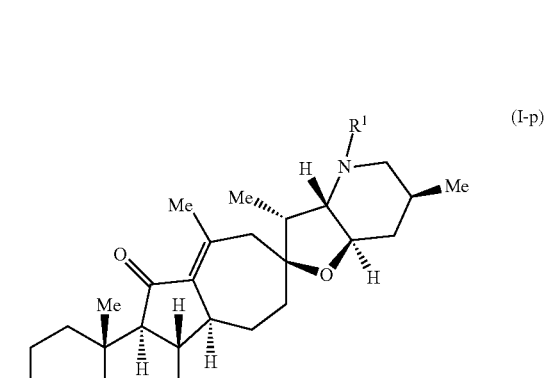
(I-p)
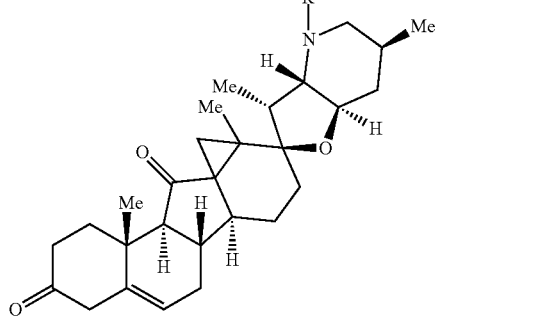
(I-q)

TABLE 3-continued
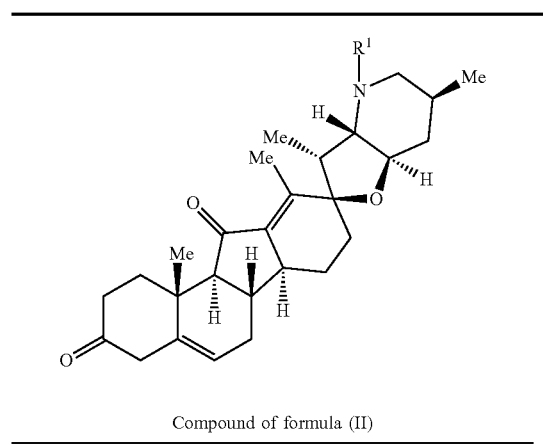
(I-r)
Compound of formula (II)
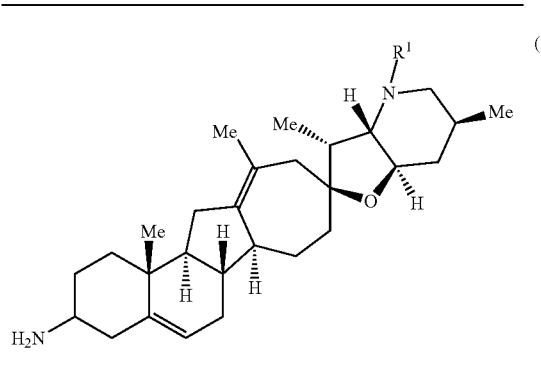
(II-m)
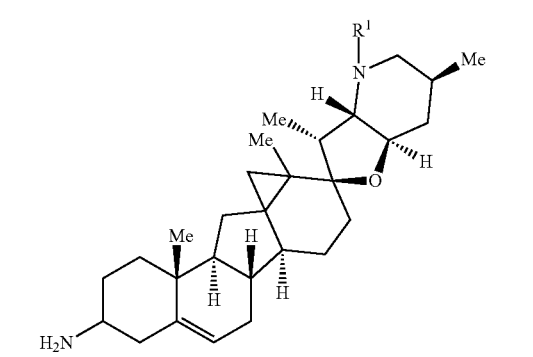
(II-n)
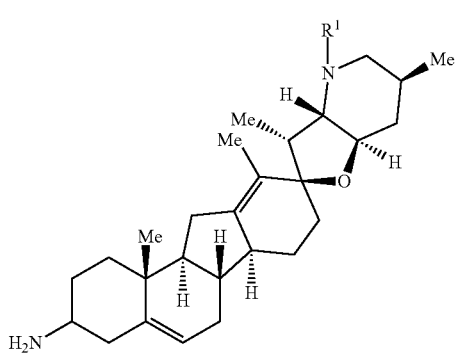
(II-o)
TABLE 3-continued
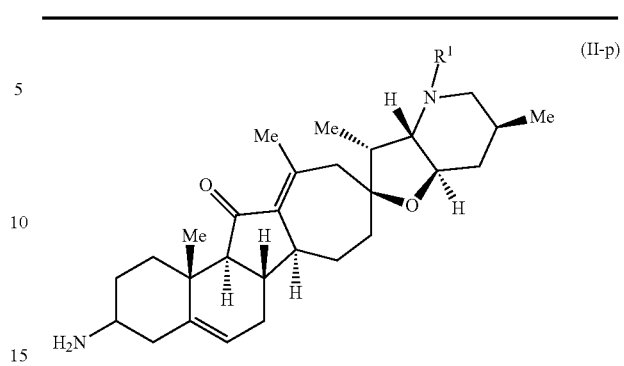
(II-p)
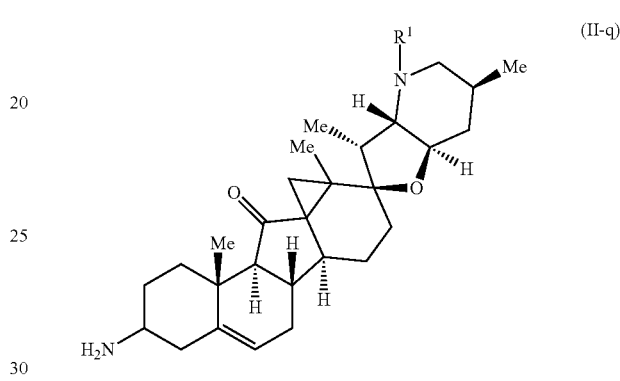
(II-q)
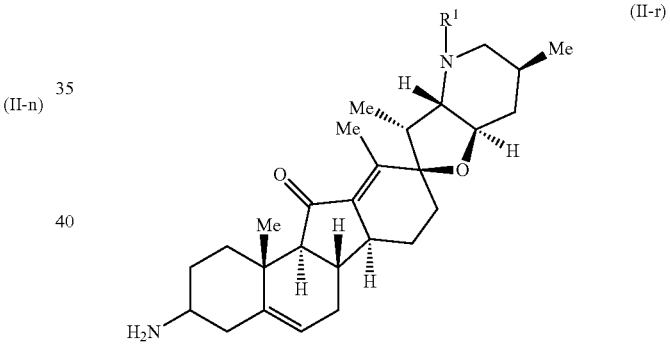
(II-r)
TABLE 4
Compound of formula (I)
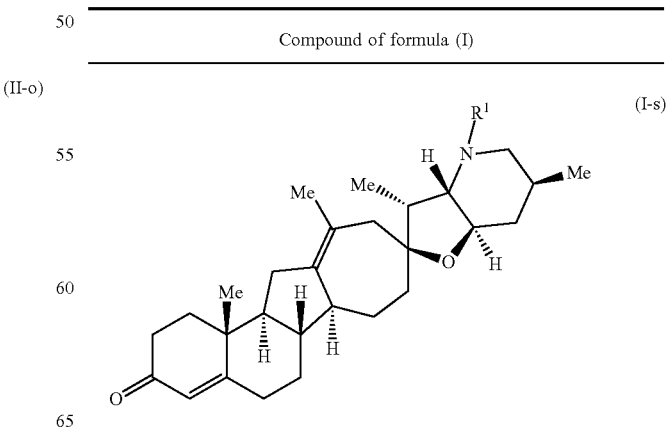
(I-s)

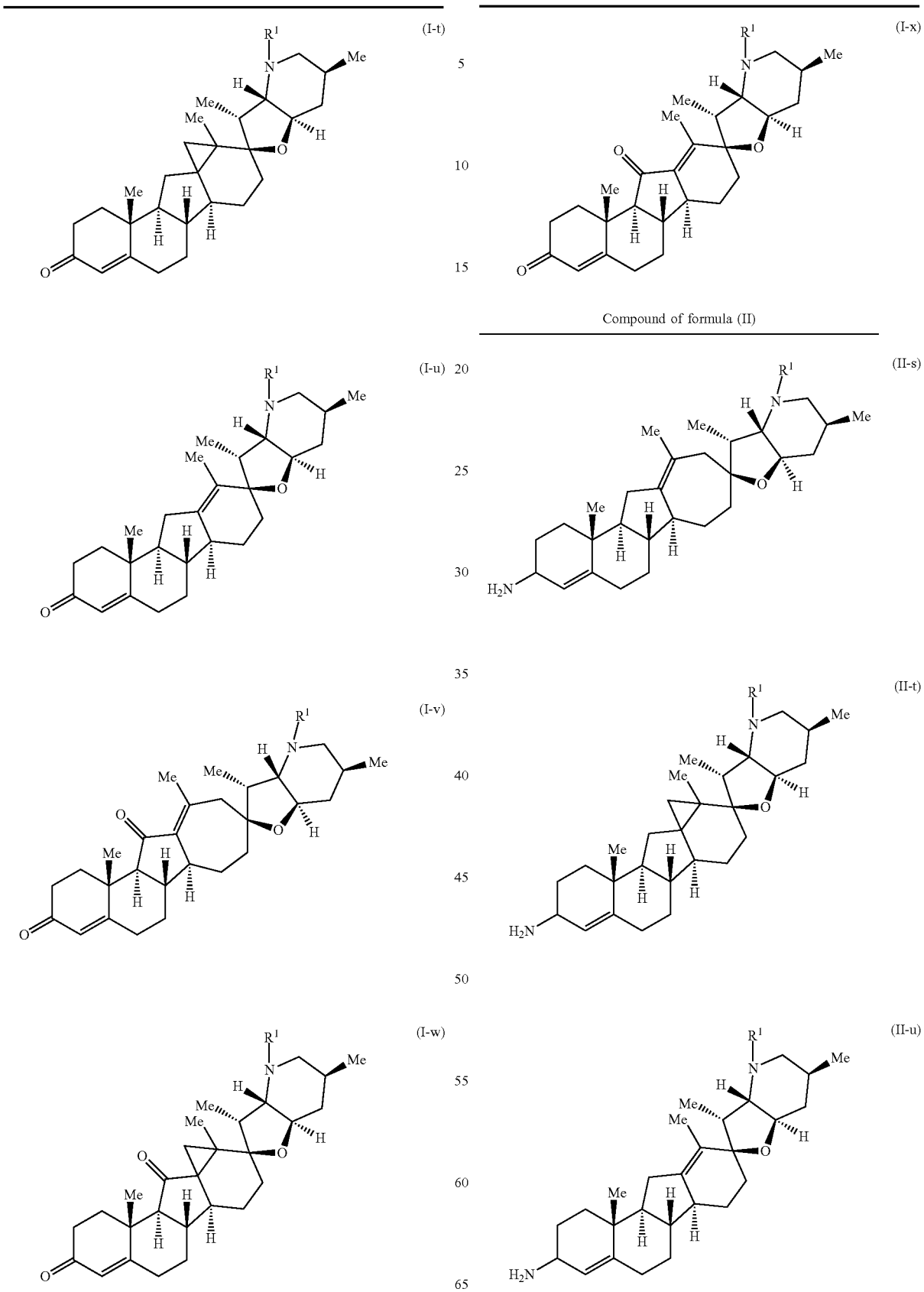

TABLE 4-continued

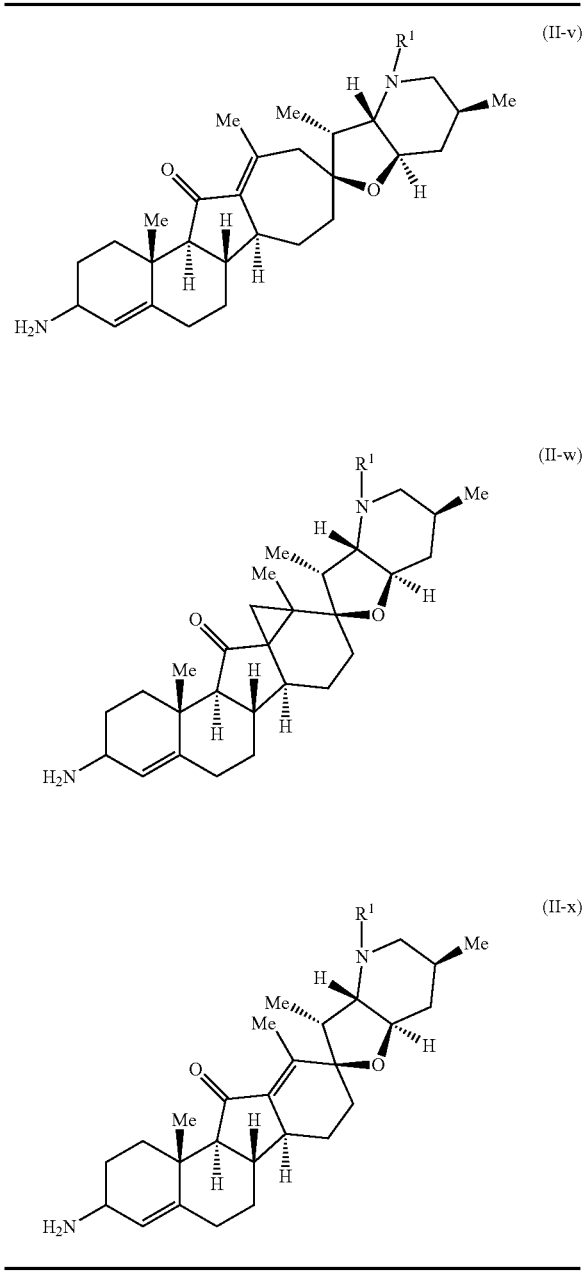

In certain embodiments, $R^1$ is H.

In certain embodiments, $R^1$ is aralkyl.

In certain embodiments, $R^1$ is $-CO_2R^{16}$. In certain embodiments, $R^1$ is $-CO_2R^{16}$ and $R^{16}$ is alkyl, alkenyl, alkynyl, aryl, cycloalkyl, heterocycloalkyl, aralkyl, heteroaryl or heteroaralkyl. In certain embodiments, $R^1$ is a -Boc group (e.g., wherein $R^1$ is $-CO_2R^6$ and $R^{16}$ is t-butyl). In certain embodiments, $R^1$ is a -CBz group (e.g., wherein $R^1$ is $-CO_2R^{16}$ and $R^{16}$ is benzyl).

In certain embodiments, the process preferentially generates a compound of formula (II), or a salt thereof, from a compound of formula (I), or salt thereof, wherein the newly-formed amino group provided in formula (II) has (R) or (S) stereochemistry.

For example, in certain embodiments, the process preferentially generates a compound of formula (II), or salt thereof, wherein the newly-formed amino group has (S) stereochemistry, e.g., a compound of the formula (S)-(II):

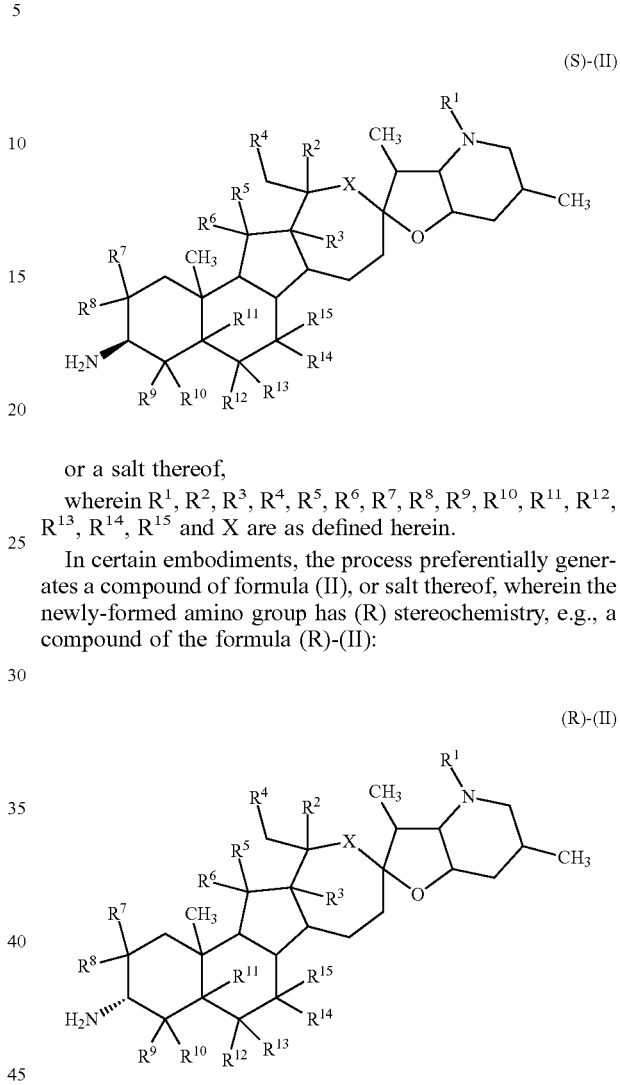

or a salt thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and X are as defined herein.

In certain embodiments, the process preferentially generates a compound of formula (II), or salt thereof, wherein the newly-formed amino group has (R) stereochemistry, e.g., a compound of the formula (R)-(II):

or a salt thereof, wherein $R^1$, $R^2$, $R^3$, $R^4$, $R^5$, $R^6$, $R^{17}$, $R^8$, $R^9$, $R^{10}$, $R^{11}$, $R^{12}$, $R^{13}$, $R^{14}$, $R^{15}$ and X are as defined herein.

As used herein, "preferentially generates" refers to the production of one stereoisomer of a compound of formula (II) in excess over the other stereoisomer. In certain embodiments, the process preferentially generates a compound of formula (II), or a salt thereof, wherein the newly-formed amino group has (R) or (S) stereochemistry, in greater than 40% diastereomeric excess (de), greater than 50% de, greater than 60% de, greater than 70% de, greater than 75% de, greater than 80% de, greater than 85% de, greater than 90% de, greater than 95% de, greater than 98% de, or greater than 99% de, as determined by HPLC.

In a preferred embodiment, the process preferentially generates a compound of formula (II), or salt thereof, wherein the newly-formed amino group has (R) stereochemistry.

For example, in certain embodiments, the compound of formula (I) is of the formula (I-AA):

(I-AA)

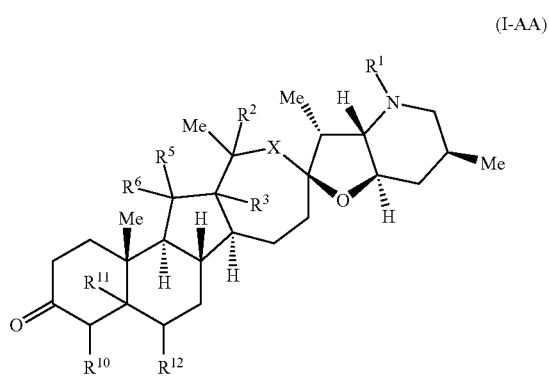

or salt thereof,
and the compound of formula (II) is of the formula (R)-(II-AA):

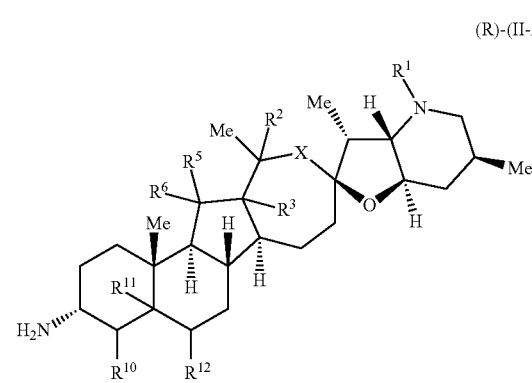

or salt thereof,
wherein $R^1$, $R^2$, $R^3$, $R^5$, $R^6$, R, $R^{11}$, $R^{12}$ and X are as defined herein.

In certain embodiments, the compound of formula (I) is of the formula (I-BB):

(I-BB)

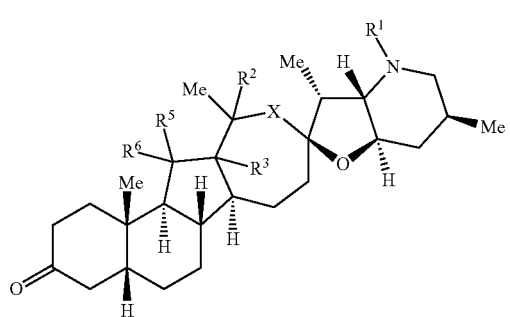

or salt thereof,
and the compound of formula (II) is of the formula (R)-(II-BB):

(R)-(II-BB)

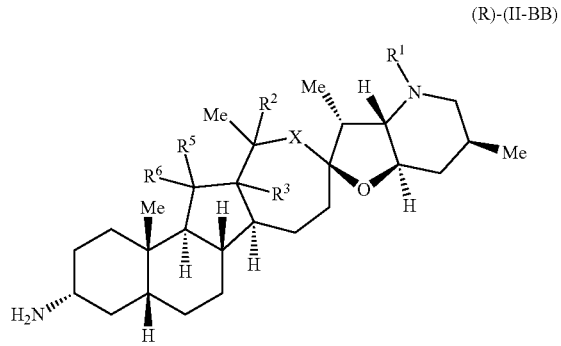

or salt thereof,
wherein $R^1$, $R^2$, $R^3$, $R^5$, $R^6$ and X are as defined herein.

In certain embodiments, the compound of formula (I) is of the formula (I-CC):

(I-CC)

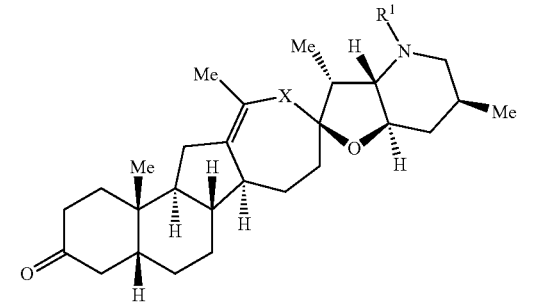

or salt thereof,
and the compound of formula (II) is of the formula (R)-(II-CC):

(R)-(II-CC)

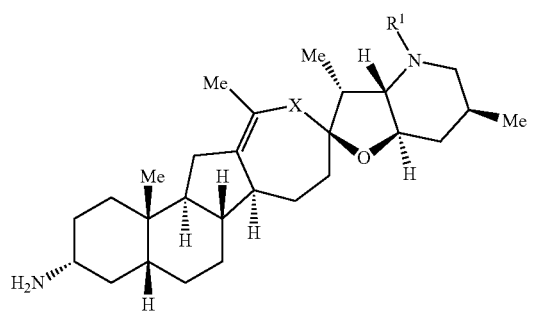

or salt thereof,
wherein $R^1$ and X are as defined herein.

In another preferred embodiment, the compound of formulae (I) and (II) are selected from the set of compounds, or salts thereof, provided in Table 1.

In certain preferred embodiments, the process preferentially generates a compound of formula (II) of Table 1, or salt thereof, wherein the newly-formed amino group has (R) stereochemistry.

For example, in certain embodiments, the compound of formulae (I) and (II) are selected from a set of compounds, or salts thereof, provided in Table 5, wherein the newly-formed amino group of the compound of formula (II) has (R) stereochemistry:
TABLE 5
Compound of formula (I)
(I-a)
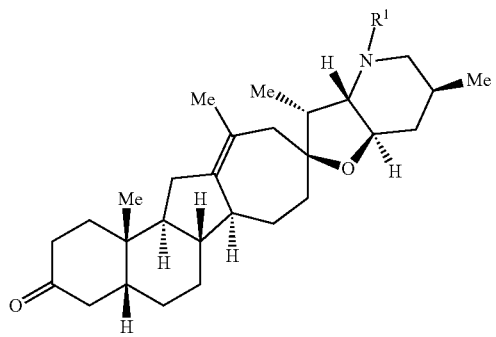
(I-b)
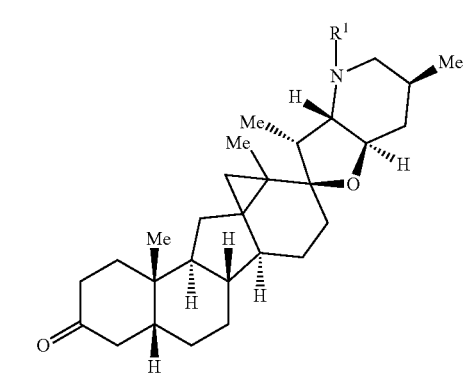
(I-c)
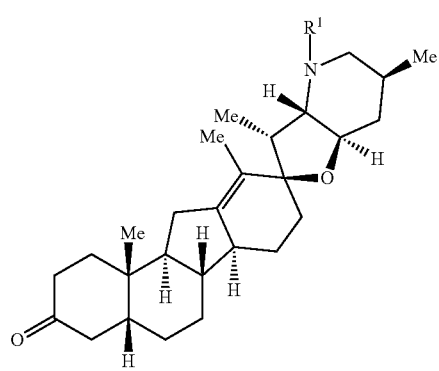
(I-d)
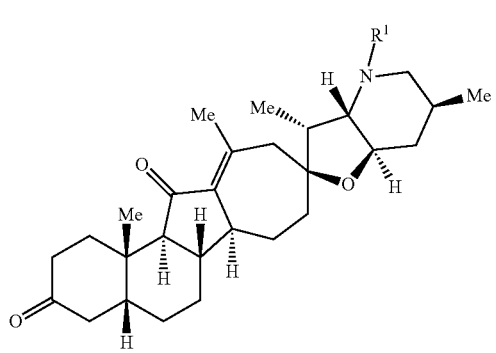
TABLE 5-continued
(I-e)
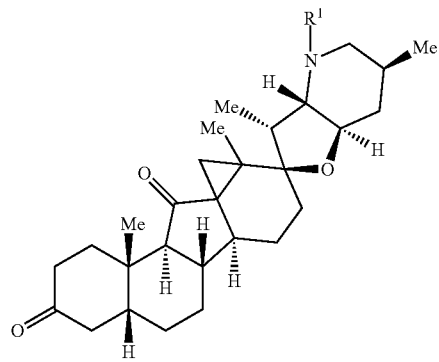
(I-f)
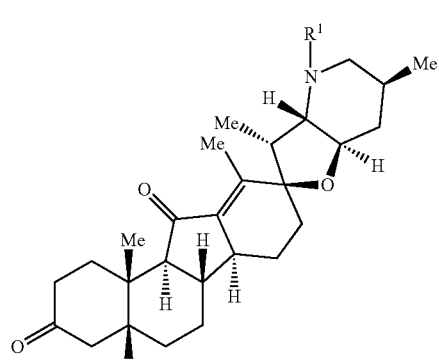
Compound of formula (II)
(R)-(II-a)
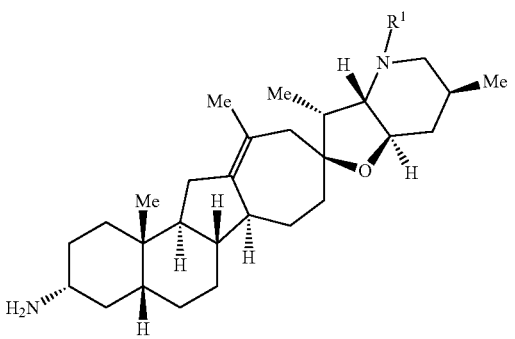
(R)-(II-b)
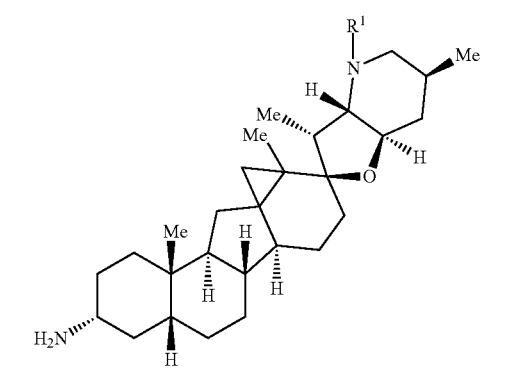

TABLE 5-continued

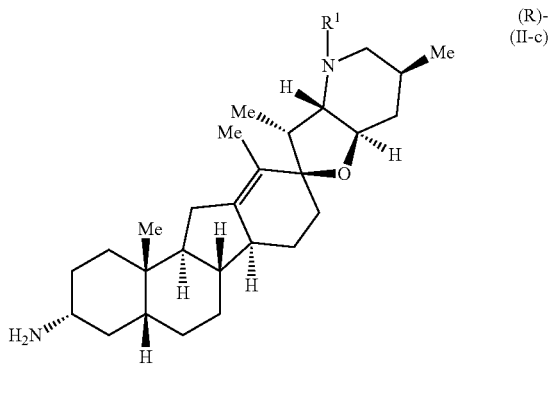
(R)-(II-c)

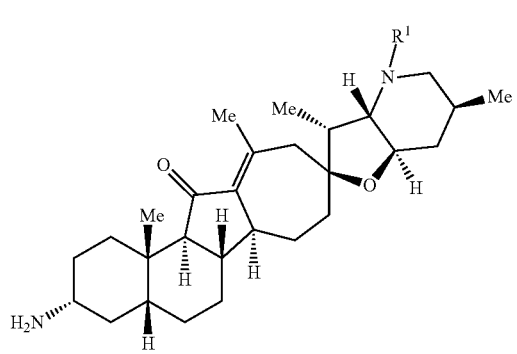
(R)-(II-d)

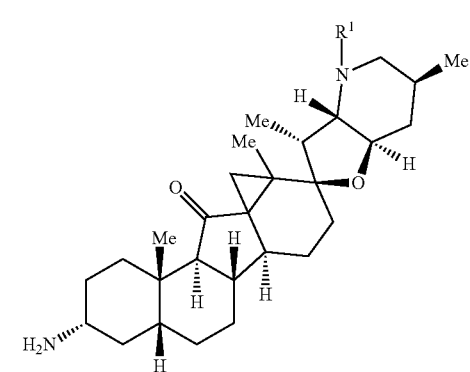
(R)-(II-e)

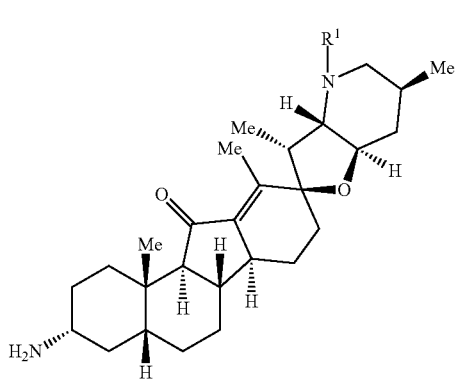
(R)-(II-f)

In certain embodiments, the compound of formula (I) is a compound of formula (I-a):

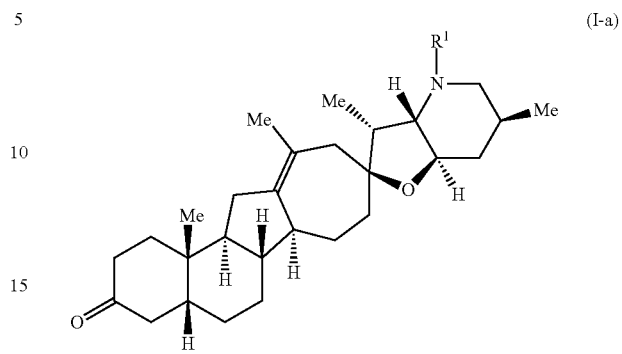
(I-a)

or salt thereof,
and the compound of formula (II) is a compound of formula (R)-(II-a):

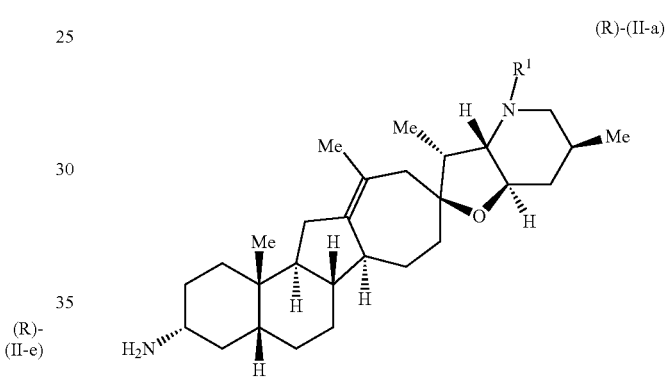
(R)-(II-a)

or a salt thereof,
wherein $R^1$ is as defined herein.
In certain embodiments, $R^1$ is H.
In certain embodiments, $R^1$ is aralkyl.
In certain embodiments, $R^1$ is $-CO_2R^{16}$. In certain embodiments, $R^1$ is $-CO_2R^{16}$ and $R^{16}$ is alkyl, alkenyl, alkynyl, aryl, cycloalkyl, heterocycloalkyl, aralkyl, heteroaryl or heteroaralkyl. In certain embodiments, $R^1$ is a -Boc group (e.g., wherein $R^1$ is $-CO_2R^{16}$ and $R^{16}$ is t-butyl). In certain embodiments, $R^1$ is a -CBz group (e.g., wherein $R^{16}$ is $-CO_2R^{16}$ and $R^{16}$ is benzyl).

Masked Ketones

In certain embodiments, the compound of formula (I) is a masked ketone. In this context, a "masked ketone" refers to a chemically modified compound of formula (I) or salt thereof containing a functional group which is transformed in situ (e.g., by hydrolysis) to the ketone.

Exemplary masked ketones include, but are not limited to, aminals and hemiaminals (see, for example, Vogel et al., *J. Org. Chem.* (2004) 69:4487-4491; Reeder and Meyers, *Tetrahedron Letters* (1999) 40:3115-3118, each of which is incorporated herein by reference), acetals and hemiacetals (see, for example, Boyce et al., *Bioorg. Med. Chem. Lett.* (2008) 18:5771-5773, incorporated herein by reference), hydrates (see, for example, Silverman et al., *J. Med. Chem.* (1987) 31:1566-1570, incorporated herein by reference), imines (see, for example, Hine et al., *J. Am. Chem. Soc.* (1970) 92:5194-5199, incorporated herein by reference), oximes (see, for example, Sha et al., *J. Am. Chem. Soc.* (2006) 128:9687-9692, incorporated herein by reference), thiocarbonyls (see, for example, Kalm, *J. Chem. Soc.* (1961) 2925-2929, incorporated herein by reference), thioacetals and thiohemiacetals (see, for example Ogura et al., *Tetrahedron Letters* (1986) 27:3665-3668, incorporated herein by reference), enol ethers (see for example, Manis and Rathke, *J. Org. Chem.* (1981) 46:5348-5351, incorporated herein by reference), and salts thereof.

For example, provided is a process for preparing a compound of formula (II):

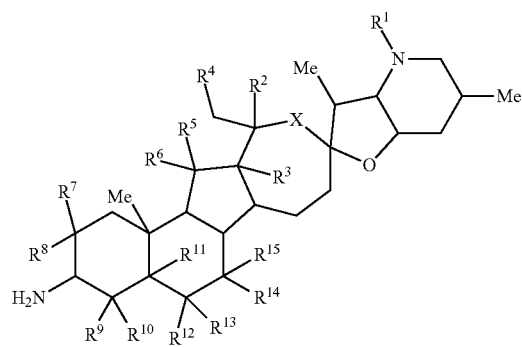

(II)

or a salt thereof;

from a masked ketone of a compound of formula (I):

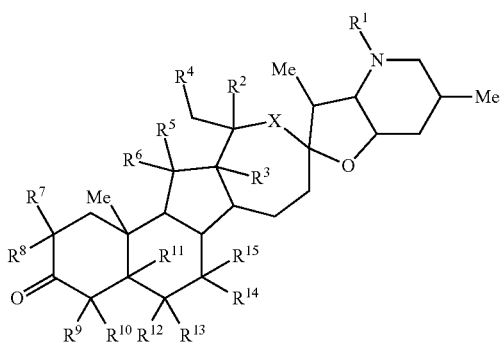

(I)

or salt thereof;

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and X are as defined herein;

the process comprising contacting a masked ketone of a compound of formula (I) or a salt thereof, an amino donor molecule, and an amine transaminase enzyme in a solution to provide a compound of formula (II) or a salt thereof.

In certain embodiments, a compound of formula (I) is a masked ketone having the formula (I-DD):

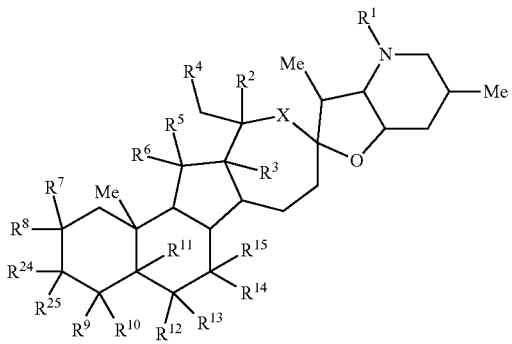

(I-DD)

or a salt thereof,
wherein:
$R^{24}$ and $R^{25}$ are selected from —$OR^{26}$, —$SR^{26}$, and —$N(R^{26})_2$,
or $R^{24}$ and $R^{25}$ are taken together to form the group =S, =N—$R^{26}$, or =N—$OR^{26}$,
or $R^{24}$ is —$OR^{27}$ or —O(C=O)$R^{27}$ and $R^{25}$ and $R^8$ or $R^{25}$ and $R^9$ are taken together to form a bond;
$R^{26}$ is H, alkyl, alkenyl, alkynyl, aryl, cycloalkyl, heterocycloalkyl, aralkyl, heteroaryl, heteroaralkyl, —C(=O)$R^{27}$, —C(=O)O$R^{27}$ or —C(=O)N($R^{28}$)$_2$, or any two occurrences of $R^{26}$ are taken together to form a 4-8 membered optionally substituted ring;
$R^{27}$ is alkyl, alkenyl, alkynyl, aryl, cycloalkyl, heterocycloalkyl, aralkyl, heteroaryl, or heteroaralkyl; and
$R^{28}$ is H, alkyl, alkenyl, alkynyl, aryl, cycloalkyl, heterocycloalkyl, aralkyl, heteroaryl, or heteroaralkyl; or any two occurrences of $R^{28}$ on the same substituent are taken together to form a 4-8 membered optionally substituted ring.

In certain embodiments, a compound of formula (I-DD) or a salt thereof, is a hydrate, an acetal or a hemiacetal.

In certain embodiments, a compound of formula (I-DD) or a salt thereof, is a hydrate, an acetal or a hemiacetal of the formula (I-EE):

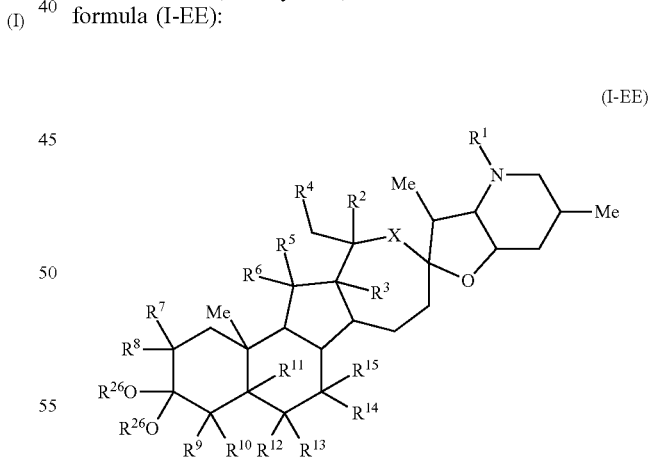

(I-EE)

or a salt thereof,
wherein:
$R^{26}$ is H, alkyl, alkenyl, alkynyl, aryl, cycloalkyl, heterocycloalkyl, aralkyl, heteroaryl, heteroaralkyl, —C(=O)$R^{27}$, —C(=O)O$R^{27}$ or —C(=O)N($R^{28}$)$_2$, or any two occurrences of $R^{26}$ are taken together to form a 4-8 membered optionally substituted ring;
$R^{27}$ is alkyl, alkenyl, alkynyl, aryl, cycloalkyl, heterocycloalkyl, aralkyl, heteroaryl, or heteroaralkyl; and $R^{28}$ is H, alkyl, alkenyl, alkynyl, aryl, cycloalkyl, heterocycloalkyl, aralkyl, heteroaryl, or heteroaralkyl; or any two occurrences of $R^{28}$ on the same substituent are taken together to form a 4-8 membered optionally substituted ring.

In certain embodiments, a compound of formula (I-DD) or a salt thereof, is a aminal or hemiaminal.

In certain embodiments, a compound of formula (I-DD), or a salt thereof, is a aminal or hemiaminal of the formula (I-FF):

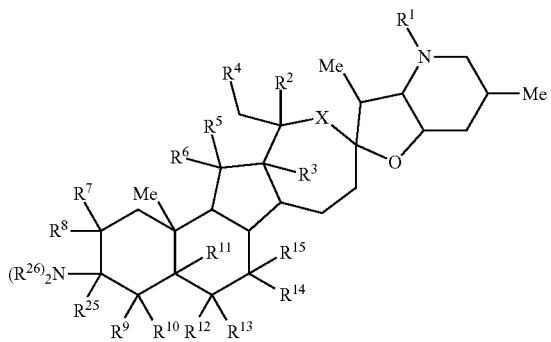

(I-FF)

or a salt thereof,
wherein:

$R^{25}$ is —$OR^{26}$ or —$N(R^{26})_2$;

$R^{26}$ is H, alkyl, alkenyl, alkynyl, aryl, cycloalkyl, heterocycloalkyl, aralkyl, heteroaryl, heteroaralkyl, —C(=O)$R^{27}$, —C(=O)O$R^{27}$ or —C(=O)N($R^{28}$)$_2$, or any two occurrences of $R^{26}$ are taken together to form a 4-8 membered optionally substituted ring;

$R^{27}$ is alkyl, alkenyl, alkynyl, aryl, cycloalkyl, heterocycloalkyl, aralkyl, heteroaryl, or heteroaralkyl; and $R^{28}$ is H, alkyl, alkenyl, alkynyl, aryl, cycloalkyl, heterocycloalkyl, aralkyl, heteroaryl, or heteroaralkyl; or any two occurrences of $R^{28}$ on the same substituent are taken together to form a 4-8 membered optionally substituted ring.

In certain embodiments, a compound of formula (I-DD) or a salt thereof, is a thioacetal or thiohemiacetal.

In certain embodiments, a compound of formula (I-DD) or a salt thereof, is a thioacetal or thiohemiacetal of the formula (I-GG):

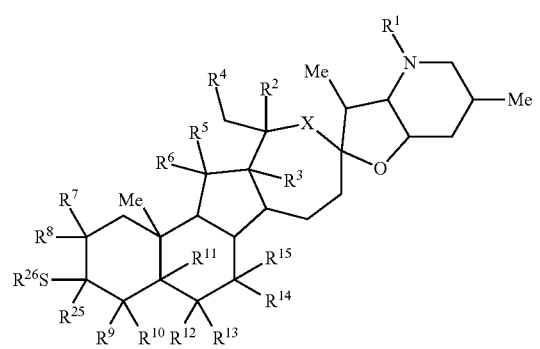

(I-GG)

or a salt thereof, wherein:
$R^{25}$ is —$OR^{26}$ or —$SR^{26}$;

$R^{26}$ is H, alkyl, alkenyl, alkynyl, aryl, cycloalkyl, heterocycloalkyl, aralkyl, heteroaryl, heteroaralkyl, —C(=O)$R^{27}$, —C(=O)O$R^{27}$ or —C(=O)N($R^{28}$)$_2$, or any two occurrences of $R^{26}$ are taken together to form a 4-8 membered optionally substituted ring;

$R^{27}$ is alkyl, alkenyl, alkynyl, aryl, cycloalkyl, heterocycloalkyl, aralkyl, heteroaryl, or heteroaralkyl; and $R^{28}$ is H, alkyl, alkenyl, alkynyl, aryl, cycloalkyl, heterocycloalkyl, aralkyl, heteroaryl, or heteroaralkyl; or any two occurrences of $R^{28}$ on the same substituent are taken together to form a 4-8 membered optionally substituted ring.

In certain embodiments, a compound of formula (I-DD) or a salt thereof, is an imine.

In certain embodiments, a compound of formula (I-DD) or a salt thereof, is an imine of the formula (I-HH):

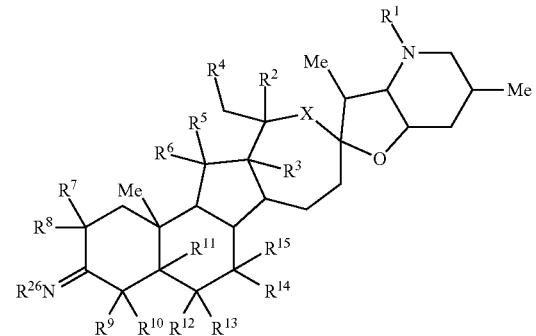

(I-HH)

or a salt thereof,
wherein:

$R^{26}$ is H, alkyl, alkenyl, alkynyl, aryl, cycloalkyl, heterocycloalkyl, aralkyl, heteroaryl, heteroaralkyl, —C(=O)$R^{27}$, —C(=O)O$R^{27}$ or —C(=O)N($R^{28}$)$_2$;

$R^{27}$ is alkyl, alkenyl, alkynyl, aryl, cycloalkyl, heterocycloalkyl, aralkyl, heteroaryl, or heteroaralkyl; and $R^{28}$ is H, alkyl, alkenyl, alkynyl, aryl, cycloalkyl, heterocycloalkyl, aralkyl, heteroaryl, or heteroaralkyl; or any two occurrences of $R^{28}$ on the same substituent are taken together to form a 4-8 membered optionally substituted ring.

In certain embodiments, a compound of formula (I-DD) or a salt thereof, is an oxime.

In certain embodiments, a compound of formula (I-DD) or a salt thereof, is an oxime of the formula (I-JJ):

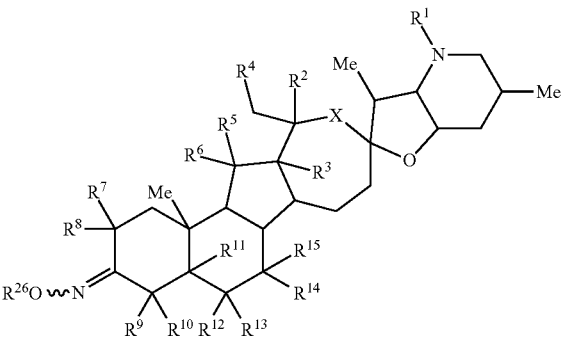

(I-JJ)

or a salt thereof, wherein:

$R^{26}$ is H, alkyl, alkenyl, alkynyl, aryl, cycloalkyl, heterocycloalkyl, aralkyl, heteroaryl, heteroaralkyl, —C(=O)$R^{27}$, —C(=O)O$R^{27}$ or —C(=O)N($R^{28}$)$_2$;

$R^{27}$ is alkyl, alkenyl, alkynyl, aryl, cycloalkyl, heterocycloalkyl, aralkyl, heteroaryl, or heteroaralkyl; and $R^{28}$ is H, alkyl, alkenyl, alkynyl, aryl, cycloalkyl, heterocycloalkyl, aralkyl, heteroaryl, or heteroaralkyl; or any two occurrences of $R^{28}$ on the same substituent are taken together to form a 4-8 membered optionally substituted ring.

In certain embodiments, a compound of formula (I-DD) or a salt thereof, is a thiocarbonyl.

In certain embodiments, a compound of formula (I-DD) or a salt thereof, is a thiocarbonyl of the formula (I-KK):

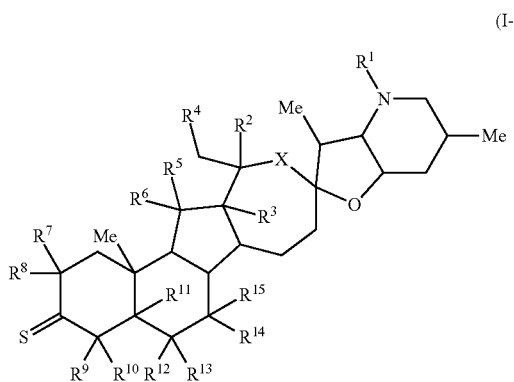

(I-KK)

or a salt thereof.

In certain embodiments, a compound of formula (I-DD) or a salt thereof, is an enol ether.

In certain embodiments, a compound of formula (I-DD) or a salt thereof, is an enol ether of the formulae (I-LL) or (I-MM):

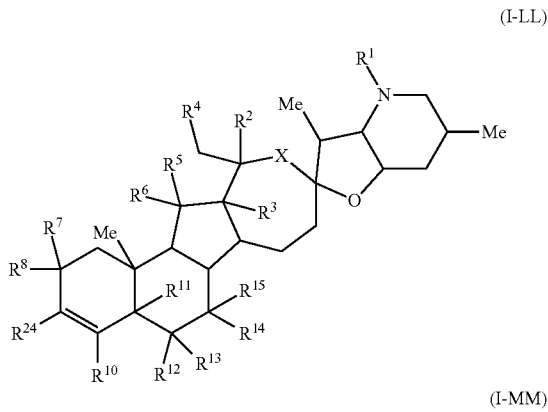

(I-LL)

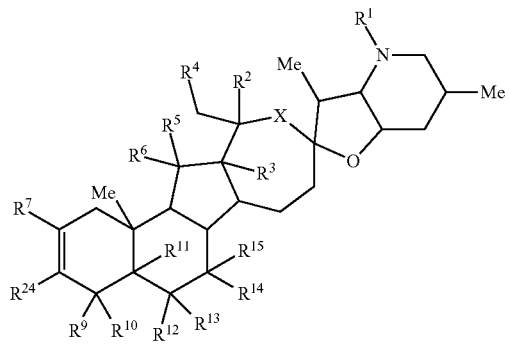

(I-MM)

or a mixture thereof and/or a salt thereof, wherein $R^{24}$ is —O$R^{27}$ or —O(C=O)$R^{27}$ and $R^{27}$ is alkyl, alkenyl, alkynyl, aryl, cycloalkyl, heterocycloalkyl, aralkyl, heteroaryl, or heteroaralkyl.

Amino Donor Molecule

An "amino donor molecule" is a compound having an —NH$_2$ group which, during the course of the reaction, is transferred to the compound of formula (I). Amino donor molecules include both amines and amino acids.

In certain embodiments, the amino donor molecule is an amine or salt thereof (e.g., a primary amine). Exemplary amine include, but are not limited to, pyridoxamine, methylbenzylamine, 2-aminobutane, propyl amine, isopropyl amine, 1,1,1-trifluoropropan-2-amine, 1,1,1,3,3,3-hexafluoropropan-2-amine, benzyl amine, 2-amino-1-butanol, 1-amino-1-phenylethane, 1-amino-1-(2-methoxy-5-fluorophenyl)ethane, 1-amino-1-phenylpropane, 1-amino-1-(4hydroxyphenyl)propane, 1-amino-1-(4-bromophenyl)propane, 1-amino-1-(4-nitrophenyl)propane, 1-phenyl-2-aminopropane, 1-(3-trifluoromethylphenyl)-2-aminopropane, 2-aminopropanol, 1-amino-1-phenylbutane, 1-phenyl-2-aminobutane, 1-(2,5-dimethoxy-4-methylphenyl)-2-aminobutane, 1-phenyl-3-aminobutane, 1-(4-hydroxyphenyl)-3-aminobutane, 1-amino-1-(2-naphthyl)ethane, cis-2-methylcyclopentanamine, trans-2-methylcyclopentanamine, cis-3-methylcyclopentanamine, trans-3-methylcyclopentanamine, cis-2-ethylcyclopentanamine, trans-2-ethylcyclopentanamine, cis-3-ethylcyclopentanamine, trans-3-ethylcyclopentanamine, cis-2-methylcyclohexanamine, trans-2-methylcyclohexanamine, cis-3-methylcyclohexanamine, trans-3-methylcyclohexanamine, cis-2-ethylcyclohexanamine, trans-2-ethylcyclohexanamine, cis-3-ethylcyclohexanamine, trans-3-ethylcyclohexanamine, 1-aminotetralin, 2-aminotetralin, 2-amino-5-methoxytetralin, 1-aminoindane, 2-aminoindane, 2-amino-1-propanol, cis-1-amino-2-indanol, trans-1-amino-2-indanol, 1-amino-6-hydroxyindanamine, taurine, and salts thereof.

In certain embodiments, the amino donor molecule is an amino acid or a polypeptide thereof and/or a salt thereof. A polypeptide, as used herein, refers to two or more amino acids joined by a peptide bond. In certain embodiments, the polypeptide is a dipeptide (e.g., two amino acids joined by a peptide bond).

In certain embodiments, the amino acid is selected from glycine, alanine, aspartic acid, phenylalanine, 2-aminopentanedioic acid, 3-aminobutyrate, γ-aminobutyrate, β-alanine, asparagine, cysteine, glutamic acid, glutamine, proline, selenocysteine, serine, tyrosine, arginine, histidine, ornithine, isoleucine, leucine, lysine, methionine, threonine, tryptophan, valine, and polypeptides thereof and/or salts thereof.

In certain embodiments, the amino donor molecule is a chiral amino donor molecule or a salt thereof, e.g., an amino donor molecule containing at least one asymmetric center. In certain embodiments, the amino group (—NH$_2$) to be transferred is attached to a chiral carbon. In certain embodiments, the chiral carbon has (R)-stereochemistry. In certain embodiments, the chiral carbon has (S)-stereochemistry.

In certain embodiments, the chiral amino donor molecule is a chiral amine or a salt thereof, e.g., an amine containing at least one asymmetric center. Exemplary chiral amines include, but are not limited to, (R)-methylbenzylamine, (S)-methylbenzylamine, (S)-2-aminobutane, (R)-2-aminobutane, (S)-1-aminoindane, (R)-1-aminoindane, (R)-1,1,1-trifluoropropan-2-amine, (S)-1,1,1-trifluoropropan-2-amine, (R)-2-amino-1-propanol, (S)-2-amino-1-propanol, (1R,2S)-cis-1-amino-2-indanol, (1R,2R)-trans-1-amino-2-indanol, 1-(R)-amino-6-hydroxyindanamine, 1-(S)-amino-6-hydroxyindanamine, (R)-2-amino-1-butanol, (S)-2-amino-1-butanol, (R)-1-amino-1-phenylethane, (S)-1-amino-1-phenylethane, (R)-1-amino-1-(2-methoxy-5-fluorophenyl)ethane, (S)-1-amino-1-(2-methoxy-5-fluorophenyl)ethane, (R)-1-amino-1-phenylpropane, (S)-1-amino-1-phenylpropane, (R)-1-amino-1-(4-hydroxyphenyl)-propane, (S)-1-amino-1-(4-hydroxyphenyl)-propane, (R)-1-amino-1-(4-bromophenyl)propane, (S)-1-amino-1-(4-bromophenyl)propane, (R)-1-amino-1-(4-nitrophenyl)propane, (S)-1-amino-1-(4-nitrophenyl)propane, (R)-1-phenyl-2-aminopropane, (S)-1-phenyl-2-aminopropane, (R)-1-(3-trifluoromethylphenyl)-2-aminopropane, (S)-1-(3-trifluoromethylphenyl)-2-aminopropane (R)-1-amino-1-phenylbutane, (S)-1-amino-1-phenylbutane, (R)-1-phenyl-2-aminobutane, (S)-1-phenyl-2-aminobutane, (R)-1-(2,5-dimethoxy-4-methylphenyl)-2-aminobutane, (S)-1-(2,5-dimethoxy-4-methylphenyl)-2-aminobutane, (R)-1-phenyl-3-aminobutane, (S)-1-phenyl-3-aminobutane, (R)-1-(4-hydroxyphenyl)-3-aminobutane, (S)-1-(4-hydroxyphenyl)-3-aminobutane, (R)-1-amino-1-(2-naphthyl)ethane, (S)-1-amino-1-(2-naphthyl)ethane (R)-1-aminotetralin, (S)-1-aminotetralin, (R)-2-aminotetralin, (S)-2-aminotetralin, (R)-2-amino-5-methoxytetralin, (S)-2-amino-5-methoxytetralin, (1R,2S)-cis-2-methylcyclopentanamine, (1S,2R)-cis-2-methylcyclopentanamine, (1R,2R)-trans-2-methylcyclopentanamine, (1S,2S)-trans-2-methylcyclopentanamine, (1R,3S)-cis-3-methylcyclopentanamine, (1S,3R)-cis-3-methylcyclopentanamine, (1R,3R)-trans-3-methylcyclopentanamine, (1S,3S)-trans-3-methylcyclopentanamine, (1R,2S)-cis-2-ethylcyclopentanamine, (1S,2R)-cis-2-ethylcyclopentanamine, (1R,2R)-trans-2-ethylcyclopentanamine, (1S,2S)-trans-2-ethylcyclopentanamine, (1R,3S)-cis-3-ethylcyclopentanamine, (1S,3R)-cis-3-ethylcyclopentanamine, (1R,3R)-trans-3-ethylcyclopentanamine, (1S,3S)-trans-3-ethylcyclopentanamine, (1R,2S)-cis-2-methylcyclohexanamine, (1S,2R)-cis-2-methylcyclohexanamine, (1R,2R)-trans-2-methylcyclohexanamine, (1S,2S)-trans-2-methylcyclohexanamine, (1R,3S)-cis-3-methylcyclohexanamine, (1S,3R)-cis-3-methylcyclohexanamine, (1R,3R)-trans-3-methylcyclohexanamine, (1S,3S)-trans-3-methylcyclohexanamine, (1R,2S)-cis-2-ethylcyclohexanamine, (1S,2R)-cis-2-ethylcyclohexanamine, (1R,2R)-trans-2-ethylcyclohexanamine, (1S,2S)-trans-2-ethylcyclohexanamine, (1R,3S)-cis-3-ethylcyclohexanamine, (1S,3R)-cis-3-ethylcyclohexanamine, (1R,3R)-trans-3-ethylcyclohexanamine, (1S,3S)-trans-3-ethylcyclohexanamine, and salts thereof.

In certain embodiments, the chiral amino donor molecule is a chiral amino acid or a polypeptide thereof and/or a salt thereof, e.g., containing at least one asymmetric center. Exemplary chiral amino acids include, but are not limited to, (L)-alanine, (D)-alanine, (L)-aspartic acid, (D)-aspartic acid, (L)-phenylalanine, (D)-phenylalanine, (2S)-2-aminopentanedioic acid, (L)-asparagine, (D)-asparagine, (L)-cysteine, (D)-cysteine, (L)-glutamine, (D)-glutamine, (L)-glutamic acid, (D)-glutamic acid, (L)-proline, (D)-proline, (L)-selenocysteine, (D)-selenocysteine, (L)-serine, (D)-serine, (L)-tyrosine, (D)-tyrosine, (L)-arginine, (D)-arginine, (L)-histidine, (D)-histidine, (L)-isoleucine, (D)-isoleucine, (L)-leucine, (D)-leucine, (L)-lysine, (D)-lysine, (L)-methionine, (D)-methionine, (L)-threonine, (D)-threonine, (L)-tryptophan, (D)-tryptophan, (L)-valine, (D)-valine, (L)-ornithine, (D)-ornithine, (3R)-aminobutyrate, (3S)-aminobutyrate and polypeptides thereof and/or salts thereof.

In certain embodiments, the chiral amino donor molecule is (R)-methylbenzylamine or a salt thereof. In other embodiments, the chiral amino donor molecule is (S)-methylbenzylamine or a salt thereof.

In certain embodiments, the chiral amino donor molecule is (L)-alanine or a salt thereof.

In certain embodiments, the chiral amino donor molecule is (D)-alanine or a salt thereof.

In certain embodiments, the chiral amino donor molecule is (S)-1-aminoindane. In certain embodiments, the chiral amino donor molecule is (R)-1-aminoindane.

In certain embodiments, the process comprises contacting a compound of formula (I), a chiral amino donor molecule, and an amine transaminase enzyme in a solution to provide a compound of formula (II), or a salt thereof, with the newly-formed amino group having (S) stereochemistry.

In certain embodiments, the process comprises contacting a compound of formula (I), or a salt thereof, a chiral amino donor molecule, and an amine transaminase enzyme in a solution to provide a compound of formula (II), or a salt thereof, with the newly-formed amino group having (R) stereochemistry.

Amine Transaminase (ATA) Enzyme

An amine transaminase (ATA) enzyme catalyzes the transfer of the —NH$_2$ group from the amino donor molecule to a compound having a ketone functional group, e.g., a compound of formula (I), in order to provide a compound of formula (II).

In certain embodiments, the amine transaminase enzyme preferentially generates a compound of formula (II), or a salt thereof, with the newly-formed amino group having (R) or (S) stereochemistry. As used herein, "preferentially generates" refers to the production of one stereoisomer of a compound of formula (II) in excess over the other stereoisomer.

In certain embodiments, the amine transaminase enzyme preferentially generates a compound of formula (II), or a salt thereof, with the newly-formed amino group having (R) stereochemistry.

In certain embodiments, the amine transaminase enzyme preferentially generates a compound of formula (II), or a salt thereof, with the newly-formed amino group having (S) stereochemistry.

In certain embodiments, the amine transaminase enzyme preferentially generates a compound of formula (II), or a salt thereof, with the newly-formed amino group having (R) or (S) stereochemistry, in greater than 40% diastereomeric excess (de), greater than 50% de, greater than 60% de, greater than 70% de, greater than 75% de, greater than 80% de, greater than 85% de, greater than 90% d e, greater than 95% d e, greater than 98% d e, or greater than 99% de, as determined by HPLC.

In certain embodiments, the amine transaminase enzyme preferentially generates an enantiomerically pure compound of formula (II), or salt thereof.

In certain embodiments, the amine transaminase enzyme is an omega amine transaminase enzyme, a broad-range transaminase, a glutamate-pyruvate transaminase or a glutamate-oxaloacetic transaminase.

In certain embodiments, the amine transaminase enzyme is an omega amine transaminase enzyme.

Exemplary omega amine transaminase enzymes include, but are not limited to, omega amine transaminase enzymes from Codexis, Inc. (Redwood City, Calif.), such as ATA-101, ATA-102, ATA-103, ATA-104, ATA-105, ATA-106, ATA-107, ATA-108, ATA-109, ATA-110, ATA-113, ATA-114, ATA-115, ATA-116, ATA-117 and ATA-124; omega amine transaminases from *Vibrio fluvialis, Alcaligenes denitrificans, Klebsiella pneumoniae*, or *Bacillus thuringiensis*, such as is described in WO 2007093372, incorporated herein by reference; omega amine transaminases from *Chromobac-*

*terium violaceum*, such as is described in Smithies et al., *Tetrahedron Asymmetry* (2009) 570-574, incorporated herein by reference, omega amine transaminases from *Bacillus cereus*, such as is described in Nakano et al., J. Biochem. (1977) 81:1375-1381, incorporated herein by reference, and omega amine transaminases from *Arthrobactercitreus*, such as described in Cassimjee et al., ChemComm (2010) 46:5569-5571, incorporated herein by reference.

Other suitable exemplary omega amine transaminases which may be used according to the present invention are described in Iwa-saki et al., *Biotechnol. Lett.* (2003) 25:1843-1846; Shin et al., *Biotechnol. Bioeng.* (1997) 55:348-358; Shin and Kim, *Biosc. Biotechnol. Biochem.* (2001) 65:1782-1788; Koszelewski et al., *Trends in Biotechnology* (2010) 28:324-332, and Shin and Kim, *Biotechnol. Bioeng.* (1998) 60:534-540, each of which is incorporated herein by reference.

Immobilization of the amine transaminase enzyme can also be effective to improve the stability of the enzyme which in turn will allow its re-use, thereby making the process more economical. Immobilization of the enzymes has been achieved by a simple adsorption onto a hydrophobic resin or by intermolecular covalent cross-linking of enzymes with a variety of functional groups or finally by incorporating enzymes into the lattice of a polymer matrix or a membrane. Covalent immobilization of the omega amine transaminase from *Vibrio fluvialis* JS17 has been reported by Lee and co-workers where the authors adsorb the enzyme on chitosan beads and subsequently cross linked with glutaraldehyde (Yi et al., *Proc. Biochem.* (2007) 42:895-898, incorporated herein by reference). The immobilized amine transaminase enzyme on chitosan beads retained ca. 77% of its activity after five consecutive reactions with the substrate indicating the utility of the process.

In certain embodiments, the omega amine transaminase enzyme is an amine transaminase enzyme from Codexis, Inc.

In certain embodiments, the omega amine transaminase enzyme is ATA-113.

In certain embodiments, the omega amine transaminase enzyme is ATA-117.

In certain embodiments, the omega amine transaminase enzyme is an omega amine transaminase from *Vibrio fluvialis*.

In certain embodiments, the omega amine transaminase enzyme is an omega amine transaminase from *Alcaligenes denitrificans*.

In certain embodiments, the omega amine transaminase enzyme is an omega amine transaminase from *Arthrobactercitreus*.

In certain embodiments, the omega amine transaminase enzyme is an omega amine transaminase from *Klebsiella pneumoniae*.

In certain embodiments, the omega amine transaminase enzyme is an omega amine transaminase from *Bacillus thuringiensis*.

In certain embodiments, the omega amine transaminase enzyme is an omega amine transaminase from *Bacillus cereus*.

In certain embodiments, the omega amine transaminase enzyme is an omega amine transaminase from *Chromobacterium violaceum*.

In certain embodiments, the omega amine transaminase enzyme is an immobilized omega amine transaminase enzyme.

Co-Factors

In certain embodiments, the process further comprises adding a co-factor to the solution. Co-factors include prosthetic groups which are bound to an enzyme during the enzymatic reaction, and co-enzymes which act to transfer chemical groups during the enzymatic reaction.

Exemplary co-factors include the prosthetic group pyridoxal phosphate (PLP) and co-enzymes such as L-alanine dehydrogenase (LADH), lactate dehydrogenase (LDH), nicotinamide adenine dinucleotide phosphate (NADPH), nicotinamide adenine dinucleotide (NAD), formate dehydrogenase (FDH) and glucose dehydrogenase (GDH).

In certain embodiments, the process further comprises adding the co-factor pyridoxal phosphate (PLP) to the solution.

In certain embodiments, the amine transaminase enzyme and the co-factor pyridoxal phosphate added to the solution are pre-complexed before contacting with the compound of formula I. In other embodiments, the amine transaminase (ATA) enzyme and pyridoxal phosphate added to the solution are not pre-complexed before contacting with the compound of formula I (i.e., each is individually added to the solution).

In certain embodiments, the process further comprises adding a co-enzyme to the solution.

In certain embodiments, the process further comprises adding one or more co-enzymes selected from L-alanine dehydrogenase (LADH), lactate dehydrogenase (LDH), nicotinamide adenine dinucleotide phosphate (NADPH), nicotinamide adenine dinucleotide (NAD), formate dehydrogenase (FDH), and glucose dehydrogenase (GDH) to the solution.

In certain embodiments, the process further comprises adding the co-enzyme LADH to the solution.

In certain embodiments, the process further comprises adding the co-enzyme FDH to the solution.

In certain embodiments, the process further comprises adding the co-enzyme NAD to the solution.

In certain embodiments, the process further comprises adding the co-enzyme LDH to the solution.

In certain embodiments, the process further comprises adding the co-enzyme GDH to the solution.

In certain embodiments, the process further comprises adding a mixture of LADH, FDH and NAD to the solution.

In certain embodiments, the process further comprises adding a mixture of co-enzymes LDH, GDH and NAD to the solution.

In certain embodiments, the process further comprises adding a sugar to the solution. In certain embodiments, the sugar is glucose.

In certain embodiments, process further comprises adding a pyruvate reductase mix to the solution. In certain embodiments, the process further comprises adding a mixture of co-enzymes LDH, GDH, NAD, and the sugar glucose (e.g., for example, pyruvate reductase mix PRM-102, available from Codexis, Inc.) to the solution.

In certain embodiments, the process further comprises adding ammonia or an ammonium salt to the solution. In certain embodiments, the ammonium salt is ammonium formate ($NH_4CO_2H$). Ammonium formate can be obtained in situ from the combination of formic acid and ammonia.

Other Reaction Conditions

In certain embodiments, the solution comprises an aqueous solution.

In certain embodiments, the aqueous solution is a buffered aqueous solution. Exemplary buffers include, but are not limited to, 3-{[tris(hydroxymethyl)methyl]amino}propanesulfonic acid (TAPS), N,N-bis(2-hydroxyethyl)glycine (Bicine), tris(hydroxymethyl)methylamine (Tris), N-tris(hydroxymethyl)methylglycine (Tricine), 4-2-hydroxyethyl-1-piperazineethanesulfonic acid (HEPES), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate), 2-(N-morpholino)ethanesulfonic acid (MES), carbonic acid, phosphate buffered saline (PBS), acetate, sodium phosphate, and salts thereof.

In certain embodiments, the buffered aqueous solution is a sodium phosphate buffered solution.

In certain embodiments, the solution further comprises a co-solvent. In certain embodiments, the co-solvent is an organic solvent.

In certain embodiments, the organic solvent is water miscible. In certain embodiments, the organic solvent is water immiscible.

In certain embodiments, the solution is a monophasic system, e.g., comprising an aqueous solution and one or more water miscible organic solvents. Suitable water miscible organic solvents include, but are not limited to, organic alcohols (e.g., methanol (MeOH), ethanol (EtOH), isopropanol (iPrOH) and 2,2,2-trifluoroethanol ($CF_3CH_2OH$)), dimethylsulfoxide (DMSO), dimethylformamide (DMF), glycols (e.g., ethylene glycol and propylene glycol), and mixtures thereof.

In certain embodiments, the solution comprises an aqueous solution and an organic alcohol. In certain embodiments, the solution comprises an aqueous solution and methanol.

However, in other embodiments, the solution is a biphasic system, e.g., comprising an aqueous solution and one or more water immiscible organic solvents. Suitable water immiscible organic solvents include, but are not limited to, alkanes (e.g., hexane, heptane, perfluorohexane), esters (e.g., ethyl acetate (EtOAc), isopropyl acetate (iPrOAc)), ketones (e.g., cyclohexanone), ethers (e.g., 2-methyl tetrahydrofuran), and aromatic hydrocarbons (e.g., toluene, xylenes, benzene).

In certain embodiments, the pH of the solution is between about 5 and about 9, between about 5 and about 8, between about 6 and about 8, between about 7 and about 8, between about 7 and about 7.5, or between about 7.5 and about 8.

In certain embodiments, the pH is of the solution is less than about 9, less than about 8.5, or less than about 8. In certain embodiments, the pH of the solution is about 7. In certain embodiments, the pH of the solution is about 7.5. In certain embodiments, the pH of the solution is about 8.

In certain embodiments, the temperature of the solution is at least about 20° C., at least about 25° C., at least about 30° C., or at least about 35° C. In certain embodiments, the temperature of the solution is between about 20° C. and about 50° C.

In certain embodiments, the process further comprises a resin. Adsorption of the ketone starting material (I) or the product amine (II) to the resin reduces their respective concentration in the reaction medium, and thus reduces their propensity to inhibit the enzyme. Exemplary resins include, but are not limited to, Amberlite™, Amberlyst™ and Dowex™ resins.

In certain embodiments, the process further comprises a solublizer such as a cyclodextrin or a surfactant. Exemplary cyclodextrins include, but are not limited to, β-cyclodextrins and γ-cyclodextrins. Exemplary surfactants include, but are not limited to sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), polyoxyethylene ethers, (e.g. polyoxyethylene lauryl ether [Brij 30]), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, and/or combinations thereof.

In certain embodiments, the process further comprises a sulfate (e.g., for example, sodium bisulfate). For example, when benzylamine is used as the amino donor molecule, sodium bisulfate reacts with the by-product benzaldehyde to form an insoluble bisulfite adduct.

In certain embodiments, the process further comprises a dehydrogenase enzyme (e.g., a yeast alcohol dehydrogenase (YADH) such as from *Saccharomyces cerevisiae*). For example, when isopropyl amine is used as the amino donor molecule, a YADH enzyme converts the acetone by-product to isopropanol, thereby shifting the equilibrium and driving the reaction to completion (see Cassimjee et al., *Chem Comm* (2010) 46:5569-5571, incorporated herein by reference).

Additional Embodiments

In certain embodiments, provided is a process for preparing a compound of formula (R)-(II-a):

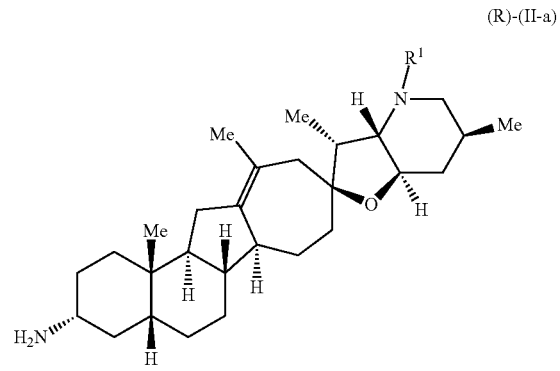

(R)-(II-a)

or a salt thereof;
from a compound of formula (I-a):

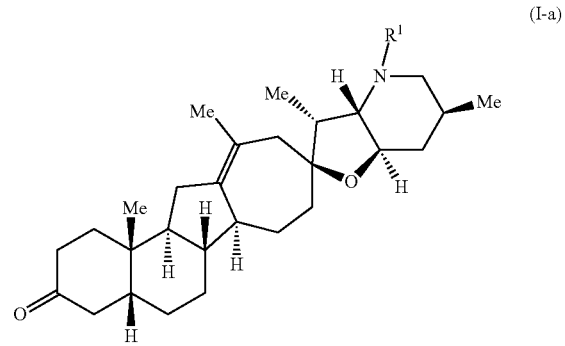

(I-a)

or a salt thereof;

wherein:

$R^1$ is H, aralkyl, or $-CO_2R^{16}$;

$R^{16}$ is H, alkyl, alkenyl, alkynyl, aryl, cycloalkyl, heterocycloalkyl, aralkyl, heteroaryl, heteroaralkyl or $-[C(R^{20})_2]_p-R^{21}$ wherein p is 0-6;

$R^{20}$ is H, alkyl, alkenyl, alkynyl, aryl, cycloalkyl, heterocycloalkyl, aralkyl, heteroaryl, or heteroaralkyl; or any two occurrences of $R^{20}$ on the same substituent are taken together to form a 4-8 membered optionally substituted ring;

$R^{21}$ is $-OR^{22}$, $-N(R^{22})C(=O)R^{22}$, $-N(R^{22})C(=O)OR^{22}$, $-N(R^{22})SO_2(R^{22})$, $-C(=O)R^{22}N(R^{22})_2$, $-OC(=O)R^{22}N(R^{22})(R^{22})$, $-SO_2N(R^{22})(R^{22})$, $-N(R^{22})(R^{22})$, $-C(=)OR^{22}$, $-C(=O)N(OH)(R^{22})$, $-OS(O)_2OR^{22}$, $-S(O)_2OR^{22}$, $-OP(=O)(OR^{22})(OR^{22})$, $-N(R^{22})P(O)(OR^{22})(OR^{22})$, or $-P(=O)(OR^{22})(OR^{22})$; and $R^{22}$ is H, alkyl, alkenyl, alkynyl, aryl, cycloalkyl, heterocycloalkyl, aralkyl, heteroaryl, heteroaralkyl; or any two occurrences of $R^{22}$ on the same substituent are taken together to form a 4-8 membered optionally substituted ring;

the process comprising contacting a compound of formula (I-a) or a salt thereof, an amino donor molecule, and an amine transaminase enzyme in a solution to provide a compound of formula (R)-(II-a) or a salt thereof.

In certain embodiments, $R^1$ is H, aralkyl, or $-CO_2R^{16}$.

In certain embodiments, $R^1$ is H.

In certain embodiments, $R^1$ is aralkyl.

In certain embodiments, $R^1$ is $-CO_2R^{16}$. In certain embodiments, $R^1$ is $-CO_2R^{16}$ and $R^{16}$ is alkyl, alkenyl, alkynyl, aryl, cycloalkyl, heterocycloalkyl, aralkyl, heteroaryl or heteroaralkyl. In certain embodiments, $R^1$ is a -Boc group (e.g., wherein $R^1$ is $-CO_2R^{16}$ and $R^{16}$ is t-butyl). In certain embodiments, $R^1$ is a -CBz group (e.g., wherein $R^1$ is $-CO_2R^{16}$ and $R^{16}$ is benzyl).

In certain embodiments, the amino donor molecule is a chiral amino donor molecule. In certain embodiments, the chiral amino donor molecule is (R)-methylbenzylamine or a salt thereof. In other embodiments, the chiral amino donor molecule is (S)-methylbenzylamine or a salt thereof.

In certain embodiments, the chiral amino donor molecule is (L)-alanine or a salt thereof.

In certain embodiments, the chiral amino donor molecule is (D)-alanine or a salt thereof.

In certain embodiments, the amine transaminase enzyme is an omega amine transaminase enzyme. In certain embodiments, the omega amine transaminase enzyme is ATA-113 from Codexis, Inc. In certain embodiments, the omega amine transaminase enzyme is ATA-117 from Codexis, Inc. In certain embodiments, the omega amine transaminase enzyme is an omega amine transaminase from *Vibrio fluvialis*.

Additional Steps

In certain embodiments, the process further comprises contacting a compound of formula (II):

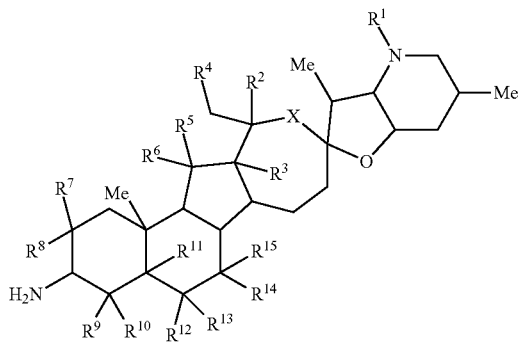

or a salt thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and X are as defined herein, with a sulfonylating agent to provide a compound of formula (III):

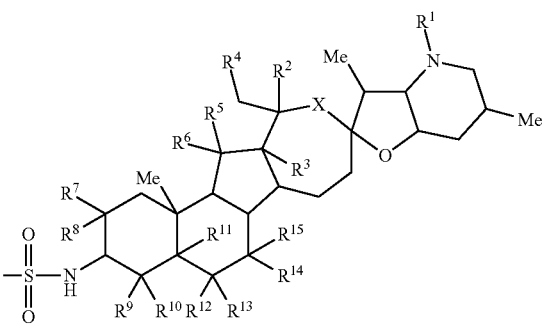

or a salt thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and X are as defined herein, and $R^{23}$ is alkyl or aryl.

Exemplary sulfonylating agents include, but are not limited to, benzenesulfonyl chloride, benzenesulfonyl anhydride, p-toluenesulfonyl chloride, p-toluenesulfonyl anhydride, methanesulfonyl chloride, and methanesulfonyl anhydride.

In certain embodiments, the sulfonylating agent is benzenesulfonyl chloride or benzenesulfonyl anhydride, and $R^{23}$ is benzenyl (i.e., $-C_6H_5$).

In certain embodiments, the sulfonylating agent is p-toluenesulfonyl chloride or p-toluenesulfonyl anhydride, and $R^{23}$ is toluenyl (i.e., $-C_6H_4(p-CH_3)$).

In certain embodiments, the sulfonylating agent is methanesulfonyl chloride or methanesulfonyl anhydride, and $R^{23}$ is methyl (i.e., $-CH_3$).

In certain embodiments, the compound of formula (II) is:

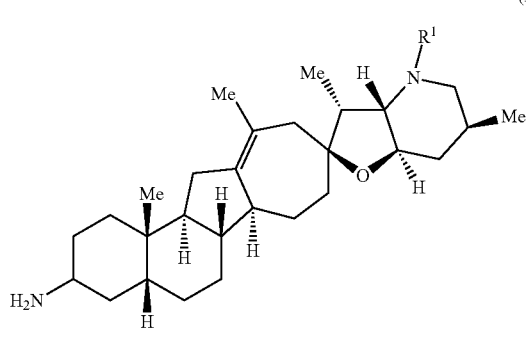

or a salt thereof, and the compound of formula (III) is:

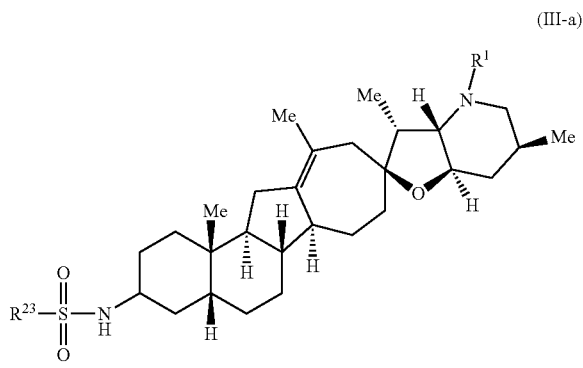

(III-a)

or a salt thereof,
wherein $R^1$ and $R^{23}$ are as defined herein.
In certain embodiments, the compound of formula (II) is:

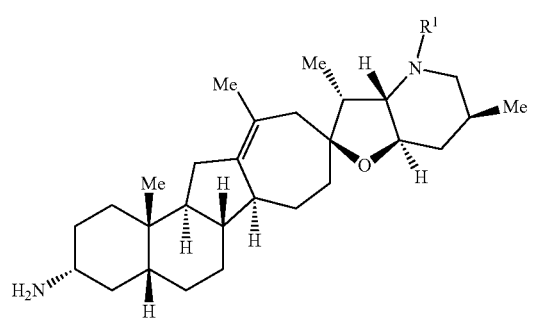

(R)-(II-a)

or a salt thereof,
and the compound of formula (III) is:

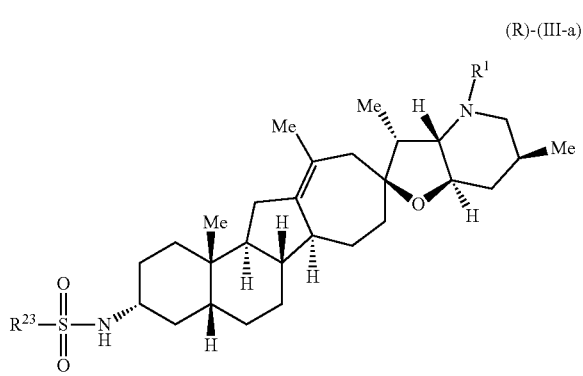

(R)-(III-a)

or a salt thereof,
wherein $R^1$ and $R^{23}$ are as defined herein.
In certain embodiments, $R^1$ is H.
In certain embodiments, $R^1$ is aralkyl.
In certain embodiments, $R^1$ is —$CO_2R^{16}$.
In certain embodiments wherein $R^1$ is aralkyl or —$CO_2R^{16}$, the process further comprises deprotecting the compound of formula (III) wherein $R^1$ is aralkyl or —$CO_2R^{16}$ to provide a compound of formula (III) wherein $R^1$ is H. Exemplary deprotection methods include, but are not limited to, reducing conditions, such as hydrogenation.

For example, in certain embodiments, the process further comprises deprotecting the compound of formula (R)-(III-a):

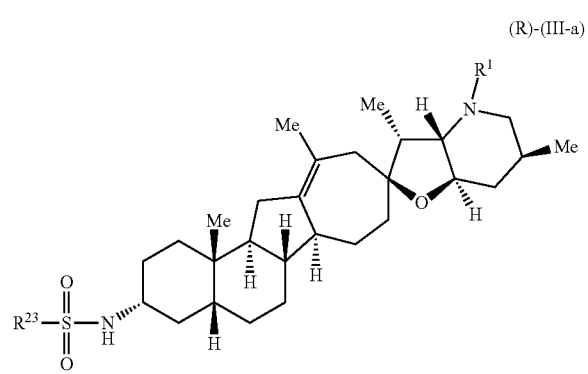

(R)-(III-a)

or salt thereof,
wherein $R^1$ is aralkyl or —$CO_2R^{16}$,
to provide a compound of formula (R)-(III-b):

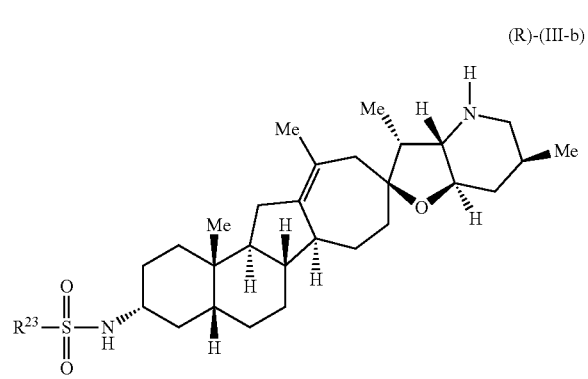

(R)-(III-b)

or salt thereof,
wherein $R^{23}$ is as defined herein.

EXEMPLIFICATION

The present disclosure now being generally described, it will be more readily understood by reference to the following examples, which are included merely for purposes of illustration and are not intended to limit the disclosure herein.

Enzymatic Transamination of Compound (I-a)

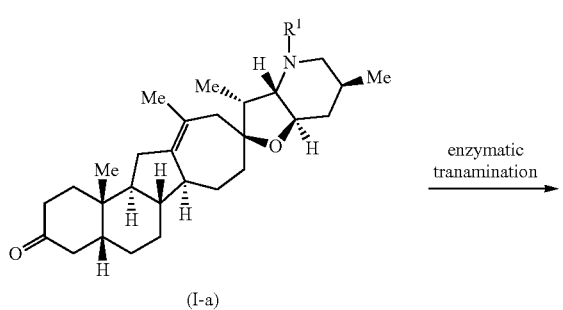

(I-a)

enzymatic tranamination →

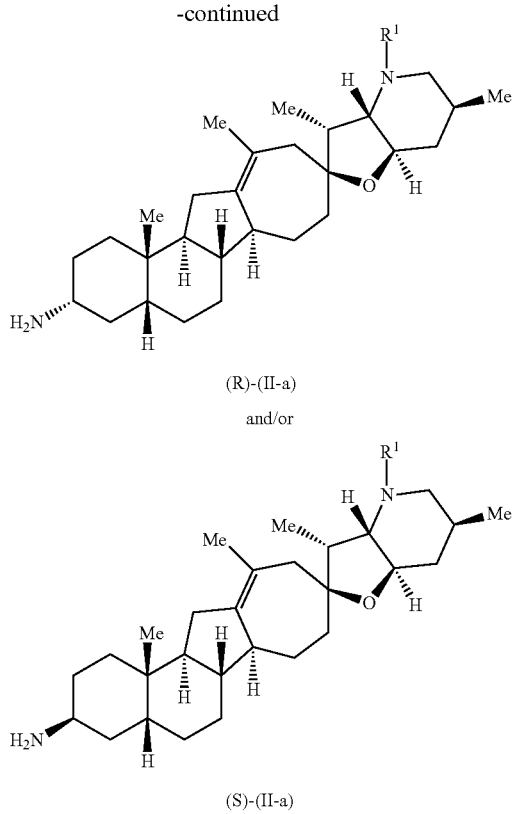

(R)-(II-a)

and/or (S)-(II-a)

Materials and Methods

Enzymes.

A mine transaminase enzymes were purchased from commercially available sources, stored at −20° C., and used as received: ATA-113 (Codexis, Redwood City, Calif.; Lot no. 104020902); ATA-117 (Codexis, Redwood City, Calif.; Lot no. 104020902); omega-transaminase from *Vibrio fluvialis* (Fluka; cat. no 08374); glutamate pyruvate transaminase (Fluka); broad range transaminase (Fluka).

Co-Enzymes.

Co-enzymes utilized during the investigation include: L-alanine dehydrogenase (LADH, Sigma, no. A7653-100 U), formate dehydrogenase (FDH, Codexis, FDH-101) and pyruvate reductase mix (PRM-102, Codexis), which is a mixture lactate dehydrogenase (LDH), glucose dehydrogenase (GDH), glucose and $NAD^+$.

pH.

The following buffers were used during the investigation: 100 mM sodium phosphate buffer (pH 7; Fluka no. 82637); 20 mM sodium phosphate buffer (pH 7.5; Fluka, no. 82592); 20 mM sodium phosphate buffer (pH 8; Fluka, no. 82593).

HPLC Method 1.

Symmetry C18 column 4.6×150 mm; flow rate 1.5 mL/min; mobile phase A=0.1% TFA in water; mobile phase B=0.1% TFA in acetonitrile; 10 μL injection; 40° C. column temperature; detection wavelength=215 nm (all species). Retention time of compound (II-a) ($R^1$=H: S-(II-a)=5.9 min; R-(II-a), =6.8 min).

HPLC Method 1 Gradient:

| Time (minutes) | % mobile phase A | % mobile phase B |
|---|---|---|
| 0 | 90 | 10 |
| 1.0 | 90 | 10 |
| 10.0 | 40 | 60 |
| 11.0 | 5 | 95 |
| 12.0 | 5 | 95 |
| 13.0 | 90 | 10 |
| 15.0 | 90 | 10 |

HPLC Method 2.

XBridge C8 column 4.6×75 mm; flow rate 1.0 mL/min; mobile phase A=10 mM ammonium formate buffer, pH 3.8; mobile phase B=0.05% formic acid in acetonitrile; 5 μL injection; 40° C. column temperature; detection wavelength=215 nm (all species). Retention time of compound (II-a) ($R^1$=Bn: S-(II-a)=7.0 min; R-(II-a)=7.5 min).

HPLC Method 2 Gradient:

| Time (minutes) | % mobile phase A | % mobile phase B |
|---|---|---|
| 0 | 80 | 20 |
| 2 | 80 | 20 |
| 16 | 5 | 95 |
| 18 | 5 | 95 |
| 18.1 | 80 | 20 |
| 20 | 80 | 20 |

HPLC Method 3.

Eclipse XDB-C8 column 4.6×50 mm; flow rate 1.5 mL/min; mobile phase A=0.1% TFA in water; mobile phase B=0.1% TFA in acetonitrile; 10 μL injection; 40° C. column temperature; detection wavelength=215 nm (all species). Retention time of compound (II-a) ($R^1$=Cbz: S-(II-a)=6.0 min; R-(II-a)=6.1 min).

HPLC Method 3 Gradient:

| Time (minutes) | % mobile phase A | % mobile phase B |
|---|---|---|
| 0 | 70 | 30 |
| 2.0 | 70 | 30 |
| 8.0 | 0 | 100 |
| 10.0 | 0 | 100 |
| 12.0 | 70 | 30 |
| 15.0 | 70 | 30 |

General Experimental Methods

Method A:

Compound (I-a), a sodium phosphate buffered solution, 1 mM pyridoxal phosphate (PLP), an amine transaminase enzyme, an amino donor molecule, PRM-102 and, optionally, a co-solvent, were added to a vial. The vial was capped and the reaction stirred at 30° C. for 72 hours. The reaction mixture was then lyophilized and the residue was re-dissolved in methanol (2 mL). A 100 μL portion of the methanol solution was filtered and analyzed by HPLC. The results of Experiments 1-8 using Method A are summarized in Table 6.

Method B:

Compound (I-a), a sodium phosphate buffered solution, 1 mM pyridoxal phosphate (PLP), amine transaminase enzyme, D-alanine, ammonium formate ($NH_4CO_2H$), L-alanine dehydrogenase (LADH) solution (8.05 U/mL), formate dehydrogenase (FDH) solution (10 U/mL), NAD (1 mM) and a co-solvent were added to a vial. The vial was capped and the reaction stirred at 30° C. for 72 hours. The reaction mixture was then lyophilized and the residue was re-dissolved in methanol (2 mL). A 100 μL portion of the methanol solution was filtered and analyzed by HPLC. The results of Experiments 1-10 using Method B are summarized in Table 7.

Method C:

Compound (I-a), a sodium phosphate buffered solution, pyridoxal phosphate (PLP) (0.5 mM to 1 mM), an amine transaminase enzyme, an amino donor molecule, and, optionally, a co-solvent and PRM-102, were added to a vial. The vial was capped and the reaction stirred at 37° C. for 24 hours to about 6 days (144 hours). The reaction mixture was then lyophilized and the residue was re-dissolved in methanol (2 mL). A 100 μL portion of the methanol solution was filtered and analyzed by HPLC. The results of Experiments 1-28 using Method C are summarized in Table 8.

Method D:

Compound (I-a), a sodium phosphate buffered solution, pyridoxal phosphate (PLP) (0.5 mM), an amine transaminase enzyme, an amino donor molecule (5 equivalents), PRM-102, and, optionally, a co-solvent, were added to a vial. The vial was capped and the reaction stirred at 37° C. for 24 hours to about 7 days (168 hours). A 100 μL portion of the reaction mixture was diluted with 1 volume of MeOH and analyzed by HPLC. The results of Experiments 1-13 using Method D are summarized in Table 9.

Method E:

Compound (I-a), a sodium phosphate buffered solution, pyridoxal phosphate (PLP) (0.5 mM), an amine transaminase enzyme, L-alanine (5 equivalents), PRM-102, and methanol (10% v/v) were added to a vial. The vial was capped and the reaction stirred at 37° C. for 24 hours to about 7 days (168 hours). A 100 μL portion of the reaction mixture was diluted with 1 volume of MeOH and analyzed by HPLC. The results of Experiments 1-5 using Method E are summarized in Table 10.

Method F:

Compound (I-a), a sodium phosphate buffered solution (pH=7.5), pyridoxal phosphate (PLP) (0.5 mM), an amine transaminase enzyme, L-alanine (5 equivalents), PRM-102, and methanol (10% v/v) were added to a vial. The vial was capped and the reaction stirred at 37° C. for 24 hours to about 7 days (168 hours). The pH of the aqueous layer was monitored at the onset and during the course of the reaction and if necessary, it was readjusted to 7.5 using 0.1 M NaOH solution. A 100 μL portion of the reaction mixture was diluted with 1 volume of MeOH and analyzed by HPLC. The results of Experiments 1-9 using Method F are summarized in Table 11.

Method G:

Compound (I-a), a sodium phosphate buffered solution (pH=7.5), pyridoxal phosphate (PLP) (0.5 mM), an amine transaminase enzyme, L-alanine (5 equivalents), PRM-102, an additive (100% wt/wt) and methanol (10% v/v) were added to a vial. The vial was capped and the reaction stirred at 37° C. for 24 hours to about 7 days (168 hours). A 100 μL portion of the reaction mixture was diluted with 1 volume of MeOH and analyzed by HPLC. The results of Experiments 1-5 using Method G are summarized in Table 12.

Method H:

Compound (I-a), a sodium phosphate buffered solution (pH=7.5), pyridoxal phosphate (PLP) (0.5 mM), an amine transaminase enzyme, L-alanine (5 equivalents), PRM-102, a co-solvent (10 to 20% v/v) were added to a vial. The vial was capped and the reaction stirred at 37° C. for 24 hours to about 7 days (168 hours). A 100 μL portion of the reaction mixture was diluted with 1 volume of MeOH and analyzed by HPLC. The results of Experiments 1-12 using Method H are summarized in Table 13.

TABLE 6

Method A

| | (I-a) | Buffer | pH | Co-solvent | PLP (mM) | Enzyme | Amine donor | PRM-102 (mg) | Time (hrs) | 2 | % Conversion |
|---|---|---|---|---|---|---|---|---|---|---|---|
| 1 | 6.5 mg ($R^1$ = H, citrate salt) | 100 mM (0.85 mL) | 7 | MeOH (0.15 mL) | 1 | ATA-117 (3 mg) | D-alanine (4.5 mg) | 39 | 72 | (S) | 3% |
| 2 | 6.5 mg ($R^1$ = H, citrate salt) | 100 mM (0.85 mL) | 7 | $CF_3CH_2OH$ (0.15 mL) | 1 | ATA-117 (3 mg) | D-alanine (4.5 mg) | 39 | 72 | — | n/a |
| 3 | 20 mg ($R^1$ = H, citrate salt) | 100 mM (2 mL) | 7 | none | 1 | ATA-117 (3 mg) | D-alanine (9.5 mg) | 60 | 72 | (S) | 3% |
| 4 | 20 mg ($R^1$ = H, citrate salt) | 100 mM (1.8 mL) | 7 | MeOH (0.2 mL) | 1 | ATA-117 (10 mg) | D-alanine (11 mg) | 60 | 72 | (S) | 2% |
| 5 | 20 mg ($R^1$ = H, citrate salt) | 100 mM (1.8 mL) | 7 | MeOH (0.2 mL) | 1 | broad-range transaminase (1.7 mg) | D-alanine (11 mg) | 60 | 72 | — | n/a |
| 6 | 20 mg ($R^1$ = H, citrate salt) | 100 mM (1.8 mL) | 7 | MeOH (0.2 mL) | 1 | glutamate pyruvate transaminase (1 mg) | D-alanine (11 mg) | 60 | 72 | — | n/a |
| 7 | 20 mg ($R^1$ = H, citrate salt) | 100 mM (2 mL) | 7 | none | 1 | ATA-113 (10 mg) | L-alanine (9.5 mg) | 60 | 72 | (S) | 15% |
| 8 | 20 mg ($R^1$ = H, citrate salt) | 100 mM (1.8 mL) | 7 | MeOH (0.2 mL) | 1 | ATA-113 (10 mg) | L-alanine (11 mg) | 60 | 72 | (S) | 5% |

TABLE 7

| | Method B | | | | | | | | | | | | |
|---|---|---|---|---|---|---|---|---|---|---|---|---|---|
| | (I-a) | Buffer | pH | co-solvent | PLP (mM) | enzyme | donor | NH₄CO₂H (mg) | FDH (μL) | LADH (μL) | NAD (mM) | 2 | % |
| 1 | 3.5 mg (R¹ = H, citrate salt) | 100 mM (0.85 mL) | 7 | DMSO (0.15 mL) | 1 | ATA-117 (3 mg) | D-alanine (9.5 mg) | 4 | 25 | 10 | 1 | — | n/a |
| 2 | 3.5 mg (R¹ = H, citrate salt) | 100 mM (0.85 mL) | 7 | MeOH (0.15 mL) | 1 | ATA-117 (3 mg) | D-alanine (9.5 mg) | 4 | 25 | 10 | 1 | (S) | 1% |
| 3 | 3.5 mg (R¹ = H, citrate salt) | 20 mM (0.85 mL) | 7.5 | DMSO (0.15 mL) | 1 | ATA-117 (3 mg) | D-alanine (9.5 mg) | 4 | 25 | 10 | 1 | — | n/a |
| 4 | 3.5 mg (R¹ = H, citrate salt) | 20 mM (0.85 mL) | 7.5 | MeOH (0.15 mL) | 1 | ATA-117 (3 mg) | D-alanine (9.5 mg) | 4 | 25 | 10 | 1 | — | n/a |
| 5 | 6.5 mg (R¹ = H, citrate salt) | 100 mM (0.85 mL) | 7 | CF₃CH₂OH (0.15 mL) | 1 | ATA-117 (3 mg) | D-alanine (13 mg) | 6 | 50 | 20 | 1 | — | n/a |
| 6 | 6.5 mg (R¹ = H, citrate salt) | 100 mM (0.85 mL) | 7 | MeOH (0.15 mL) | 1 | ATA-117 (3 mg) | D-alanine (22 mg) | 9 | 50 | 20 | 1 | (S) | 5% |
| 7 | 3.5 mg (R¹ = H, citrate salt) | 100 mM (0.85 mL) | 7 | MeOH (0.15 mL) | 1 | ATA-113 (1.3 mg) | D-alanine (9.5 mg) | 4 | 22 | 8.8 | 1 | (S) | 8% |
| 8 | 3.5 mg (R¹ = H, citrate salt) | 100 mM (0.85 mL) | 7 | DMSO (0.15 mL) | 1 | ATA-113 (1.3 mg) | D-alanine (9.5 mg) | 4 | 22 | 8.8 | 1 | (S) | 37% |
| 9 | 10 mg (R¹ = H, citrate salt) | 100 mM (8.5 mL) | 7 | DMSO (1.5 mL) | 1 | ATA-113 (13 mg) | D-alanine (95 mg) | 40 | 216 | 86 | 1 | (S) | 12% |
| 10 | 3.5 mg (R¹ = H, citrate salt) | 100 mM (0.85 mL) | 7 | DMSO (1.3 mL); Et₂O (0.2 mL) | 1 | ATA-113 (1.3 mg) | D-alanine (12 mg) | 5 | 22 | 8.8 | 1 | (S) | 10% |

TABLE 8

| | Method C | | | | | | | | | | |
|---|---|---|---|---|---|---|---|---|---|---|---|
| | (I-a) | Buffer | pH | Co-solvent | PLP (mM) | Enzyme | Amine donor | PRM-102 (mg) | Time (hrs) | 2 | % Conversion |
| 1 | 15 mg (R¹ = H) | 100 mM (1.8 mL) | 7 | MeOH (0.2 mL) | 1 | ATA-117 (10 mg) | D-alanine (13 mg) | 60 | 24 | (S) | 2% |
| 2 | 15 mg (R¹ = H) | 100 mM (1.8 mL) | 7 | MeOH (0.2 mL) | 1 | ATA-113 (10 mg) | L-alanine (13 mg) | 60 | 24 | (S) | 10% |
| 3 | 1 mg (R¹ = H) | 20 mM (1.2 mL) | 7.5 | MeOH (0.12 mL) | 0.5 | ATA-113 (2 mg) | (S)-methyl benzyl amine (1.4 μL) | none | 72 | (S) | 9% |
| 4 | 1 mg (R¹ = H) | 20 mM (1.2 mL) | 7.5 | MeOH (0.12 mL) | 0.5 | ATA-113 (2 mg) | (S)-methyl benzyl amine (1.4 μL) | 30 | 72 | (S) | 41% |
| 5 | 8.5 mg (R¹ = H) | 20 mM (10 mL) | 7.5 | MeOH (1 mL) | 1 | ATA-113 (20 mg) | (S)-methyl benzyl amine (13 μL) | 300 | 72 | (S) | 42% |
| 6 | 1 mg (R¹ = H) | 20 mM (1.2 mL) | 7.5 | MeOH (0.12 mL) | 0.5 | ATA-117 (2 mg) | (S)-methyl benzyl amine (1.4 μL) | none | 72 | — | n/a |
| 7 | 1 mg (R¹ = H) | 20 mM (1.2 mL) | 7.5 | MeOH (0.12 mL) | 0.5 | ATA-117 (2 mg) | (S)-methyl benzyl amine (1.4 μL) | 30 | 72 | — | n/a |
| 8 | 1 mg (R¹ = H) | 20 mM (1.2 mL) | 7.5 | MeOH (0.12 mL) | 0.5 | ATA-117 (4 mg) | (S)-methyl benzyl amine (1.4 μL) | 60 | 72 | — | n/a |
| 9 | 8.5 mg (R¹ = H) | 20 mM (10 mL) | 7.5 | MeOH (1 mL) | 0.5 | ATA-117 (10 mg) | (S)-methyl benzyl amine (13 μL) | 150 | 72 | — | n/a |
| 10 | 8.5 mg (R¹ = H) | 20 mM (9 mL) | 8 | MeOH (1 mL) | 0.5 | ATA-117 (20 mg) | (S)-methyl benzyl amine (13 μL) | 300 | 72 | — | n/a |
| 11 | 6.4 mg (R¹ = H) | 20 mM (9 mL) | 8 | MeOH (1 mL) | 0.5 | ATA-117 (20 mg) | (S)-methyl benzyl amine (13 μL) | 300 | 72 | — | n/a |

TABLE 8-continued

Method C

| | (I-a) | Buffer | pH | Co-solvent | PLP (mM) | Enzyme | Amine donor | PRM-102 (mg) | Time (hrs) | 2 | % Conversion |
|---|---|---|---|---|---|---|---|---|---|---|---|
| 12 | 4.3 mg (R¹ = H) | 20 mM (9 mL) | 8 | MeOH (1 mL) | 0.5 | ATA-117 (20 mg) | (S)-methyl benzyl amine (13 μL) | 300 | 72 | — | n/a |
| 13 | 2.1 mg (R¹ = H) | 20 mM (9 mL) | 8 | MeOH (1 mL) | 0.5 | ATA-117 (20 mg) | (S)-methyl benzyl amine (13 μL) | 300 | 72 | — | n/a |
| 14 | 1.6 mg (R¹ = H) | 20 mM (1.2 mL) | 7.5 | none | 1 | Vibrio fluvialis (55 μL) | (S)-methyl benzyl amine (13 μL) | none | 72 | (R) | 2% |
| 15 | 1 mg (R¹ = H) | 20 mM (1.2 mL) | 7.5 | MeOH (0.12 mL) | 0.5 | Vibrio Fluvialis (100 μL) | (R)-methyl benzyl amine (1.4 μL) | none | 72 | (R) | 10% |
| 16 | 4.3 mg (R¹ = H) | 20 mM (4.95 mL) | 7.5 | MeOH (0.55 mL) | 0.5 | Vibrio Fluvialis (155 μL) | (R)-methyl benzyl amine (6.5 μL) | 140 | 72 | (R) | 15% |
| 17 | 1.6 mg (R¹ = H) | 20 mM (2 mL) | 7.5 | none | 0.5 | Vibrio Fluvialis (100 μL) | (S)-methyl benzyl amine (1.4 μL) | none | 72 | (R) | 3% |
| 18 | 8.5 mg (R¹ = H) | 20 mM (10 mL) | 7.5 | MeOH (1 mL) | 0.5 | Vibrio Fluvialis (100 μL) | (R)-methyl benzyl amine (13 μL) | none | 72 | (R) | 10% |
| 19 | 8.5 mg (R¹ = H) | 20 mM (10 mL) | 7.5 | MeOH (1 mL) | 0.5 | Vibrio Fluvialis (310 μL) | (S)-methyl benzyl amine (13 μL) | none | 72 | (R) | 10% |
| 20 | 8.5 mg (R¹ = H) | 20 mM (10 mL) | 7.5 | MeOH (1 mL) | 0.5 | Vibrio Fluvialis (310 μL) | (S)-methyl benzyl amine (13 μL) | 275 | 72 | (R) | 10% |
| 21 | 14 mg (R¹ = H, citrate salt) | 20 mM (10 mL) | 7.5 | MeOH (1 mL) | 0.5 | Vibrio Fluvialis (310 μL) | (R)-methyl benzyl amine (13 μL) | 300 | 72 | (R) | 17% |
| 22 | 7 mg (R¹ = H, citrate salt) | 20 mM (5 mL) | 7.5 | MeOH (0.5 mL) | 0.5 | Vibrio Fluvialis (155 μL) | (R)-methyl benzyl amine (7 μL) | 150 | 144 | (R) | 28% |
| 23 | 5.5 mg (R¹ = Bn) | 20 mM (5 mL) | 7.5 | EtOAc (0.5 mL) | 1 | Vibrio Fluvialis (150 μL) | (R)-methyl benzyl amine (7 μL) | 150 | 72 | — | n/a |
| 24 | 3.5 mg (R¹ = Bn) | 20 mM (5 mL) | 7.5 | cyclohexanone (0.5 mL) | 1 | Vibrio Fluvialis (150 μL) | (R)-methyl benzyl amine (7 μL) | 150 | 72 | — | n/a |
| 25 | 8.5 mg (R¹ = Bn) | 20 mM (10 mL) | 7 | MeOH (1 mL) | 0.5 | ATA-113 (20 mg) | (S)-methyl benzyl amine (13 μL) | 300 | 72 | (S) | 1.7% |
| 26 | 8.5 mg (R¹ = CBz) | 20 mM (10 mL) | 7 | MeOH (1 mL) | 0.5 | ATA-113 (20 mg) | (S)-methyl benzyl amine (13 μL) | 300 | 72 | (S) | 2% |
| 27 | 8.5 mg (R¹ = Bn) | 20 mM (10 mL) | 7 | MeOH (1 mL) | 0.5 | ATA-117 (20 mg) | (S)-methyl benzyl amine (13 μL) | 300 | 72 | — | n/a |
| 28 | 8.5 mg (R¹ = Cbz) | 20 mM (10 mL) | 7 | MeOH (1 mL) | 0.5 | ATA-117 (20 mg) | (S)-methyl benzyl amine (13 μL) | 300 | 72 | — | n/a |

TABLE 9

Method D

| | (I-a) | Buffer | pH | Co-solvent | PLP (mM) | Enzyme | Amine Donor (5 equiv.) | PRM-102 (mg) | Time (hrs) | 2 | % Conversion |
|---|---|---|---|---|---|---|---|---|---|---|---|
| 1 | 14 mg (R¹ = H, citrate salt) | 20 mM (9 mL) | 7.0 | MeOH (1.0 mL) | 0.5 | Vibrio Fluvialis (310 μL) | L-alanine | 300 mg | 168 | (R) | 16.1% |
| 2 | 14 mg (R¹ = H, citrate salt) | 20 mM (9 mL) | 7.0 | MeOH (1.0 mL) | 0.5 | Vibrio Fluvialis (310 μL) | D-alanine | 300 mg | 168 | (R) | 12.7% |
| 3 | 14 mg (R¹ = H, citrate salt) | 20 mM (9 mL) | 7.0 | MeOH (1.0 mL) | 0.5 | Vibrio Fluvialis (310 μL) | R-Methylbenzylamine | 300 mg | 168 | (R) | 14.1% |
| 4 | 14 mg (R¹ = H, citrate salt) | 20 mM (9 mL) | 7.0 | MeOH (1.0 mL) | 0.5 | Vibrio Fluvialis (310 μL) | S-Methyl benzylamine | 300 mg | 168 | (R) | 7.6% |

TABLE 9-continued

Method D

| | (I-a) | Buffer | pH | Co-solvent | PLP (mM) | Enzyme | Amine Donor (5 equiv.) | PRM-102 (mg) | Time (hrs) | 2 | % Conversion |
|---|---|---|---|---|---|---|---|---|---|---|---|
| 5 | 14 mg (R$^1$ = H, citrate salt) | 20 mM (9 mL) | 7.0 | MeOH (1.0 mL) | 0.5 | *Vibrio Fluvialis* (310 μL) | 2-aminoindane | 300 mg | 168 | (R) | 4.1% |
| 6 | 14 mg (R$^1$ = H, citrate salt) | 20 mM (9 mL) | 7.0 | MeOH (1.0 mL) | 0.5 | *Vibrio Fluvialis* (310 μL) | S-1-Aminoindane | 300 mg | 168 | — | n/a |
| 7 | 14 mg (R$^1$ = H, citrate salt) | 20 mM (9 mL) | 7.0 | MeOH (1.0 mL) | 0.5 | *Vibrio Fluvialis* (310 μL) | R-1-Aminoindane | 300 mg | 168 | (R) | 5.1% |
| 8 | 14 mg (R$^1$ = H, citrate salt) | 20 mM (9 mL) | 7.0 | MeOH (1.0 mL) | 0.5 | *Vibrio Fluvialis* (310 μL) | R-2-Amino-1-propanol | 300 mg | 168 | (R) | 3.8% |
| 9 | 14 mg (R$^1$ = H, citrate salt) | 20 mM (9 mL) | 7.0 | MeOH (1.0 mL) | 0.5 | *Vibrio Fluvialis* (310 μL) | S-2-Amino-1-propanol | 300 mg | 168 | (R) | 4.6% |
| 10 | 14 mg (R$^1$ = H, citrate salt) | 20 mM (9 mL) | 7.0 | MeOH (1.0 mL) | 0.5 | *Vibrio Fluvialis* (310 μL) | (1R, 2S)-cis-1-Amino-2-indanol | 300 mg | 168 | — | n/a |
| 11 | 14 mg (R$^1$ = H, citrate salt) | 20 mM (9 mL) | 7.0 | MeOH (1.0 mL) | 0.5 | *Vibrio Fluvialis* (310 μL) | (1R, 2R)-trans-1-Amino-2-indanol | 300 mg | 168 | — | n/a |
| 12 | 14 mg (R$^1$ = H, citrate salt) | 20 mM (9 mL) | 7.0 | MeOH (1.0 mL) | 0.5 | *Vibrio Fluvialis* (310 μL) | 1-R-Amino-6-hydroxyindanamine | 300 mg | 168 | — | n/a |
| 13 | 14 mg (R$^1$ = H, citrate salt) | 20 mM (9 mL) | 7.0 | MeOH (1.0 mL) | 0.5 | *Vibrio Fluvialis* (310 μL) | Isopropylamine | 300 mg | 168 | (R) | 8.4% |

TABLE 10

Method E

| | (I-a) | Buffer | pH | Co-solvent | PLP (mM) | Enzyme | Amine donor | PRM-102 (mg) | Time (hrs) | 2 | % Conversion |
|---|---|---|---|---|---|---|---|---|---|---|---|
| 1 | 14 mg (R$^1$ = H, citrate salt) | 20 mM (9 mL) | 7.0 | MeOH (1.0 mL) | 0.5 | *Vibrio Fluvialis* (155 μL) | L-alanine (10 mg) | 300 mg | 168 | (R) | 6.4% |
| 2 | 14 mg (R$^1$ = H, citrate salt) | 20 mM (9 mL) | 8.0 | MeOH (1.0 mL) | 0.5 | *Vibrio Fluvialis* (155 μL) | L-alanine (10 mg) | 300 mg | 168 | (R) | 14.9% |
| 3 | 14 mg (R$^1$ = H, citrate salt) | 20 mM (9 mL) | 9.0 | MeOH (1.0 mL) | 0.5 | *Vibrio Fluvialis* (155 μL) | L-alanine (10 mg) | 300 mg | 168 | (R) | 10.2% |
| 4 | 14 mg (R$^1$ = H, citrate salt) | 100 mM (9 mL) | 8.1 | MeOH (1.0 mL) | 0.5 | *Vibrio Fluvialis* (155 μL) | L-alanine (10 mg) | 300 mg | 168 | (R) | 3.6% |
| 5 | 14 mg (R$^1$ = H, citrate salt) | 100 mM (9 mL) | 7.1 | MeOH (1.0 mL) | 0.5 | *Vibrio Fluvialis* (155 μL) | L-alanine (10 mg) | 300 mg | 168 | (R) | 7.9% |

TABLE 11

Method F

| | (I-a) | Buffer | pH | Co-solvent | PLP (mM) | Enzyme | Amine donor | PRM-102 (mg) | Time (hrs) | 2 | % Conversion |
|---|---|---|---|---|---|---|---|---|---|---|---|
| 1 | 14 mg (R$^1$ = H, citrate salt) | 20 mM (9 mL) | 7.5 | MeOH (1.0 mL) | 0.5 | *Vibrio Fluvialis* (155 μL) | D-alanine (10 mg) | 300 mg | 168 | (R) | 12.7% |
| 2 | 14 mg (R$^1$ = H, citrate salt) | 20 mM (9 mL) | 7.5 | MeOH (1.0 mL) | none | *Vibrio Fluvialis* (155 μL) | D-alanine (10 mg) | 300 mg | 168 | — | n/a |

TABLE 11-continued

| | Method F | | | | | | | | | | |
|---|---|---|---|---|---|---|---|---|---|---|---|
| | (I-a) | Buffer | pH | Co-solvent | PLP (mM) | Enzyme | Amine donor | PRM-102 (mg) | Time (hrs) | 2 | % Conversion |
| 3 | 14 mg (R$^1$ = H, citrate salt) | 20 mM (9 mL) | 7.5 | MeOH (1.0 mL) | 0.5 | Vibrio Fluvialis (155 µL) | L-alanine (10 mg) | 300 mg | 168 | (R) | 16.1% |
| 4 | 14 mg (R$^1$ = H, citrate salt) | 20 mM (9 mL) | 7.5 | MeOH (1.0 mL) | none | Vibrio Fluvialis (155 µL) | L-alanine (10 mg) | 300 mg | 168 | — | n/a |
| 5 | 14 mg (R$^1$ = H, citrate salt) | 20 mM (9 mL) | 7.5 | MeOH (1.0 mL) | 0.5 | Vibrio Fluvialis (310 µL) | L-alanine (10 mg) | 300 mg | 168 | (R) | 31% |
| 6 | 14 mg (R$^1$ = H, citrate salt) | 20 mM (9 mL) | 7.5 | MeOH (1.0 mL) | 0.5 | Vibrio Fluvialis (310 µL on day 1, 155 µL on day 4) | L-alanine (10 mg) | 300 mg | 168 | (R) | 41.1% |
| 7 | 14 mg (R$^1$ = H, citrate salt) | 20 mM (9 mL) | 7.5 | MeOH (1.0 mL) | 0.5 | Vibrio Fluvialis, NEW BATCH (310 µL on day 1, 155 µL on day 6) | L-alanine (10 mg) | 300 mg | 168 | (R) | 48.7% |
| 8 | 45 mg (R$^1$ = H, citrate salt) | 20 mM (9 mL) | 7.5 | MeOH (1.0 mL) | 0.5 | Vibrio Fluvialis NEW BATCH (310 µL) | L-alanine (10 mg) | 300 mg | 168 | (R) | 8.6% |
| 9 | 14 mg (R$^1$ = H, citrate salt) | 20 mM (9 mL) | 7.5 | MeOH (1.0 mL) | 0.5 | Vibrio Fluvialis, NEW BATCH (310 µL) | L-alanine (20 mg) | 300 mg | 168 | (R) | 14.5% |

TABLE 12

| | Method G | | | | | | | | | | |
|---|---|---|---|---|---|---|---|---|---|---|---|
| | (I-a) | Buffer | Additives | Co-solvent | PLP (mM) | Enzyme | Amine donor | PRM-102 (mg) | Time (hrs) | 2 | % Conversion |
| 1 | 14 mg (R$^1$ = H, citrate salt) | 20 mM (9 mL) | Amberlite Resin (100 wt %) | MeOH (1.0 mL) | 0.5 | Vibrio Fluvialis (310 µL) | L-alanine (10 mg) | 300 mg | 96 | (R) | 3.7% |
| 2 | 14 mg (R$^1$ = H, citrate salt) | 20 mM (9 mL) | Dowex Resin (100 wt %) | MeOH (1.0 mL) | 0.5 | Vibrio Fluvialis (310 µL) | L-alanine (10 mg) | 300 mg | 96 | — | n/a |
| 3 | 14 mg (R$^1$ = H, citrate salt) | 20 mM (9 mL) | β-Cyclodextrin (100 wt %) | MeOH (1.0 mL) | 0.5 | Vibrio Fluvialis (310 µL) | L-alanine (10 mg) | 300 mg | 96 | (R) | 14.0 |
| 4 | 14 mg (R$^1$ = H, citrate salt) | 20 mM (9 mL) | γ-Cyclodextrin (100 wt %) | MeOH (1.0 mL) | 0.5 | Vibrio Fluvialis (310 µL) | L-alanine (10 mg) | 300 mg | 96 | (R) | 11.4 |
| 5 | 14 mg (R$^1$ = H, citrate salt) | 20 mM (9 mL) | Sodium Bisulfite (100 wt %) | MeOH (1.0 mL) | 0.5 | Vibrio Fluvialis (310 µL) | benzylamine (10 mg) | 300 mg | 96 | — | n/a |

TABLE 13

| | Method H | | | | | | | | | | |
|---|---|---|---|---|---|---|---|---|---|---|---|
| | (I-a) | Buffer | pH | Co-solvent | PLP (mM) | Enzyme | Amine donor | PRM-102 (mg) | Time (hrs) | 2 | % Conversion |
| 1 | 14 mg (R$^1$ = H, citrate salt) | 20 mM (9 mL) | 7.5 | none | 0.5 | Vibrio Fluvialis (155 µL) | L-alanine (10 mg) | 300 mg | 168 | (R) | 6.4% |

TABLE 13-continued

Method H

| (I-a) | Buffer | pH | Co-solvent | PLP (mM) Enzyme | | Amine donor | PRM-102 (mg) | Time (hrs) | 2 | % Conversion |
|---|---|---|---|---|---|---|---|---|---|---|
| 2 14 mg (R¹ = H) | 20 mM (9 mL) | 7.5 | MeOH (1.0 mL) | 0.5 | Vibrio Fluvialis (155 µL) | L-alanine (10 mg) | 300 mg | 168 | (R) | 14.9% |
| 3 14 mg (R¹ = H) | 20 mM (9 mL) | 7.5 | DMSO (1.0 mL) | 0.5 | Vibrio Fluvialis (155 µL) | L-alanine (10 mg) | 300 mg | 168 | (R) | 8.2% |
| 4 14 mg (R¹ = H) | 100 mM (9 mL) | 7.5 | Heptane (2.0 mL) | 0.5 | Vibrio Fluvialis (155 µL) | L-alanine (10 mg) | 300 mg | 168 | — | n/a |
| 5 14 mg (R¹ = H) | 100 mM (9 mL) | 7.5 | Heptane (2.0 mL) | 0.5 | Vibrio Fluvialis (155 µL) | R-Methyl benzylamine | 300 mg | 168 | — | n/a |
| 6 14 mg (R¹ = H) | 100 mM (9 mL) | 7.5 | Toluene (2.0 mL) | 0.5 | Vibrio Fluvialis (155 µL) | L-alanine (10 mg) | 300 mg | 168 | — | n/a |
| 7 14 mg (R¹ = H) | 100 mM (9 mL) | 7.5 | Toluene (2.0 mL) | 0.5 | Vibrio Fluvialis (155 µL) | R-Methyl benzylamine | 300 mg | 168 | — | n/a |
| 8 14 mg (R¹ = H) | 100 mM (9 mL) | 7.5 | 2-Methyl tetrahydrofuran (2.0 mL) | 0.5 | Vibrio Fluvialis (155 µL) | L-alanine (10 mg) | 300 mg | 168 | — | n/a |
| 9 14 mg (R¹ = H) | 100 mM (9 mL) | 7.5 | 2-Methyl tetrahydrofuran (2.0 mL) | 0.5 | Vibrio Fluvialis (155 µL) | R-Methyl benzylamine | 300 mg | 168 | — | n/a |
| 10 14 mg (R¹ = H) | 100 mM (9 mL) | 7.5 | Ethylacetate (2.0 mL) | 0.5 | Vibrio Fluvialis (155 µL) | L-alanine (10 mg) | 300 mg | 168 | (R) | 12.9% (aq. layer) 1.1% (organic layer) |
| 11 14 mg (R¹ = H) | 100 mM (9 mL) | 7.5 | Hexanes (2.0 mL) | 0.5 | Vibrio Fluvialis (155 µL) | L-alanine (10 mg) | 300 mg | 168 | (R) | 4.2% (aq. layer) 1.6% (organic layer) |
| 12 14 mg (R¹ = H) | 100 mM (9 mL) | 7.5 | Perfluorohexane (2.0 mL) | 0.5 | Vibrio Fluvialis (155 µL) | L-alanine (10 mg) | 300 mg | 168 | — | n/a |

| | Table Legend |
|---|---|
| PLP | pyridoxal phosphate |
| PRM 102 | pyruvate reductase mix available from Codexis, Inc. |
| (R) | (R) isomer preferentially generated |
| (S) | (S) isomer preferentially generated |
| % | percent conversion of the preferred isomer as determined by HPLC |
| n/a | no product detected by HPLC |
| Me | methyl, —CH₃ |
| Bn | benzyl, —CH₂C₆H₅ |
| Cbz | carbobenzyloxy, —C(=O)OCH₂C₆H₅ |
| DMSO | dimethylsulfoxide |
| MeOH | methanol |
| EtOAc | ethyl acetate |

Example: Evaluation of Candidate Transaminases

Candidate transaminases were evaluated using the reaction conditions described in Method A above (see Table 6). These experiments were carried out using PRM-102 (powder form) as the co-enzyme system and D-alanine or L-alanine as the amino donor molecule. In all but two of the runs, a water miscible co-solvent (methanol or trifluoroethanol (CF₃CH₂OH)) was employed. As shown in Table 6, % conversions of 5% and 15% were observed when the transamination was conducted in the presence of omega amine transaminase enzyme ATA-113, and % conversions of 2% and 3% were observed when the transamination was conducted in the presence of omega amine transaminase enzyme ATA-117. Omega amine transaminase enzymes ATA-117, known generally to be an (R)-selective transaminase, produced the compound (S)-(II-a) rather than compound (R)-(II-a). ATA-113, known generally to be an (S)-selective transaminase, produced the compound (S)-(II-a). The descriptor "n/a" indicates that the transamination product (II-a) was not detected by HPLC in the reaction mixture.

Example: Evaluation of FDH/LADH/NAD Coenzyme Mixtures

Candidate mixtures of the co-enzymes FDH, LADH and NAD were evaluated using the reaction conditions described in Method B above (see Table 7). These experiments were carried out using ATA-117 and ATA-113 as the amine transferase enzyme; D-alanine as the amino donor molecule; and DMSO, methanol or trifluoroethanol as the co-solvent. As shown in Table 7, % conversions of from 1% to 37% were observed using this co-enzyme system. Further, transamination was achieved using either ATA-117 or ATA-113 as the transaminase enzyme. The descriptor "n/a" indicates that the transamination product (II-a) was not detected by HPLC in the reaction mixture.

Example: Comparison of Omega Transaminase from *Vibrio fluvialis* with ATA-117 and ATA-113

The activity of the omega transaminase from *Vibrio fluvialis* was compared with the activities of ATA-117 and ATA-113 using the reaction conditions described in Method C above (see Table 8). These experiments were carried out using PRM-102 as the co-enzyme system and one of the following amino donor molecule: D-alanine, L-alanine, (S)-methyl benzylamine and (R)-methyl benzylamine. When ATA-117 or ATA-113 was employed as the transaminase enzyme, compound (S)-(II-a) was produced. As indicated in Table 8, this product stereochemistry (S) was obtained with amino donor molecules D-alanine, L-alanine, and (S)-methyl benzylamine. In contrast, when the omega amine transaminase from *Vibrio fluvialis* was employed as the amine transaminase enzyme, compound (R)-(II-a) was produced. As indicated in Table 8, this product stereochemistry was obtained when either (R) or (S)-methyl benzylamine was used as the amino donor molecule. The descriptor "n/a" indicates that the transamination product (II-a) was not detected by HPLC in the reaction mixture.

Example: Evaluation of Candidate Amino Donor Molecules

Candidate amino donor molecules were evaluated using the reaction conditions described in Method D above (see Table 9). These experiments were carried out using the omega transaminase from *Vibrio fluvialis*; a 20 mM phosphate buffer (pH=7.0); and methanol as the co-solvent. L-alanine, D-alanine, (R)-methylbenzylamine, (S)-methylbenzylamine, 2-aminoindane, (R)-1-aminoindane, (R)-2-amino-1-propanol, (S)-2-amino-1-propanol, (1R,2S)-cis-1-amino-2-indanol, (1R,2R)-trans-1-amino-2-indanol, 1-(R)-amino-6-hydroxyindanamine and isopropylamine were tested. As indicated in Table 9, only compound (R)-(II-a) was observed. L-alanine as amino donor molecule provided a % conversion of 16.1% over a period of 7 days. The descriptor "n/a" indicates that the transamination product (II-a) was not detected by HPLC in the reaction mixture.

Example: Evaluation of Candidate Reaction pH and Buffer Strengths

Candidate reaction pH and buffer strengths were evaluated using the reaction conditions described in Method E above (see Table 10). These experiments were carried out using buffers with different pH's and molarities. As shown in Table 10, a 20 mM phosphate buffer (maintaining a pH=8.0) was found to provide a % conversion of 14.9%. Increasing the molarity of the buffer (100 mM) was found to cause precipitation of the starting material (I-a) and reduce conversion to the product (R)-(II-a). The descriptor "n/a" indicates that the transamination product (II-a) was not detected by HPLC in the reaction mixture.

Table 11 shows the results for transamination reactions conducted at pH=7.5. These reactions were monitored for any change in the pH, and any change in the pH of the reaction mixture was adjusted using 0.1 N sodium hydroxide solution (Method F). However, it was also found that the conversion was dependent on the age of the enzyme. A fresh bottle of enzyme was found to increase % conversion up to 31% using L-alanine over a period of 7 days and 2 units/mg of the substrate compound (I-a). When the reaction mixture was charged with an additional unit of fresh enzyme at the end of day 6, the conversion improved to 48.7%. The descriptor "n/a" indicates that the transamination product (II-a) was not detected by HPLC in the reaction mixture.

Example: Evaluation of Candidate Additives

Candidate additives were evaluated using the reaction conditions described in Method G above (see Table 12). These experiments were carried out using additives, such as resins, cyclodextrins and sulfites. Resins capable of adsorbing the starting material compound (I-a) as well as the product compound (II-a) were screened. In addition, β- and γ-cyclodextrins that are known to solubilize organic compounds were also tested (% conversions of 14.0% and 11.4% were observed for β- and γ-cyclodextrin, respectively). The descriptor "n/a" indicates that the transamination product (II-a) was not detected by HPLC in the reaction mixture.

Example: Evaluation of Candidate Co-Colvents

Candidate co-colvents were evaluated using the reaction conditions described in Method H above (see Table 13). For monophasic systems, it was found that using methanol as the co-solvent provided the highest % conversion of those tested. For biphasic systems, it was found that using ethyl acetate as the co-solvent provided the highest % conversion of those tested. The descriptor "n/a" indicates that the transamination product (II-a) was not detected by HPLC in the reaction mixture.

Exemplary Sulfonylation of a Compound of Formula (II)

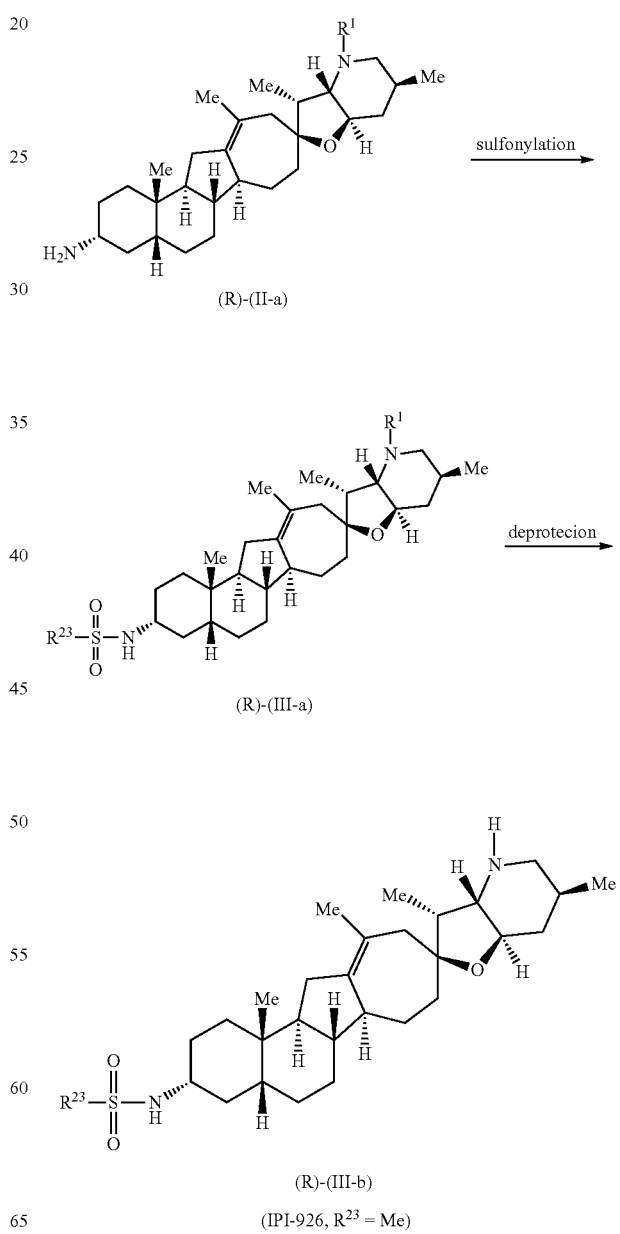

Procedure described in Tremblay et al., "Discovery of a Potent and Orally Active Hedgehog Pathway Antagonist (IPI-926)" *J. Med. Chem.* (2009) 52:4400-4418, incorporated herein by reference.

A solution of amine ($R^1$=CBz) (5.10 g, 9.09 mmol, 1 equiv) in dichloromethane (60 mL) was treated with diisopropylethylamine (5.88 g, 45.5 mmol, 5.0 equiv), cooled to 0° C., and treated with methanesulfonyl chloride (2.08 g, 18.2 mmol, 2.0 equiv). The reaction mixture was stirred for 30 min and partitioned between saturated aqueous sodium bicarbonate and ethyl acetate. The organic layer was separated, dried over sodium sulfate, and concentrated to dryness to provide a crude residue. The residue was purified using silica gel chromatography (10-30% EtOAc/hexanes) to provide the N-Cbz sulfonylated product. A suspension of the isolated product and 10% palladium on carbon (1.0 g) in 2-propanol (50 mL) was placed under hydrogen atmosphere and stirred for 4 h at room temperature. The reaction mixture was then filtered on Celite and the filtrate concentrated to dryness. The residue was then purified using silica gel chromatography (0-5% DCM/MeOH) to give IPI-926 (4.06 g, 8.05 mmol, 95% for two steps). NMR δH (400 MHz, CDCl3) 6.90 (br s, 1H), 3.31 (dt, J=10.6, 3.8 Hz, 1H), 3.20 (br s, 1H), 3.10 (dd, J=13.7, 4.5 Hz, 1H), 2.91 (s, 3H), 2.62 (dd, J=9.9, 7.6 Hz, 1H), 2.33 (br d, J=14.5 Hz, 1H), 2.27-2.15 (m, 1H), 2.10 (dd, J=14.5, 6.9 Hz, 1H), 1.99-1.17 (m, 28H), 1.05 (q, J=11.6 Hz, 1H), 0.93 (d, J=7.4 Hz, 3H), 0.88 (d, J=6.6 Hz, 3H), 0.86 (s, 3H); NMR δC (100 MHz, CDCl3) 140.47, 124.53, 82.48, 76.97, 63.73, 54.08, 53.87, 50.12, 49.98, 47.19, 44.73, 42.27, 42.10, 40.24, 37.55, 37.44, 36.04, 34.44, 31.87, 31.33, 30.46, 29.79, 28.37, 27.94, 26.26, 24.19, 22.70, 18.92, 10.19; m/z=505.29 [M+H]+; HPLC 99.1 a/a % at 215 nm.

EQUIVALENTS

Those skilled in the art will recognize, or be able to ascertain using no more than routine experimentation, many equivalents to the specific embodiments described herein. Such equivalents are intended to be encompassed by the following claims.

It is claimed:
1. A process for preparing a compound of formula (II):

(II)

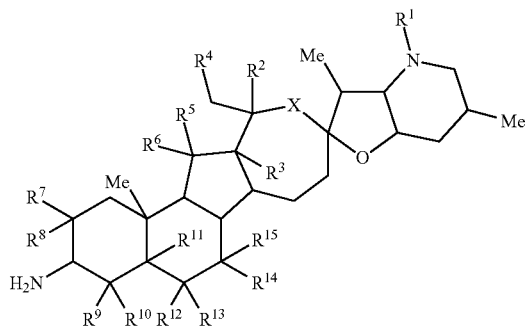

or a salt thereof;

from a compound of formula (I):

(I)

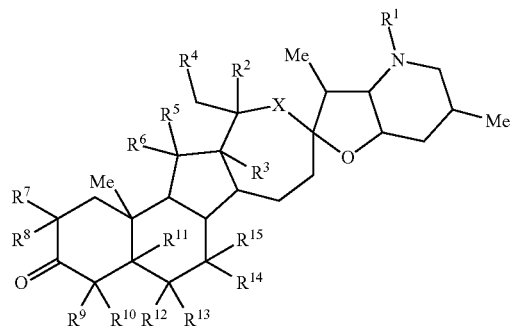

or a salt thereof;
wherein:
$R^1$ is H, alkyl, alkenyl, alkynyl, aryl, cycloalkyl, heterocycloalkyl, aralkyl, heteroaryl, heteroaralkyl, haloalkyl, —$OR^{16}$, —$C(O)R^{16}$, —$CO_2R^{16}$, —$SO_2R^{16}$, —$C(O)N(R^{17})(R^{17})$, —$[C(R^{16})_2]_q$—$R^{16}$, —$[(W)]$—$N(R^{17})C(O)]_qR^{16}$, —$[(W)$—$C(O)]_qR^{16}$, —$[(W)$—$C(O)O]_qR^{16}$, —$[(W)$—$OC(O)]_qR^{16}$, —$[(W)$—$SO_2]_qR^{16}$, —$[(W)$—$N(R^{17})SO_2]_qR^{16}$, —$[(W)$—$C(O)N(R^{17})]_qR^{17}$, —$[(W)$—$O]_qR^{16}$, —$[(W)$—$N(R^{17})]_qR^{16}$, or —$[(W)$—$S]_qR^{16}$, wherein W is a diradical and q is 1, 2, 3, 4, 5, or 6;
each $R^2$ and $R^3$ is, independently, H, alkyl, alkenyl, alkynyl, aryl, cycloalkyl, heterocycloalkyl, aralkyl, heteroaryl, heteroaralkyl, haloalkyl, halo, —$OR^{16}$, —$OR^{16}$, —$N(R^{17})_2$, or —$SR^{16}$, or $R^2$ and $R^3$ taken together form a double bond or form a group

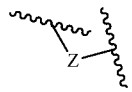

wherein Z is $NR^{17}$, O, or $O(R^{18})_2$,
$R^4$ is independently H, halo, —$OR^{16}$, —$N(R^{17})_2$, or —$SR^{16}$;
each $R^5$ and $R^6$, is, independently, H, alkyl, alkenyl, alkynyl, aryl, cycloalkyl, heterocycloalkyl, aralkyl, heteroaryl, heteroaralkyl, halo, —$OR^{16}$, —$N(R^{17})_2$, or —$SR^{16}$; or $R^5$ and $R^6$ taken together with the carbon to which they are bonded form C=O, C=S, C=N—$OR^{17}$, C=N—$R^{17}$, C=N—$N(R^{17})_2$, or form an optionally substituted 3-8 membered ring;
each $R^7$, $R^8$, $R^9$, $R^{10}$, $R^{11}$, $R^{12}$ and $R^{13}$ is, independently, H, alkyl, alkenyl, alkynyl, aryl, cycloalkyl, heterocycloalkyl, aralkyl, heteroaryl, heteroaralkyl, halo, —$OR^{16}$, —$N(R^{17})_2$, or —$SR^{16}$;
or $R^{10}$ and $R^{11}$ taken together, or $R^{11}$ and $R^{12}$ taken together, form a double bond or form a group

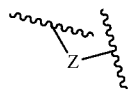

wherein Z is $NR^{17}$, O, or $O(R^{18})_2$,
each $R^{14}$ and $R^{15}$ is, independently, H, halo, —$OR^{16}$, —$N(R^{17})_2$, or —$SR^{16}$; or $R^{14}$ and $R^{15}$ taken together with the carbon to which they are bonded form C=O or C=S;

X is a bond or the group —C(R$^{19}$)$_2$—; wherein each R$^{19}$ is, independently, H, alkyl, aralkyl, halo, —CN, —OR$^{16}$, or —N(R$^{17}$)$_2$, R$^{16}$ is H, alkyl, alkenyl, alkynyl, aryl, cycloalkyl, heterocycloalkyl, aralkyl, heteroaryl, heteroaralkyl or —[C(R$^{20}$)$_2$]$_p$—R$^{21}$ wherein p is 0-6; or any two occurrences of R$^{16}$ on the same substituent are taken together to form a 4-8 membered optionally substituted ring;

R$^{17}$ is H, alkyl, alkenyl, alkynyl, aryl, cycloalkyl, heterocycloalkyl, aralkyl, heteroaryl, heteroaralkyl, —C(=O)R$^{20}$, —C(=O)OR$^{20}$, —SO$_2$R$^{20}$, —C(=O)N(R$^{20}$)$_2$, or —[C(R$^{20}$)$_2$]$_p$—R$^{21}$ wherein p is 0-6; or any two occurrences of R$^{17}$ on the same substituent are taken together to form a 4-8 membered optionally substituted ring;

R$^{18}$ is H, alkyl, alkenyl, alkynyl, aryl, cycloalkyl, heterocycloalkyl, aralkyl, heteroaryl, heteroaralkyl, halo, —CN, —OR$^{20}$, —OSi(R$^{20}$)$_3$, —C(=O)R$^{20}$, —C(=O)OR$^{20}$, —SO$_2$R$^{20}$ or —C(=O)N(R$^2$)$_2$;

R$^{20}$ is H, alkyl, alkenyl, alkynyl, aryl, cycloalkyl, heterocycloalkyl, aralkyl, heteroaryl, or heteroaralkyl; or any two occurrences of R$^{20}$ on the same substituent are taken together to form a 4-8 membered optionally substituted ring;

R$^{21}$ is —OR$^{22}$, —N(R$^{22}$)C(=O)R$^{22}$, —N(R$^{22}$)C(=O)OR$^{22}$, —N(R$^{22}$)SO$_2$(R$^{22}$), —C(=O)R$^{22}$N(R$^{22}$)$_2$, —OC(=O)R$^{22}$N(R$^{22}$)(R$^{22}$), —SO$_2$N(R$^{22}$)(R$^{22}$), —N(R$^{22}$)(R$^{22}$), —C(=O)OR$^{22}$, —C(=O)N(OH)(R$^{22}$), —OS(O)$_2$OR$^{22}$, —S(O)$_2$OR$^{22}$, —OP(=O)(OR$^{22}$)(OR$^{22}$), —N(R$^{22}$)P(O)(OR$^{22}$)(OR$^{22}$), or —P(=O)(OR$^{22}$)(OR$^{22}$); and R$^{22}$ is H, alkyl, alkenyl, alkynyl, aryl, cycloalkyl, heterocycloalkyl, aralkyl, heteroaryl, heteroaralkyl; or any two occurrences of R$^{22}$ on the same substituent are taken together to form a 4-8 membered optionally substituted ring;

said process comprising contacting a compound of formula (I) or a salt thereof, an amino donor molecule, an omega amine transaminase enzyme, and a co-factor in a solution to provide a compound of formula (II) or a salt thereof, wherein the amino donor molecule is an amine, an amino acid, a polypeptide and/or a salt thereof.

2. The process of claim 1, wherein the co-factor is pyridoxal phosphate (PLP).

3. The process of claim 1, wherein the co-factor is a co-enzyme.

4. The process of claim 3, wherein the co-enzyme is selected from L-alanine dehydrogenase (LADH), lactate dehydrogenase (LDH), nicotinamide adenine dinucleotide phosphate (NADPH), nicotinamide adenine dinucleotide (NAD), formate dehydrogenase (FDH), and glucose dehydrogenase (GDH).

5. The process of claim 1, wherein the process further comprises adding a pyruvate reductase mix to the solution.

6. The process of claim 1, wherein the omega amine transaminase is selected from the group consisting of ATA-101, ATA-102, ATA-103, ATA-104, ATA-105, ATA-106, ATA-107, ATA-108, ATA-109, ATA-110, ATA-113, ATA-114, ATA-115, ATA-116, ATA-117, ATA-124, an omega amine transaminase from Chromobacterium *violaceum*, an omega amine transaminase from *Alcaligenes denitrificans*, an omega amine transaminase from *Arthrobactercitreus*, an omega amine transaminase from *Klebsiella pneumoniae*, an omega amine transaminase from *Bacillus thuringiensis*, an omega amine transaminase from *Bacillus cereus*, and an omega amine transaminase from *Vibrio fluvialis*.

7. The process of claim 1, wherein the amino donor molecule is selected from pyridoxamine, methylbenzylamine, 2-aminobutane, propyl amine, isopropyl amine, 1,1,1-trifluoropropan-2-amine, 1,1,1,3,3,3-hexafluoropropan-2-amine, benzyl amine, 2-amino-1-butanol, 1-amino-1-phenylethane, 1-amino-1-(2-methoxy-5-fluorophenyl) ethane, 1-amino-1-phenylpropane, 1-amino-1-(4hydroxyphenyl)propane, 1-amino-1-(4-bromophenyl) propane, 1-amino-1-(4-nitrophenyl)propane, 1-phenyl-2-aminopropane, 1-(3-trifluoromethylphenyl)-2-aminopropane, 2-aminopropanol, 1-amino-1-phenylbutane, 1-phenyl-2-aminobutane, 1-(2,5-dimethoxy-4-methylphenyl)-2-aminobutane, 1-phenyl-3-aminobutane, 1-(4-hydroxyphenyl)-3-aminobutane, 1-amino-1-(2-naphthyl)ethane, cis-2-methylcyclopentanamine, trans-2-methylcyclopentanamine, cis-3-methylcyclopentanamine, trans-3-methylcyclopentanamine, cis-2-ethylcyclopentanamine, trans-2-ethylcyclopentanamine, cis-3-ethylcyclopentanamine, trans-3-ethylcyclopentanamine, cis-2-methylcyclohexanamine, trans-2-methylcyclohexanamine, cis-3-methylcyclohexanamine, trans-3-methylcyclohexanamine, cis-2-ethylcyclohexanamine, trans-2-ethylcyclohexanamine, cis-3-ethylcyclohexanamine, trans-3-ethylcyclohexanamine, 1-aminotetralin, 2-aminotetralin, 2-amino-5-methoxytetralin, 1-aminoindane, 2-aminoindane, 2-amino-1-propanol, cis-1-amino-2-indanol, trans-1-amino-2-indanol, 1-amino-6-hydroxyindanamine, taurine, and salts thereof.

8. The process of claim 1, wherein the amino donor molecule is selected from glycine, alanine, aspartic acid, phenylalanine, 2-aminopentanedioic acid, 3-aminobutyrate, γ-aminobutyrate, β-alanine, asparagine, cysteine, glutamic acid, glutamine, proline, selenocysteine, serine, tyrosine, arginine, histidine, ornithine, isoleucine, leucine, lysine, methionine, threonine, tryptophan, valine, and polypeptides thereof and/or salts thereof.

9. The process of claim 1, wherein the amino donor molecule is a chiral amino donor molecule.

10. The process of claim 1, wherein the solution is a buffered solution.

11. The process of claim 1, wherein the pH of the solution is between about 5 and about 9.

12. The process of claim 1, wherein R$^1$ is H, aralkyl or —CO$_2$R$^{16}$.

13. The process of claim 1, wherein R$^2$ and R$^3$ taken together form a double bond or form a group:

wherein Z is NR$^{17}$, O, or O(R$^{18}$)$_2$.

14. The process of claim 1, wherein X is a bond or is the group —C(R$^{19}$)$_2$—.

15. The process of claim 1, wherein R$^4$ is H.

16. The process of claim 1, wherein each of R$^5$ and R$^6$ is independently H, or R$^5$ and R$^6$ taken together with the carbon to which they are bonded form C=O.

17. The process of claim 1, wherein R$^7$ and R$^8$ are each H.

18. The process of claim 1, wherein R$^9$ and R$^{10}$ are each H.

19. The process of claim 1, wherein R$^{11}$ is a H.

20. The process of claim 1, wherein R$^{12}$ and R$^{13}$ are each H.

21. The process according to claim 1, wherein $R^9$ is H and $R^{10}$ and $R^{11}$ taken together form a double bond.

22. The process of claim 1, wherein $R^{13}$ is H, and $R^{11}$ and $R^{12}$ taken together form a double bond.

23. The process of claim 1, wherein each of $R^9$, $R^{10}$, $R^{11}$, $R^{12}$, and $R^{13}$ is H.

24. The process of claim 1, wherein $R^{14}$ and $R^{15}$ are each H.

25. The process of claim 1, wherein the compound of formula (I) or a salt thereof and a compound of formula (II) or a salt thereof are selected from a pair of compounds:

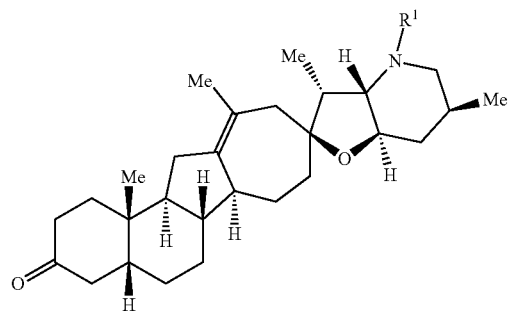
(I-a)

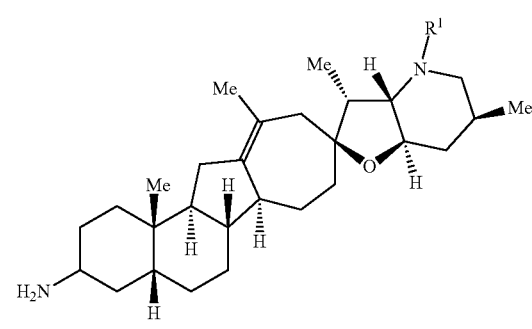
(II-a)

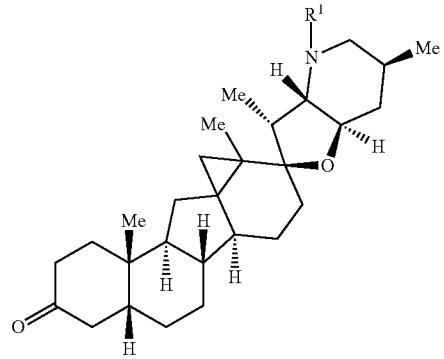
(I-b)

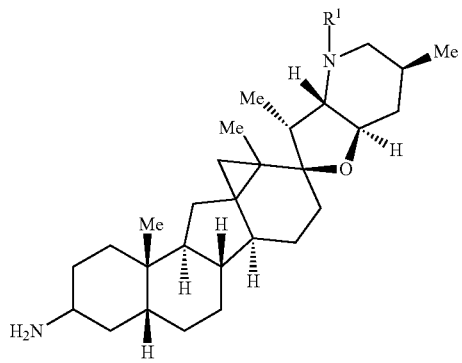
(II-b)

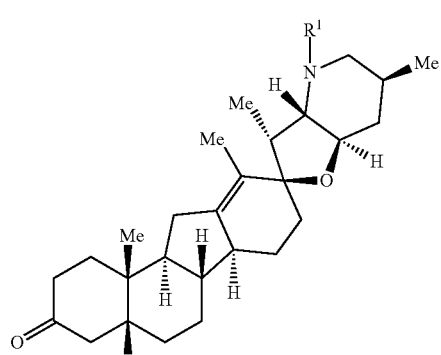
(I-c)

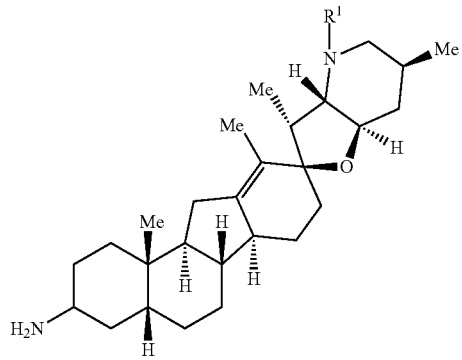
(II-c)

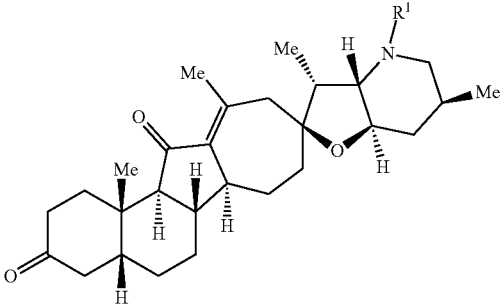
(I-d)

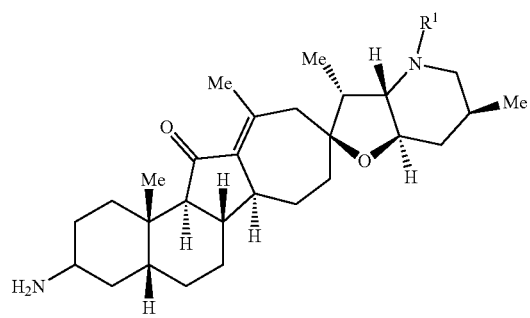
(II-d)
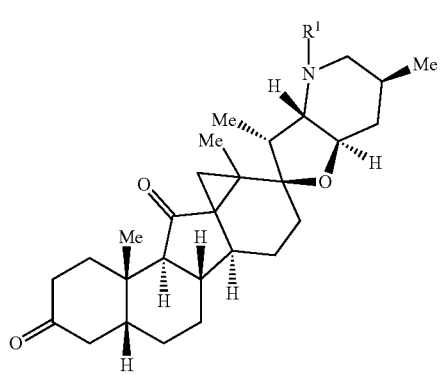
(I-e)
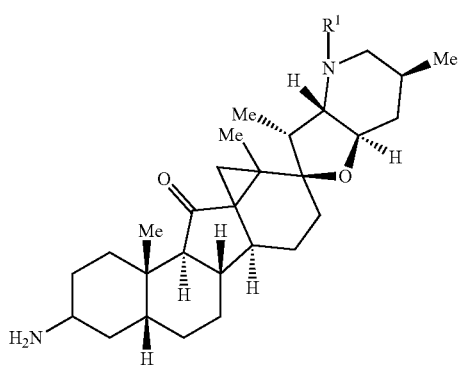
(II-e)
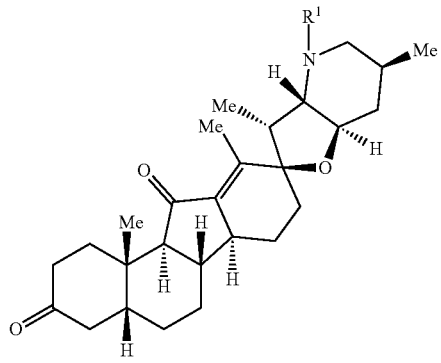
(I-f)
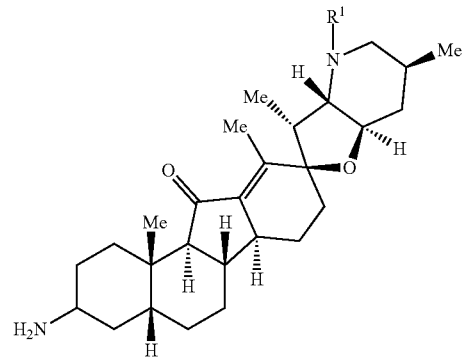
(II-f)
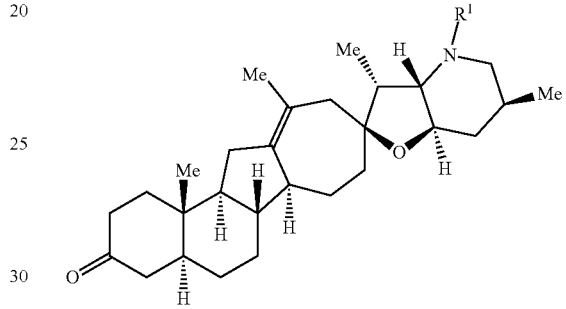
(I-g)
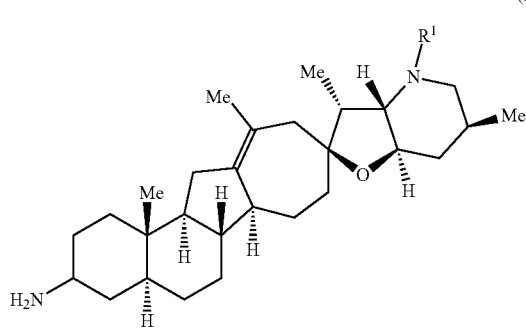
(II-g)
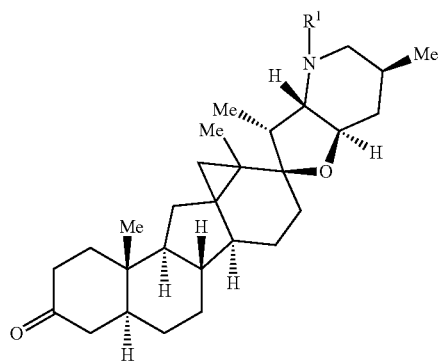
(I-h)

(II-h)
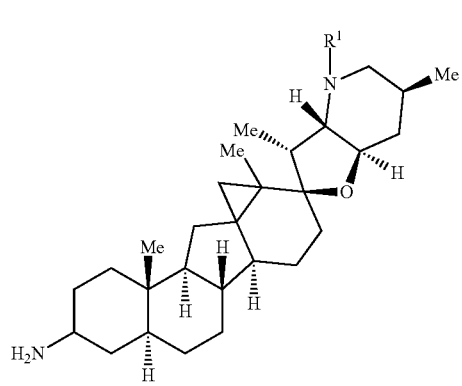
(I-i)
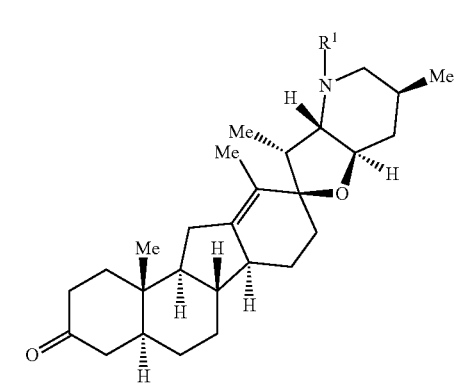
(II-i)
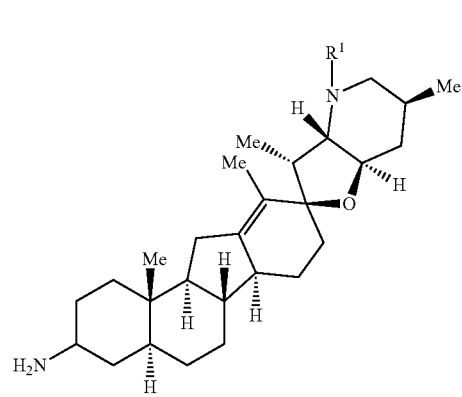
(I-j)
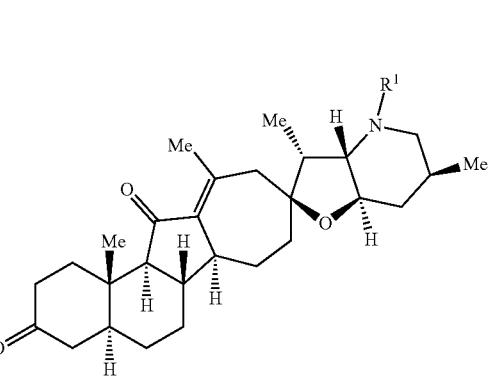
(II-j)
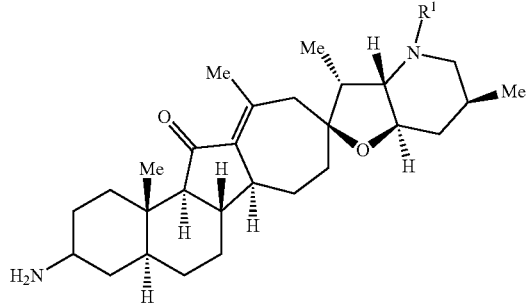
(I-k)
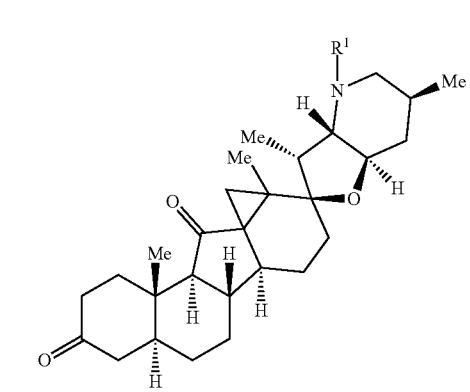
(II-k)
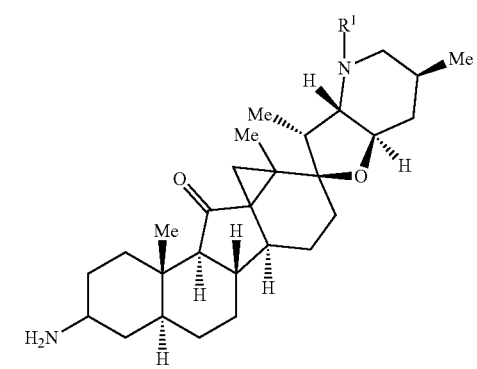
(I-l)
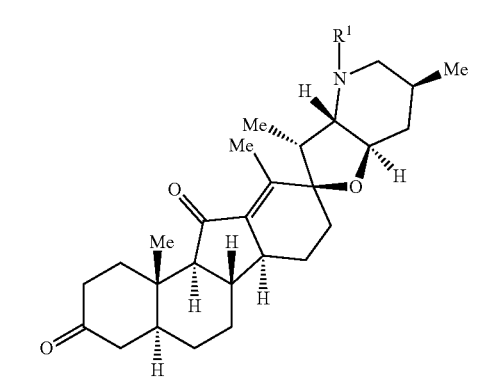

-continued (II-l)

(I-m)

(II-m)

(I-n)

(II-n)

(I-o)

(II-o)

(I-p)

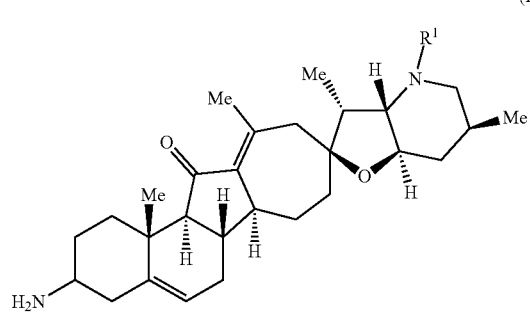
(II-p)
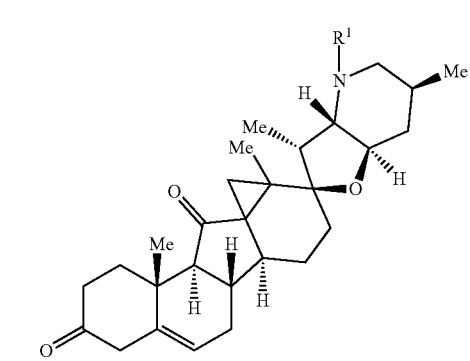
(I-q)
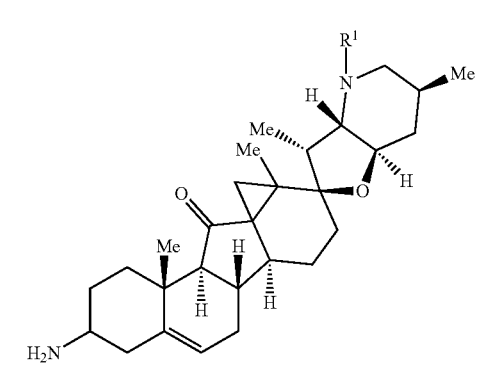
(II-q)
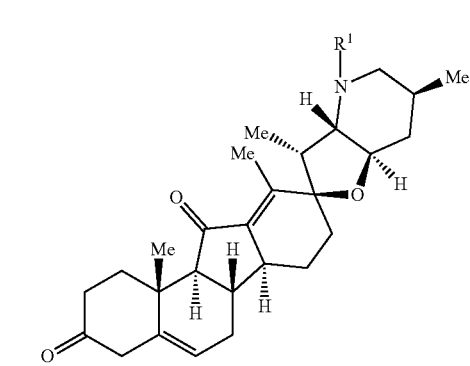
(I-r)
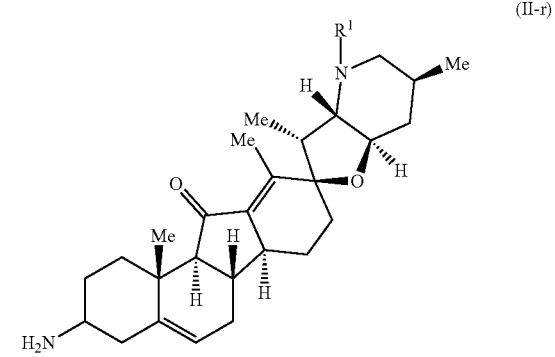
(II-r)
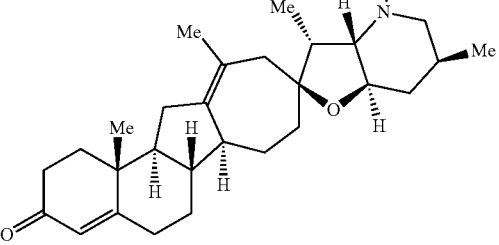
(I-s)
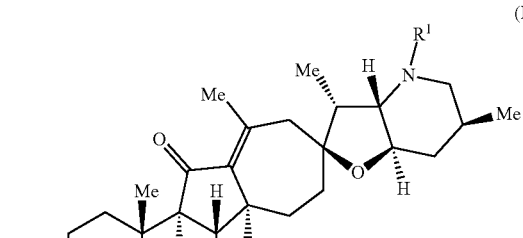
(II-s)
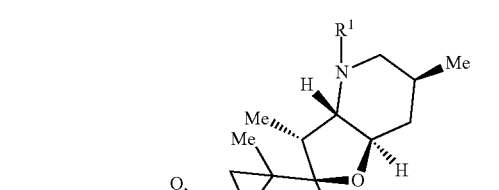
(I-t)
(II-t)

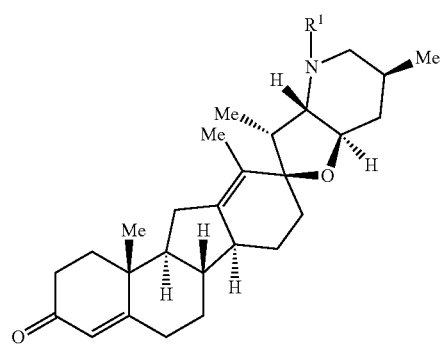
(I-u)
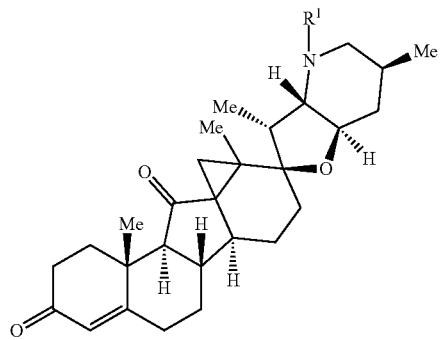
(I-w)
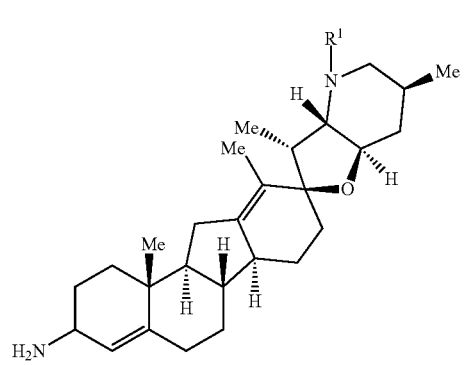
(II-u)
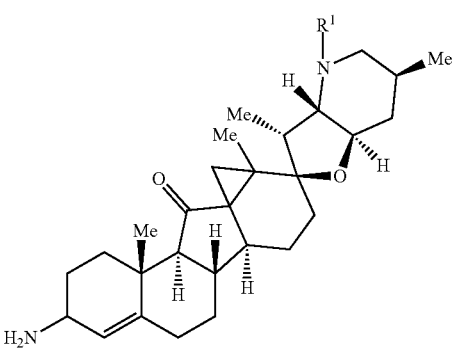
(II-w)
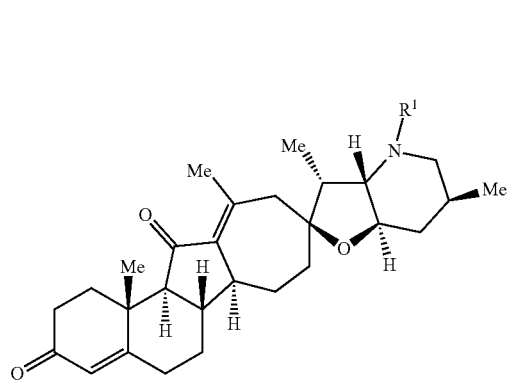
(I-v)
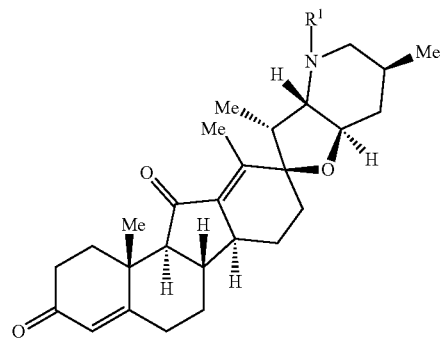
(I-x)
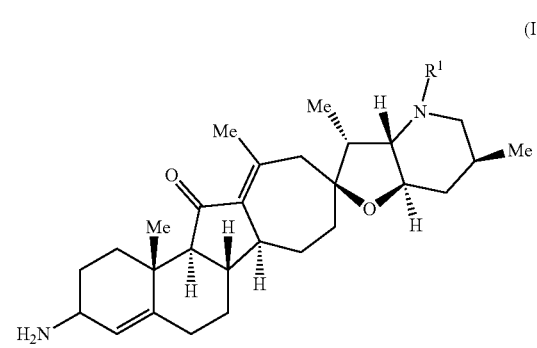
(II-v)
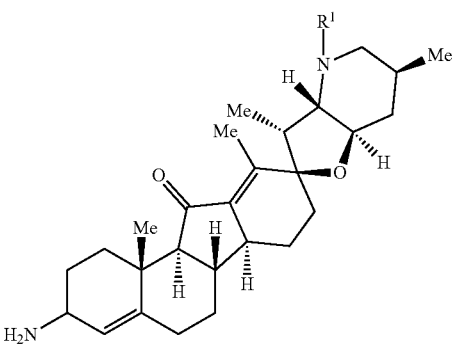
(II-x)

-continued
(I-a)
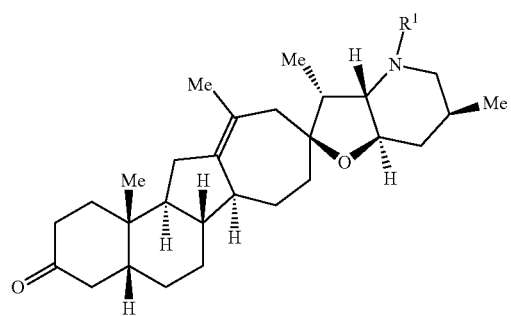
(R)-(II-a)
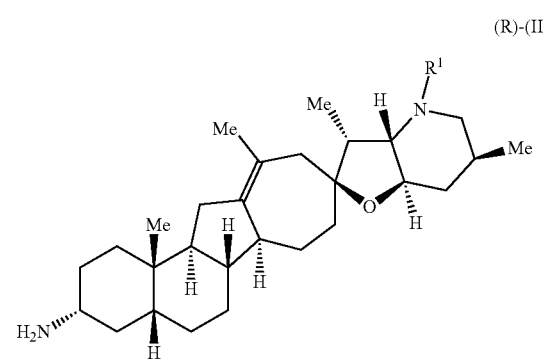
(I-b)
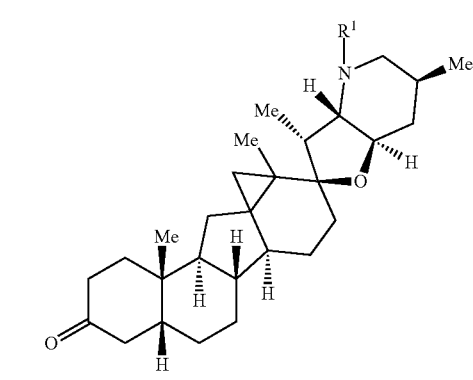
(R)-(II-b)
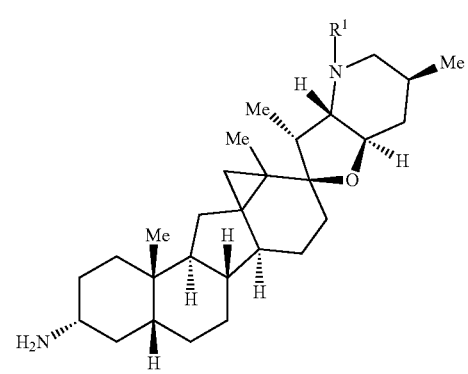
-continued
(I-c)
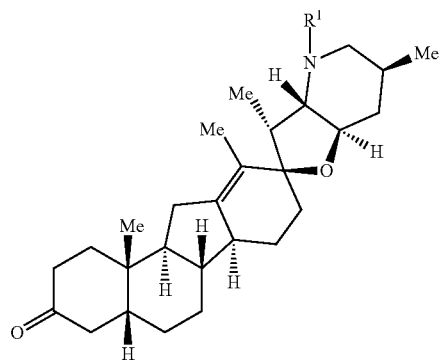
(R)-(II-c)
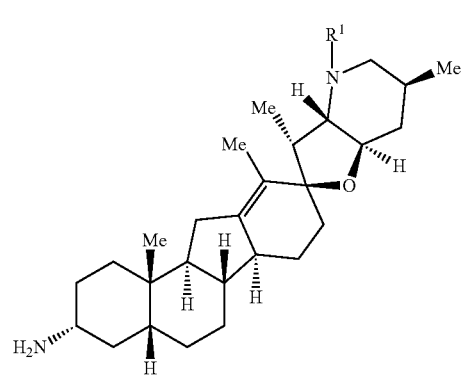
(I-d)
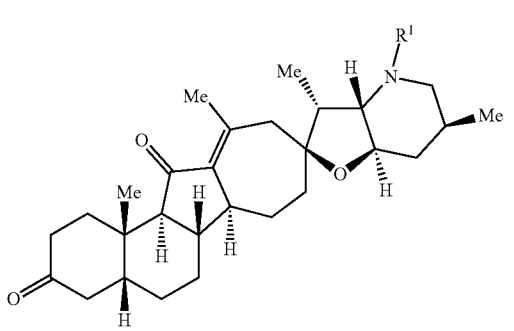
(R)-(II-d)
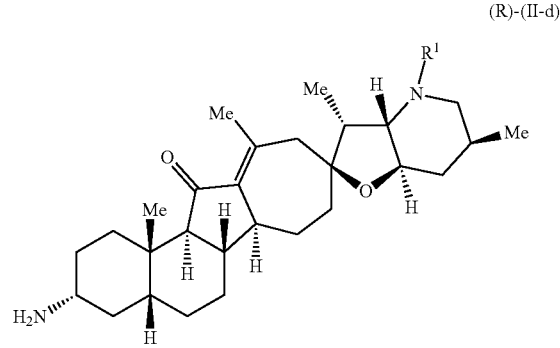

-continued

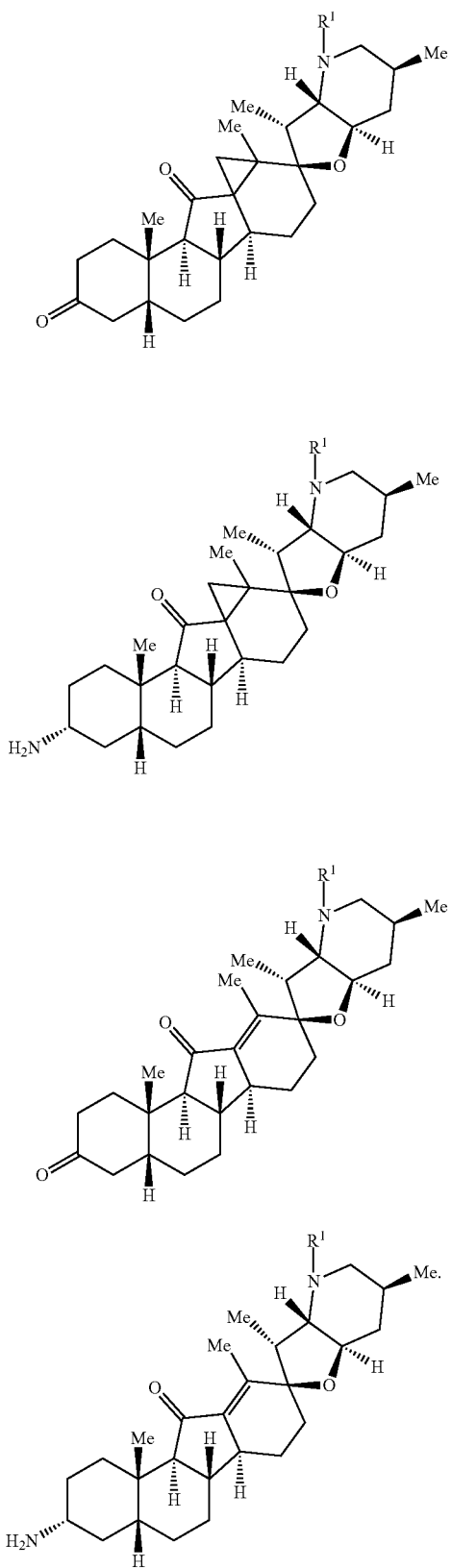

26. The process of claim 1, wherein the compound of formula (I) is a compound of formula (I-a):

or salt thereof,
and the compound of formula (II) is a compound of formula (R)-(II-a):

or a salt thereof.

27. The process of claim 1, further comprising contacting a compound of formula (II) or a salt thereof with a sulfonylating agent to provide a compound of formula (III):

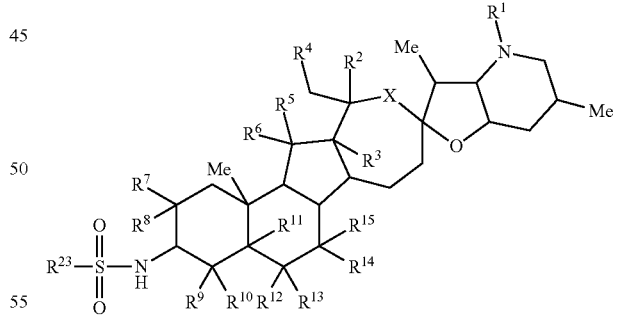

or a salt thereof,
wherein $R^{23}$ is alkyl or aryl.

28. The process of claim 27, wherein the sulfonylating agent is selected from benzenesulfonyl chloride, benzenesulfonyl anhydride, p-toluenesulfonyl chloride, p-toluenesulfonyl anhydride, methanesulfonyl chloride, and methanesulfonyl anhydride.

29. The process of claim 27, wherein the sulfonylating agent is methanesulfonyl chloride or methanesulfonyl anhydride, and $R^{23}$ is —$CH_3$.

30. The process of claim 1, wherein the process preferentially generates a compound of formula II or a salt thereof wherein the newly-formed amino group has R-stereochemistry.

\* \* \* \* \*